(12) United States Patent
Hendrix et al.

(10) Patent No.: US 8,076,355 B2
(45) Date of Patent: Dec. 13, 2011

(54) 2-HETEROARYLCARBOXYLIC ACID AMIDES

(75) Inventors: Martin Hendrix, Odenthal (DE); Frank-Gerhard Böβ, Sunninghill (GB); Christina Erb, Kriftel (DE); Timo Fleβner, Wuppertal (DE); Marja Van Kampen, Neu-Isenburg (DE); Joachim Luithle, Wülfrath (DE); Christoph Methfessel, Wuppertal (DE); Welf-Burkhard Wiese, Wermelskirchen (DE)

(73) Assignee: Bayer Schering Pharma Aktiengesellschaft, Berlin (DE)

( * ) Notice: Subject to any disclaimer, the term of this patent is extended or adjusted under 35 U.S.C. 154(b) by 0 days.

(21) Appl. No.: 12/777,764

(22) Filed: May 11, 2010

(65) Prior Publication Data

US 2010/0222378 A1     Sep. 2, 2010

Related U.S. Application Data

(63) Continuation of application No. 10/500,096, filed as application No. PCT/EP02/14288 on Dec. 16, 2002, now Pat. No. 7,732,477.

(30) Foreign Application Priority Data

Dec. 27, 2001 (DE) .................... 101 64 139

(51) Int. Cl.
*A61K 31/4365* (2006.01)
*A61K 31/439* (2006.01)
*A61P 25/28* (2006.01)

(52) U.S. Cl. ......................... 514/301; 514/305

(58) Field of Classification Search ............... None
See application file for complete search history.

(56) References Cited

U.S. PATENT DOCUMENTS

| | | | |
|---|---|---|---|
| 4,605,652 A | 8/1986 | Welstead, Jr. | |
| 5,561,149 A | 10/1996 | Azria et al. | |
| 5,599,937 A | 2/1997 | Glas et al. | |
| 6,911,543 B2 | 6/2005 | Walker et al. | |

FOREIGN PATENT DOCUMENTS

| | | |
|---|---|---|
| DE | 3724059 A1 | 2/1988 |
| DE | 3810552 A1 | 10/1989 |
| EP | 0327335 A1 | 8/1989 |
| EP | 353371 A1 | 2/1990 |
| EP | 0485962 A2 | 5/1992 |
| EP | 0512350 A2 | 11/1992 |
| JP | 2002030084 A | 1/2002 |
| WO | WO-93/15073 A1 | 8/1993 |
| WO | WO-96/33186 A1 | 10/1996 |
| WO | WO-02/15662 A2 | 2/2002 |
| WO | WO-02/100857 A1 | 12/2002 |
| WO | WO-03/029252 A1 | 4/2003 |
| WO | WO-03/037896 A1 | 5/2003 |

OTHER PUBLICATIONS

J-L. Galzi et al.: "Neuronal Nicotinic Receptors: Molecular Organization and Regulations," Neuropharmacology, vol. 34, No. 6, 1995, pp. 563-582.
D. S. McGehee et al.: "Physiological Diversity of Nicotinic Acetylcholine Receptors Expressed by Vertebrate Neurons," Annu. Rev. Physiol., vol. 57, 1995, pp. 521-546.
A. H. Rezvani et al.: "Cognitive Effects of Nicotine," Biological Pshychiatry, vol. 49, 2001, pp. 258-267.
P. Seguela et al.: "Molecular Cloning, Functional Properties, and Distribution of Rat Brain $\alpha_7$: A Nicotinic Cation Channel Highly Permeable to Calcium," The Journal fo Neuroscience, vol. 13, No. 2, Feb. 1993, pp. 596-604.
S. R. Vippagunta et al.: "Crystalline Solids," Advanced Drug Delivery Reviews, vol. 48, 2001, pp. 3-26.
R. S. Broide et al.: "The $\alpha_7$ Nicotinic Acetylcholine Receptor in Neuronal Plasticity," Molecular Neurobiology, vol. 20, 1999, pp. 1-16.
D. Bogdal et al., "Microwave-Assisted Preparation of Benzo[b]furans under Solventless Phase-Transfer Catalytic Conditions," Tetrahedron 56 (2000) 8769-8773.
A. Ennaceur et al., "A new one-trial test for neurobiological studies of memory in rats. 1: Behavioral data," Behavioural Brain Research, 31 (1988) 47-59.
J. Prickaerts et al., "Possible role of nitric oxide-cyclic GMP pathway in object recognition memory: Effects of 7-nitroindazole and zaprinast", European Journal of Pharmacology 337 (1997) 125-136.
A. Blokland, et al., "State-dependent impairment in object recognition after hippocampal NOS inhibition", NeuroReport vol. 8, No. 18 (Dec. 1998) 4205-4208.
A.R.L. Davies, et al., "Characterisation of the binding of [3H]methyllycaconitine: a new radioligand for labelling 7-type neuronal nicotinic acetylcholine receptors" Neuropharmacology 38 (1999) 679-690.
A. Ennaceur et al., "Effects of physostigmine and scopolamine on rats' performances in object-recognition and radial-maze tests" Psychopharmacology 109 (1992) 321-330.
B. Bhat et al., "A Novel One-Step Synthesis of 2-Methoxycarbonylthieno[2,3-b]quinolines and 3-Hydroxy-2-methoxycarbonyl-2,3-dihydrothieno[2,3-b]-quinolines" Synthesis (Aug. 1984) 673-676.
A.J. Bridges et al., "Fluorine as an ortho-Directing Group in Aromatic Metalation: A Two Step Preparation of Substituted Benzo[b]thiophene-2-carboxylates" Tetrahedron Letters vol. 33, No. 49 (1992) 7499-7502.

*Primary Examiner* — Kamal Saeed
(74) *Attorney, Agent, or Firm* — Edwards Wildman Palmer LLP; Ralph A. Loren; Nicholas J. DeCeglie, Jr.

(57) ABSTRACT

The invention relates to novel 2-heteroarylcarboxamides, processes for their preparation, and their use for producing medicaments for the treatment and/or prophylaxis of diseases and for improving perception, concentration, learning and/or memory.

18 Claims, No Drawings

2-HETEROARYLCARBOXYLIC ACID AMIDES

CROSS REFERENCE TO RELATED APPLICATIONS

This application is a continuation of U.S. patent application Ser. No. 10/500,096, filed on Jan. 11, 2005, which is a U.S. National Stage application under 35 U.S.C. §371 of International Patent Application Serial No. PCT/EP02/14288, filed Dec. 16, 2002, which claims priority to German Application No. 10164139.7, filed Dec. 27, 2001, the disclosures of each of which are expressly incorporated by reference in their entireties.

FIELD OF THE INVENTION AND BACKGROUND

The invention relates to novel 2-heteroarylcarboxamides, processes for their preparation, and their use for producing medicaments for the treatment and/or prophylaxis of diseases and for improving perception, concentration, learning and/or memory.

Nicotinic acetylcholine receptors (nAChR) form a large family of ion channels which are activated by the messenger acetylcholine which is produced in the body (Galzi and Changeux, *Neuropharmacol.* 1995, 34, 563-582). A functional nAChR consists of five subunits which may be different (certain combinations of α1-9 and β1-4,γ,δ,ε subunits) or identical (α7-9). This leads to the formation of a diversity of subtypes which differ in the distribution in the muscles, the nervous system and other organs (McGehee and Role, *Annu. Rev. Physiol.* 1995, 57, 521-546). Activation of nAChR leads to influx of cations into the cell and to stimulation of nerve cells or muscle cells. Selective activation of individual nAChR subtypes restricts this stimulation to the cell types which have a corresponding subtype and is thus able to avoid unwanted side effects such as, for example, stimulation of nAChR in the muscles. Clinical experiments with nicotine and experiments in various animal models indicate that central nicotinic acetylcholine receptors are involved in learning and memory processes (e.g. Rezvani and Levin, *Biol. Psychiatry* 2001, 49, 258-267). Nicotinic acetylcholine receptors of the alpha7 subtype (α7 nAChR) have a particularly high concentration in regions of the brain which are important for learning and memory, such as the hippocampus and the cerebral cortex (Séguéla et al., *J. Neurosci.* 1993, 13, 596-604). The α7 nAChR has a particularly high permeability for calcium ions, increases glutamatergic neurotransmission, influences the growth of axons and, in this way, modulates neuronal plasticity (Broide and Leslie, *Mol. Neurobiol* 1999, 20, 1-16).

Certain N-(1-azabicyclo[2.2.2]oct-3-yl)heteroaryl carboxamides for the treatment of, inter alia, psychoses are described in DE-A 37 24 059.

N-(Azabicycloalkyl)heteroaryl carboxamides, in particular N-(1-azabicyclo-[2.2.2]oct-4-yl)benzothiophene-3-carboxamides, are disclosed in WO 93/15073 and in EP-A 0 485 962 as intermediates for the synthesis of pharmaceutically active compounds.

1-Azabicycloalkanes and their action on the nicotinic α7-receptor are known from JP 14030084A.

U.S. Pat. No. 4,605,652 and EP-A 0 372 335 disclose, for example, N-(1-azabicyclo[2.2.2]oct-3-yl)thiophene-2-carboxamide and its memory-improving effect.

The present invention relates to compounds of the formula (I)

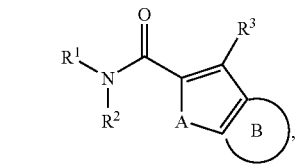

in which
$R^1$ represents 1-azabicyclo[2.2.2]oct-3-yl,
$R^2$ represents hydrogen or $C_1$-$C_6$-alkyl,
$R^3$ represents hydrogen, halogen or $C_1$-$C_6$-alkyl,
A represents oxygen or sulfur,
and
the ring B represents benzo, pyrido, pyrimido, pyridazo or pyridazino which are optionally substituted by radicals selected from the group consisting of hydrogen, halogen, $C_1$-$C_6$-alkanoyl, carbamoyl, cyano, trifluoromethyl, trifluoromethoxy, nitro, amino, $C_1$-$C_6$-acylamino, $C_1$-$C_6$-alkyl, $C_1$-$C_6$-alkoxy, $C_1$-$C_6$-alkylthio, $C_1$-$C_6$-alkylamino, heteroarylcarbonylamino, arylcarbonylamino, $C_1$-$C_4$-alkylsulfonylamino, di-($C_1$-$C_4$-alkylsulfonyl)amino, arylsulfonylamino, di(arylsulfonyl)amino, $C_3$-$C_6$-cycloalkylcarbonylmethyl, 1,3-dioxapropane-1,3-diyl, amino(hydroxyimino)methyl and benzo,
and their salts, solvates and solvates of the salts.

The compounds according to the invention can exist in stereoisomeric forms which are either like image and mirror image (enantiomers) or which are not like image and mirror image (diastereomers). The invention relates both to the enantiomers and diastereomers and to their respective mixtures. These mixtures of the enantiomers and diastereomers can be separated in a known manner into the stereoisomeric uniform components.

Compounds according to the invention can also be present in the form of their salts, solvates or solvates of the salts.

Salts which are preferred for the purposes of the invention are physiologically acceptable salts of the compounds of the invention.

Physiologically acceptable salts of the compounds according to the invention may be acid addition salts of the compounds with mineral acids, carboxylic acids or sulfonic acids. Particularly preferred examples are salts with hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, propionic acid, lactic acid, tartaric acid, citric acid, fumaric acid, maleic acid or benzoic acid.

However, salts which may be mentioned are also salts with conventional bases, such as, for example, alkali metal salts (e.g. sodium or potassium salts), alkaline earth metal salts (e.g. calcium or magnesium salts) or ammonium salts derived from ammonia or organic amines such as, for example, diethylamine, triethylamine, ethyldiisopropylamine, procaine, dibenzylamine, N-methylmorpholine, dihydroabiethylamine, 1-ephenamine or N-methylpiperidine.

Solvates is the term used for the purposes of the invention for those forms of the compounds which form a complex with solvent molecules by coordination in the solid or liquid state. Hydrates are a special form of solvates in which the coordination takes place with water.

For the purposes of the present invention, the substituents generally have the following meaning:
$C_1$-$C_6$- and $C_1$-$C_4$-Alkoxy are a straight-chain or branched alkoxy radical having 1 to 6 and 1 to 4 carbon atoms, respectively. Preference is given to a straight-chain or branched alkoxy radical having 1 to 4, particularly preferably 1 to 3, carbon atoms. The following radicals may be mentioned by way of example and by way of preference: methoxy, ethoxy, n-propoxy, isopropoxy, tert-butoxy, n-pentoxy and n-hexoxy.

$C_1$-$C_6$- and $C_1$-$C_4$-Alkyl are a straight-chain or branched alkyl radical having 1 to 6 and 1 to 4 carbon atoms, respectively. Preference is given to a straight-chain or branched alkyl radical having 1 to 4, particularly preferably 1 to 3, carbon atoms. The following radicals may be mentioned by way of example and by way of preference: methyl, ethyl, n-propyl, isopropyl, tert-butyl, n-pentyl and n-hexyl.

($C_1$-$C_6$)-Alkanoyl is a straight-chain or branched alkyl radical having 1 to 6 carbon atoms which carries a doubly attached oxygen atom in the 1-position and is attached via the 1-position. Preference is given to a straight-chain or branched alkanoyl radical having 1 to 4, particularly preferably 1 to 2, carbon atoms. The following radicals may be mentioned by way of example and by way of preference: formyl, acetyl, propionyl, n-butyryl, isobutyryl, pivaloyl and n-hexanoyl.

$C_1$-$C_6$-Alkylamino is a straight-chain or branched alkylamino radical having 1 to 6 carbon atoms, preferably 1 to 4, particularly preferably 1 to 3, carbon atoms. Nonlimiting examples include methylamino, ethylamino, n-propylamino, isopropylamino and tert-butylamino.

($C_1$-$C_6$)-Acylamino is an amino group having a straight-chain or branched alkanoyl substituent which has 1 to 6 carbon atoms and is attached via the carbonyl group. Preference is given to an acylamino radical having 1 to 4, particularly preferably 1 to 2, carbon atoms. The following radicals may be mentioned by way of example and by way of preference: formamido, acetamido, propionamido, n-butyramido and pivaloylamido.

$C_1$-$C_4$-Alkylsulfonylamino is a straight-chain or branched alkylsulfonylamino radical having 1 to 4, preferably 1 to 3, carbon atoms. Nonlimiting examples include methylsulfonylamino, ethylsulfonylamino, n-propylsulfonylamino, isopropyl-sulfonylamino, tert-butylsulfonylamino.

Arylsulfonylamino is a naphthyl- or phenylsulfonylamino radical and preferably a phenylsulfonylamino radical.

$C_1$-$C_6$-Alkylthio is a straight-chain or branched alkylthio radical having 1 to 6 carbon atoms. Preference is given to a straight-chain or branched alkylthio radical having 1 to 4, particularly preferably 1 to 3, carbon atoms. The following radicals may be mentioned by way of example and by way of preference: methylthio, ethylthio, n-propylthio, isopropylthio, tert-butylthio, n-pentylthio and n-hexylthio.

Arylcarbonyl is a naphthyl- or phenylcarbonyl radical and preferably a phenylcarbonyl radical (Benzoyl radical).

Heteroarylcarbonyl is a heteroarylcarbonyl radical having a 5- to 6-membered, preferably a 5-membered, heteroaryl ring having up to 2 heteroatoms selected from the group consisting of O, S and N. Nonlimiting examples include thienylcarbonyl, furylcarbonyl, pyrrolylcarbonyl, thiazolylcarbonyl, oxazolylcarbonyl, imidazolylcarbonyl, pyridylcarbonyl, pyrimidylcarbonyl.

$C_3$-$C_6$-Cycloalkylcarbonylmethyl is a monocyclic cycloalkyl group having 3 to 6 carbon atoms which is attached via a carbonylmethyl group [—C(=O)—CH$_2$—]. Nonlimiting examples include cyclopropylcarbonylmethyl, cyclopentylcarbonylmethyl and cyclohexylcarbonylmethyl.

Halogen is fluorine, chlorine, bromine and iodine. Preference is given to fluorine, chlorine and bromine. Particular preference is given to fluorine and chlorine.

When radicals in the compounds according to the invention are optionally substituted, unless indicated otherwise the radicals may have one or more identical or different substituents. Preference is given to radicals substituted by up to three identical or different substituents.

Preference is given to compounds of the formula (I), in which
$R^1$ represents 1-azabicyclo[2.2.2]oct-3-yl,
$R^2$ represents hydrogen or ($C_1$-$C_6$)-alkyl,
$R^3$ represents hydrogen, halogen or ($C_1$-$C_6$)-alkyl,
A represents oxygen or sulfur,
and
the ring B represents benzo, pyrido, pyrimido, pyridazo or pyridazino which are optionally substituted by radicals selected from the group consisting of hydrogen, halogen, formyl, carbamoyl, cyano, trifluoromethyl, trifluoromethoxy, nitro, amino, formamido, acetamido, ($C_1$-$C_6$)-alkyl, ($C_1$-$C_6$)-alkoxy, ($C_1$-$C_6$)-alkylthio and benzo.

Particular preference is given to compounds of the formula (I),
in which
$R^1$ represents 1-azabicyclo[2.2.2]oct-3-yl,
$R^2$ represents hydrogen,
$R^3$ represents hydrogen, chlorine, fluorine or methyl,
A represents oxygen or sulfur,
and
the ring B represents benzo or pyrido, where benzo or pyrido is optionally substituted by 1 to 3 radicals selected from the group consisting of hydrogen, halogen, formyl, carbamoyl, cyano, trifluoromethyl, trifluoromethoxy, nitro, amino, formamido, acetamido, $C_1$-$C_4$-alkyl, $C_1$-$C_4$-alkoxy, $C_1$-$C_4$-alkylthio, $C_1$-$C_4$-alkylamino, furylcarbonylamino, phenylcarbonylamino, methylsulfonylamino, di(phenylsulfonyl)amino, cyclopropylcarbonylmethyl, 1,3-dioxapropane-1,3-diyl, amino(hydroxyimino)methyl and benzo.

Especially preferred are compounds of the formula (Ia)

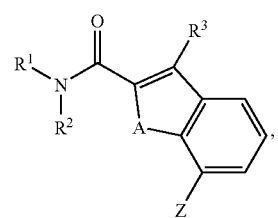

(Ia)

in which
$R^1$ represents 1-azabicyclo[2.2.2]oct-3-yl,
$R^2$ represents hydrogen or $C_1$-$C_6$-alkyl,
$R^3$ represents hydrogen, halogen or $C_1$-$C_6$-alkyl,
A represents oxygen or sulfur,
and
Z represents hydrogen, halogen, formyl, carbamoyl, cyano, trifluoromethyl, trifluoromethoxy, nitro, amino, formamido, acetamido, $C_1$-$C_6$-alkoxy, $C_1$-$C_6$-alkylthio, $C_1$-$C_6$-alkylamino, heteroarylcarbonylamino, arylcarbonylamino, $C_1$-$C_4$-alkylsulfonylamino, di(arylsulfonyl)amino, $C_3$-$C_6$-cycloalkylcarbonylmethyl or amino(hydroxyimino)methyl.

Very particular preference is given to compounds of the formula (Ia),
in which
$R^1$ represents 1-azabicyclo[2.2.2]oct-3-yl,
$R^2$ represents hydrogen,
$R^3$ represents hydrogen, chlorine, fluorine or methyl,
A represents oxygen or sulfur,
and Z represents hydrogen, halogen, formyl, carbamoyl, cyano, trifluoromethyl, trifluoromethoxy, nitro, amino, formamido, acetamido, methyl, ethyl, methoxy, ethoxy, $C_1$-$C_4$-alkylamino, furylcarbonylamino, phenylcarbonylamino, methylsulfonylamino, di(phenylsulfonyl)amino, cyclopropylcarbonylmethyl or amino(hydroxyimino)methyl.

Particularly preferred are compounds of the formula (Ia),
in which
$R^1$ represents (3R)-1-azabicyclo[2.2.2]oct-3-yl,
$R^2$ represents hydrogen,
$R^3$ represents hydrogen, chlorine, fluorine or methyl,
A represents oxygen or sulfur,
and
Z represents hydrogen, halogen, formyl, carbamoyl, cyano, trifluoromethyl, trifluoromethoxy, nitro, amino, formamido, acetamido, methyl, ethyl, methoxy, ethoxy, $C_1$-$C_4$-alkylamino, furylcarbonylamino, phenylcarbonylamino, methylsulfonylamino, di(phenylsulfonyl)amino, cyclopropylcarbonylmethyl or amino(hydroxyimino)methyl.

Also preferred are compounds of the formula (I),
in which
$R^1$ represents (3R)-1-azabicyclo[2.2.2]oct-3-yl,
and $R^2$, $R^3$, A and the ring B are as defined above.

Particularly preferred are compounds of the formula (Ia),
in which
$R^1$ represents (3R)-1-azabicyclo[2.2.2]oct-3-yl,
and $R^2$, $R^3$, A and Z are as defined above.

Also preferred are compounds of the formula (I),
in which
$R^2$ represents hydrogen or methyl,
and $R^1$, $R^3$, A and the ring B are as defined above.

Particularly preferred are compounds of the formula (I),
in which
$R^2$ represents hydrogen,
and $R^1$, $R^3$, A and the ring B are as defined above.

Also preferred are compounds of the formula (I),
in which
$R^3$ represents hydrogen, fluorine, chlorine or methyl,
and $R^1$, $R^2$, A and the ring B are as defined above.

Particularly preferred are compounds of the formula (I),
in which
$R^3$ represents hydrogen or methyl,
and $R^1$, $R^2$, A and the ring B are as defined above.

Very particularly preferred are compounds of the formula (I),
in which
$R^3$ represents hydrogen,
and $R^1$, $R^2$, A and the ring B are as defined above.

Also preferred are compounds of the formula (I),
in which
A represents sulfur,
and $R^1$, $R^2$, $R^3$ and the ring B are as defined above.

Also preferred are compounds of the formula (I),
in which
A represents oxygen,
and $R^1$, $R^2$, $R^3$ and the ring B are as defined above.

Particularly preferred are compounds of the formula (Ia),
in which
A represents sulfur,
and $R^1$, $R^2$, $R^3$ and Z are as defined above.

Also particularly preferred are compounds of the formula (Ia),
in which
A represents oxygen,
and $R^1$, $R^2$, $R^3$ and Z are as defined above.

Also preferred are compounds of the formula (I),
in which
the ring B represents benzo or pyrido, where benzo and pyrido are optionally substituted by 1 to 3 radicals selected from the group consisting of hydrogen, halogen, formyl, carbamoyl, cyano, trifluoromethyl, trifluoromethoxy, nitro, amino, formamido, acetamido, $C_1$-$C_4$-alkyl, $C_1$-$C_4$-alkoxy, $C_1$-$C_4$-alkylthio, $C_1$-$C_4$-alkylamino, furylcarbonylamino, phenylcarbonylamino, methylsulfonylamino, di(phenylsulfonyl)amino, cyclopropylcarbonylmethyl and amino(hydroxyimino)methyl,
and $R^1$, $R^2$, $R^3$ and A are as defined above.

Particularly preferred are compounds of the formula (I),
in which
the ring B represents benzo or pyrido, where benzo and pyrido are optionally substituted by 1 to 3 radicals selected from the group consisting of hydrogen, halogen, cyano, trifluoromethyl, trifluoromethoxy, nitro, amino, formamido, acetamido and ($C_1$-$C_4$)-alkyl,
and $R^1$, $R^2$, $R^3$ and A are as defined above.

Very particular preference is given to compounds of formula (I),
in which
the ring B represents benzo, where benzo is optionally substituted by 1 to 3 radicals selected from the group consisting of hydrogen, halogen, cyano, trifluoromethyl, trifluoromethoxy, nitro, amino, formamido, acetamido and ($C_1$-$C_4$)-alkyl,
and $R^1$, $R^2$, $R^3$ and A are as defined above.

Also particularly preferred are compounds of the formula (Ia),
in which
Z represents hydrogen, halogen, formyl, carbamoyl, cyano, trifluoromethyl, trifluoromethoxy, nitro, amino, formamido, acetamido, methyl, ethyl, methoxy, ethoxy, $C_1$-$C_4$-alkylamino, furylcarbonylamino, phenylcarbonylamino, methylsulfonylamino, di(phenylsulfonyl)amino, cyclopropylcarbonylmethyl or amino(hydroxyimino)methyl,
and $R^1$, $R^2$, $R^3$ and A are as defined above.

Very particular preference is given to combinations of two or more of the preferred ranges mentioned above.

Especially preferred are compounds of the formula (I),
in which
$R^1$ represents (3R)-1-azabicyclo[2.2.2]oct-3-yl,
$R^2$ and $R^3$ represent hydrogen,
A represents sulfur,
and
the ring B represents benzo or pyrido, where benzo and pyrido are optionally substituted by 1 to 3 radicals selected from the group consisting of hydrogen, halogen, cyano, trifluoromethyl, trifluoromethoxy, nitro, amino, formamido, acetamido and ($C_1$-$C_4$)-alkyl.

The invention relates furthermore to a process for preparing the compounds of the formula (I), characterized in that compounds of the formula (II)

$$R^1R^2NH \qquad (II),$$

in which $R^1$ and $R^2$ are as defined above
are reacted with a compound of the formula (III)

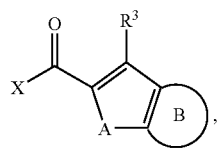

in which

R³, A and the ring B are as defined above, and

X represents hydroxy or a suitable leaving group, in an inert solvent, if appropriate in the presence of a condensing agent and if appropriate in the presence of a base.

If X represents a leaving group, preference is given to chlorine, mesyloxy and isobutyloxycarbonyloxy, in particular to chlorine.

Inert solvents are, for example, halogenated hydrocarbons, such as methylene chloride, trichloromethane, carbon tetrachloride, trichloroethane, tetrachloroethane, 1,2-dichloroethane or trichloroethylene, ethers, such as diethyl ether, methyl tert-butyl ether, dioxane, tetrahydrofuran, glycol dimethyl ether or diethylene glycol dimethyl ether, hydrocarbons, such as benzene, xylene, toluene, hexane, cyclohexane or mineral oil fractions, or other solvents, such as nitromethane, ethyl acetate, acetone, dimethylformamide, dimethylacetamide, 1,2-dimethoxyethane, dimethyl sulfoxide, acetonitrile or pyridine; preference is given to tetrahydrofuran, dimethylformamide or chloroform.

Condensing agents are, for example, carbodiimides, such as, for example, N,N'-diethyl-, N,N,'-dipropyl-, N,N'-diisopropyl-, N,N'-dicyclohexylcarbodiimide, N-(3-dimethylaminoisopropyl)-N'-ethylcarbodiimide hydrochloride (EDC), N-cyclohexylcarbodiimide-N'-propyloxymethyl-polystyrene (PS-carbodiimide), or carbonyl compounds, such as carbonyldiimidazole, or 1,2-oxazolium compounds, such as 2-ethyl-5-phenyl-1,2-oxazolium 3-sulfate or 2-tert-butyl-5-methylisoxazolium perchlorate, or acylamino compounds, such as 2-ethoxy-1-ethoxycarbonyl-1,2-dihydroquinoline, or propanephosphonic anhydride, or isobutyl chloroformate, or bis-(2-oxo-3-oxazolidinyl)phosphoryl chloride or benzotriazolyloxytri(dimethylamino)-phosphonium hexafluorophosphate, or O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU) or O-(7-azabenzotriazol-1-yl)-N,N,N',N'-tetramethyluronium hexafluorophosphate (HATU) or benzotriazol-1-yloxytris(dimethylamino)phosphonium hexafluorophosphate (BOP), or mixtures of these.

If appropriate, it may be advantageous to use these condensing agents in the presence of an auxiliary nucleophile, such as, for example, 1-hydroxybenzotriazole (HOBt).

Bases are, for example, alkali metal carbonates, such as, for example, sodium carbonate or potassium carbonate or sodium bicarbonate or potassium bicarbonate, or organic bases, such as trialkylamines, for example triethylamine, N-methylmorpholine, N-methylpiperidine, 4-N,N-dimethylaminopyridine or N,N-diisopropylethylamine.

Preference is given to O-(7-azabenzotriazol-1-yl)-N,N,N',N'-tetramethyluronium hexafluorophosphate (HATU) in the presence of N,N-diisopropylethylamine and to the combination of N-(3-dimethylaminoisopropyl)-N'-ethylcarbodiimide hydrochloride (EDC) and 1-hydroxybenzotriazole (HOBt), in each case in dimethylformamide.

The process according to the invention is preferably carried out in a temperature range of from room temperature to 50° C., at atmospheric pressure.

The compounds of the formulae (II) and (III) are known or can be synthesized by known processes from the appropriate starting materials (cf., for example, "Comprehensive Heterocyclic Chemistry", Katritzki et al., Ed.; Elsevier, 1996).

Thus, for example, substituted benzothiophene-2-carboxylic acids can be obtained from appropriately substituted 2-halobenzaldehydes by reaction with methyl mercaptoacetate (see, for example, A. J. Bridges, A. Lee, E. C. Maduakor, Schwartz, *Tetrahedron Lett.* 1992, 33, 7499) and subsequent hydrolysis of the ester (synthesis scheme 1):

Synthesis scheme 1:

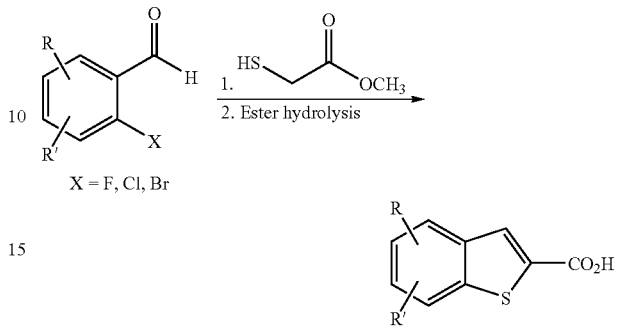

To synthesize the corresponding pyrido derivatives, it is possible to react 2-halo-benzonitrile starting materials with methyl mercaptoacetate to give the 3-aminobenzothiophene-2-carboxylic esters (synthesis scheme 2). The amino function can be removed by diazotization. Finally, the ester is hydrolyzed to give the target compound:

Synthesis scheme 2:

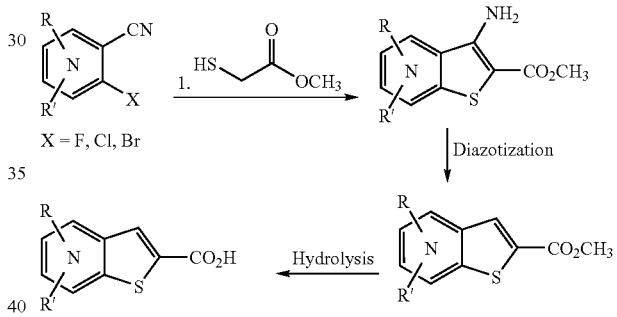

Substituted benzofuran-2-carboxylic acids can be obtained, for example, in accordance with D. Bogdal, M. Warzala, *Tetrahedron* 2000, 56, 8769 (synthesis scheme 3):

Synthesis scheme 3:

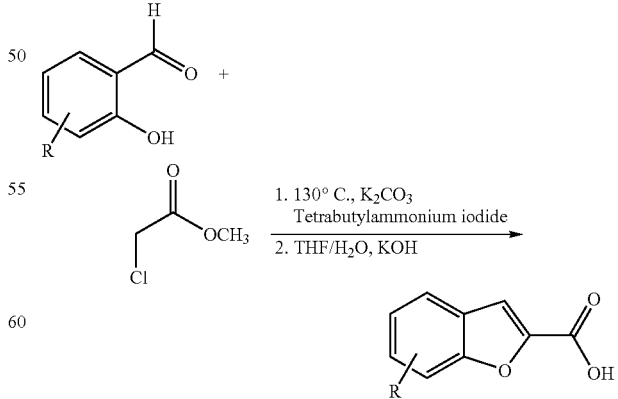

The compounds according to the invention of the formula (I) are suitable for use as medicaments for the treatment and/or prophylaxis of diseases in humans and/or animals.

The compounds according to the invention have an unforeseeable, useful pharmacological activity spectrum.

They act as ligands, in particular as α7-nAChR agonists.

The compounds of the invention can, because of their pharmacological properties, be employed alone or in combination with other active ingredients for the treatment and/or prevention of cognitive impairments, especially of Alzheimer's disease. Because of their selective effect as α7-nAChR agonists, the compounds of the invention are particularly suitable for improving perception, concentration, learning or memory, especially after cognitive impairments like those occurring for example in situations/diseases/syndromes such as mild cognitive impairment, age-associated learning and memory impairments, age-associated memory loss, vascular dementia, craniocerebral trauma, stroke, dementia occurring after strokes (post-stroke dementia), post-traumatic brain syndrome, general concentration impairments, concentration impairments in children with learning and memory problems, attention deficit hyperactivity disorder, Alzheimer's disease, Lewy body dementia, dementia with degeneration of the frontal lobes, including Pick's syndrome, Parkinson's disease, progressive nuclear palsy, dementia with corticobasal degeneration, amyotrophic lateral sclerosis (ALS), Huntington's disease, multiple sclerosis, thalamic degeneration, Creutzfeld-Jakob dementia, HIV dementia, schizophrenia, schizophrenia with dementia or Korsakoffs psychosis.

The compounds of the invention can be employed alone or in combination with other active ingredients for the prophylaxis and treatment of acute and/or chronic pain (for a classification, see "Classification of Chronic Pain, Descriptions of Chronic Pain Syndromes and Definitions of Pain Terms", 2nd edition, Meskey and Begduk, editors; IASP Press, Seattle, 1994), especially for the treatment of cancer-induced pain and chronic neuropathic pain like, for example, that associated with diabetic neuropathy, postherpetic neuralgia, peripheral nerve damage, central pain (for example as a consequence of cerebral ischaemia) and trigeminal neuralgia, and other chronic pain such as, for example, lumbago, backache (low back pain) or rheumatic pain. In addition, these active ingredients are also suitable for the therapy of primary acute pain of any origin and of secondary states of pain resulting therefrom, and for the therapy of states of pain which were formerly acute and have become chronic.

The in vitro effect of the compounds of the invention can be shown in the following assays:

1. Determination of the Affinity of Test Substances for α7-nAChR by inhibition of [$^3$H]-methyllycaconitine Binding to Rat Brain Membranes The [$^3$H]-methyllycaconitine binding assay is a modification of the method described by Davies et al. in *Neuropharmacol.* 1999, 38, 679-690.

Rat brain tissue (hippocampus or whole brain) is homogenized in homogenization buffer (10% w/v, 0.32 M sucrose, 1 mM EDTA, 0.1 mM phenylmethylsulfonyl fluoride (PMSF), 0.01% (w/v) NaN$_3$, pH 7.4, 4° C.) at 600 rpm in a glass homogenizer. The homogenate is centrifuged (1000×g, 4° C., 10 min) and the supernatant is removed. The pellet is resuspended (20% w/v) and the suspension is centrifuged (1000×g, 4° C., 10 min). The two supernatants are combined and centrifuged (15 000×g, 4° C., 30 min). The pellet obtained in this way is referred to as the P2 fraction.

The P2 pellet is washed with binding buffer (50 mM Tris-HCl, 1 mM MgCl$_2$, 120 mM NaCl, 5 mM KCl, 2 mM CaCl$_2$, pH 7.4), and centrifuged (15 000×g, 4° C., 30 min), twice.

The P2 membranes are resuspended in binding buffer and incubated in a volume of 250 μl (amount of membrane protein 0.1-0.5 mg) in the presence of 1-5 nM [$^3$H]-methyllycaconitine, 0.1% (w/v) BSA (bovine serum albumin) and various concentrations of the test substance at 21° C. for 2.5 h. Incubation is then carried out in the presence of 1 μM α-bungarotoxin or 100 μM nicotine or 10 μM MLA (methyllycaconitine) to determine the non-specific binding.

The incubation is stopped by adding 4 ml PBS (20 mM Na$_2$HPO$_4$, 5 mM KH$_2$PO$_4$, 150 mM NaCl, pH 7.4, 4° C.) and filtering through type A/E glass fibre filters (Gelman Sciences) which have previously been placed in 0.3% (v/v) polyethyleneimine (PEI) for 3 h. The filters are washed twice with 4 ml of PBS (4° C.), and the bound radioactivity is determined by scintillation measurement. All the assays are carried out in triplicate. The dissociation constant of the test substance $K_i$ was determined from the IC$_{50}$ of the compounds (concentration of the test substance at which 50% of the ligand bound to the receptor is displaced), the dissociation constant $K_D$ and the concentration L of [$^3$H]-methyllycaconitine using the equation $K_i = IC_{50}/(1+L/K_D)$.

In place of [$^3$H]-methyllycaconitine it is also possible to employ other α7-nAChR-selective radioligands such as, for example, [$^{125}$I]-α-bungarotoxin or nonselective nAChR radioligands together with inhibitors of other nAChRs.

Representative in vitro data for the effects of the compounds of the invention are shown in Table A:

TABLE A

| Example | $K_i$ (nM) |
|---|---|
| 19 | 42.0 |
| 35 | 3.7 |
| 36 | 63.0 |
| 37 | 80.0 |
| 42 | 37.0 |
| 46 | 58.0 |
| 48 | 75.0 |
| 51 | 3.9 |
| 58 | 3.1 |
| 59 | 20.0 |
| 62 | 50.0 |
| 64 | 20.0 |
| 65 | 55.0 |
| 68 | 2.0 |
| 73 | 2.8 |
| 74 | 22.0 |
| 76 | 6.7 |
| 77 | 20.0 |
| 78 | 80.0 |
| 80 | 31.0 |
| 88 | 28.0 |

The suitability of the compounds of the invention for the treatment of cognitive impairments can be shown in the following animal models:

2. Object Recognition Test

The object recognition test is a memory test. It measures the ability of rats (and mice) to distinguish between familiar and unfamiliar objects.

The test is carried out as described by Blokland et al., *NeuroReport* 1998, 9, 4205-4208; A. Ennaceur J. Delacour, *Behav. Brain Res.* 1988, 31, 47-59; A. Ennaceur K. Meliani, *Psychopharmacology* 1992, 109, 321-330; and Prickaerts et al., *Eur. J. Pharmacol.* 1997, 337, 125-136.

In a first run, a rat is confronted in an otherwise empty observation arena of relatively large size by two identical objects. The rat will investigate, i.e. sniff round and touch, both objects extensively. In a second run, after an interval of 24 hours, the rat is put in the observation arena again. One of the familiar objects has now been replaced by a new, unfamiliar object. If a rat recognizes the familiar object, it will concentrate on investigating the unfamiliar object. However, after 24 hours, a rat has normally forgotten which object it investigated in the first run, and it will therefore inspect both objects to the same extent. Administration of a substance with a learning- and memory-improving effect may lead to a rat recognizing the object seen in the first run 24 hours previously as familiar. It will investigate the new, unfamiliar object in more detail than the familiar one. This memory ability is expressed in a discrimination index. A discrimination index of zero means that the rat investigates both objects, the old and the new, for equal times; that is to say it has not recognized the old object and reacts to both objects as if they were new and unfamiliar. A discrimination index greater than zero means that the rat inspects the new object for longer than the old one; that is to say the rat has recognized the old object.

3. Social Recognition Test:

The social recognition test is a test to examine the learning- or memory-improving effect of test substances.

Adult rats housed in groups are placed singly in test cages 30 minutes before the start of the test. Four minutes before the start of the test, the test animal is put in an observation box. After this adaptation time, a juvenile animal is put in with the test animal and the time for which the adult animal investigates the juvenile animal is measured for 2 minutes (trial 1). All behaviours clearly directed at the young animal are measured, i.e. anogenital inspection, pursuit and fur care, during which the old animal is no further than 1 cm from the young animal. The juvenile animal is then taken out, and the adult is left in its test cage (for 24-hour retention, the animal is returned to its home cage). The adult test animal is treated with test substance before or after the first test. Depending on the timing of the treatment, the learning or the storage of the information about the young animal can be influenced by the substance. After a fixed period (retention), the test is repeated (trial 2). A larger difference between the investigation times measured in trials 1 and 2 means that the adult animal has remembered the young animal better.

The compounds of the formula (I) according to the invention are suitable for use as medicaments for humans and animals.

The present invention also includes pharmaceutical preparations which, besides inert, nontoxic, pharmaceutically suitable excipients and carriers, contain one or more compounds of the formula (I), or which consist of one or more compounds of the formula (I), and processes for producing these preparations.

The compounds of the formula (I) are to be present in these preparations in a concentration of from 0.1 to 99.5% by weight, preferably from 0.5 to 95% by weight, of the complete mixture.

Besides the compounds of the formula (I), the pharmaceutical preparations may also contain other active pharmaceutical ingredients.

The abovementioned pharmaceutical preparations can be produced by known methods in a conventional way using, for example, the auxiliary or auxiliaries or excipient(s).

The novel active ingredients can be converted in a known manner into conventional formulations such as tablets, coated tablets, pills, granules, aerosols, syrups, emulsions, suspensions and solutions, using inert, nontoxic, pharmaceutically suitable excipients or solvents. In these cases, the therapeutically active compound should in each case be present in a concentration of about 0.5 to 90% by weight of the entire mixture, i.e. in amounts which are sufficient to reach the stated dose range.

The formulations are produced for example by extending the active ingredients with solvents and/or excipients, where appropriate with use of emulsifiers and/or dispersants, it being possible for example when water is used as diluent where appropriate to use organic solvents as auxiliary solvents.

Administration takes place in a conventional way, preferably orally, transdermally or parenterally, especially perlingually or intravenously. However, it can also take place by inhalation through the mouth or nose, for example with the aid of a spray, or topically via the skin.

It has generally proved advantageous to administer amounts of about 0.001 to 10 mg/kg, on oral administration preferably about 0.005 to 3 mg/kg, of body weight to achieve effective results.

It may, nevertheless, be necessary where appropriate to deviate from the stated amounts, in particular as a function of the body weight or of the mode of administration, of the individual behaviour toward the medicament, the nature of its formulation and the time or interval over which administration takes place. Thus, it may be sufficient in some cases to make do with less than the aforementioned minimum amount, whereas in other cases the stated upper limit must be exceeded. Where larger amounts are administered, it may be advisable to divide these into a plurality of single doses over the day.

| Abbreviations: | |
|---|---|
| BINAP | 2,2'-Bis(diphenylphosphino)-1,1'-binaphthyl |
| DCI | direct chemical ionization (in MS) |
| DMF | N,N-Dimethylformamide |
| DMSO | Dimethyl sulfoxide |
| EDC | N'-(3-Dimethylaminopropyl)-N-ethylcarbodiimide × HCl |
| EDTA | Ethylenediaminetetraacetic acid |
| eq. | Equivalent(s) |
| ESI | Electrospray ionization (in MS) |
| HATU | O-(7-Azabenzotriazol-1-yl)-N,N,N',N'-tetramethyluronium hexafluorophosphate |
| HOBt | 1-Hydroxy-1H-benzotriazole × $H_2O$ |
| HPLC | High pressure/high performance liquid chromatography |
| LC-MS | Liquid chromatography with coupled mass spectroscopy |
| MS | Mass spectroscopy |
| NMR | Nuclear magnetic resonance spectroscopy |
| $Pd_2(dba)_3$ | Tris(dibenzylideneacetone)dipalladium(0) |
| RT | Room temperature, 20° C. |
| $R_t$ | Retention time (in HPLC) |
| TBTU | O-(Benzotriazol-1-yl)-N,N,N',N'-tetramethyluronium tetrafluoroborate |
| TFA | Trifluoroacetic acid |
| THF | Tetrahydrofuran |
| Tris | Tris(hydroxymethyl)aminomethane |

LC-MS Method A:

| MS instrument: | Micromass Quattro LCZ Ionization: ESI positive | | | |
|---|---|---|---|---|
| HPLC instrument: | HP 1100 UV detector DAD: 208-400 nm Oven temperature: 40° C. | | | |
| Column: | Symmetry C 18 50 mm × 2.1 mm; 3.5 µm | | | |
| Gradient: | Time (min) | A: % | B: % | Flow rate (ml/min) |
| | 0.00 | 10.0 | 90.0 | 0.50 |
| | 4.00 | 90.0 | 10.0 | 0.50 |
| | 6.00 | 90.0 | 10.0 | 0.50 |
| | 6.10 | 10.0 | 90.0 | 1.00 |
| | 7.50 | 10.0 | 90.0 | 0.50 |

A: Acetonitrile + 0.1% formic acid
B: Water + 0.1% formic acid

LC-MS Method B:

| MS instrument: | Finnigan MAT 900S Ionization: ESI positive | | | |
|---|---|---|---|---|
| HPLC instrument: | TSP: P4000, AS3000, UV3000HR UV detector 3000HR: 210 nm Oven temperature: 70° C. | | | |
| Column: | Symmetry C 18 150 mm × 2.1 mm; 5 µm | | | |
| Supplier: | Waters | | | |
| | Time (min) | A: % | B: % | C: % | Flow rate (ml/min) |
| Gradient: | 0 | 2 | 49 | 49 | 0.9 |
| | 2.5 | 95 | 2.5 | 2.5 | 1.2 |
| | 5 | 95 | 2.5 | 2.5 | 1.2 |
| | 5.5 | 2 | 49 | 49 | 1.2 |
| | 6.5 | 2 | 49 | 49 | 1.2 |
| | 7 | 2 | 49 | 49 | 0.9 |

A: Acetonitrile
B: Water + 0.6 g/l 35% strength hydrochloric acid
C: Water

LC-MS Method C:

| MS instrument: | Micromass Platform LCZ Ionization: ESI positive | | | |
|---|---|---|---|---|
| HPLC instrument: | HP 1100 UV detector DAD: 208-400 nm Oven temperature: 40° C. | | | |
| Column: | Symmetry C 18 50 mm × 2.1 mm; 3.5 µm | | | |
| Gradient | Time (min) | A: % | B: % | Flow rate (ml/min) |
| | 0.00 | 10.0 | 90.0 | 0.50 |
| | 4.00 | 90.0 | 10.0 | 0.50 |
| | 6.00 | 90.0 | 10.0 | 0.50 |
| | 6.10 | 10.0 | 90.0 | 1.00 |
| | 7.50 | 10.0 | 90.0 | 0.50 |

A: Acetonitrile + 0.1% formic acid
B: Water + 0.1% formic acid

LC-MS Method D:
Instrument: Micromass Platform LCZ, HP1100; Column: Symmetry C18, 50 mm×2.1 mm, 3.5 µm; Mobile phase A: water+0.05% formic acid, mobile phase B: acetonitrile+0.05% formic acid; Gradient: 0.0 min 90% A→4.0 min 10% A→6.0 min 10% A; Oven: 40° C.; Flow rate: 0.5 ml/min; UV detection: 208-400 nm.

LC-MS Method E:
Instrument: Micromass Quattro LCZ, HP1100; Column: Uptisphere HDO, 50 mm×2.0 mm, 3 µm; Mobile phase A: water+0.05% formic acid, mobile phase B: acetonitrile+0.05% formic acid; Gradient: 0.0 min 100% A→0.2 min 100% A→2.9 min 30% A→3.1 min 10% A→4.5 min 10% A; Oven: 55° C.; Flow rate: 0.8 ml/min; UV detection: 208-400 nm.

LC-MS Method F:
Instrument: Micromass Quattro LCZ, HP1100; Column: Symmetry C18, 50 mm×2.1 mm, 3.5 µm; Mobile phase A: water+0.05% formic acid, mobile phase B: acetonitrile+0.05% formic acid; Gradient: 0.0 min 90% A→4.0 min 10% A→6.0 min 10% A; Oven: 40° C.; Flow rate: 0.5 ml/min; UV detection: 208-400 nm.

LC-MS Method G:
MS instrument: Micromass ZQ; HPLC instrument: Waters Alliance 2790; Column: Uptisphere C18, 50 mm×2.0 mm, 3.0 µm; Mobile phase A: acetonitrile+0.05% formic acid, mobile phase B: water+0.05% formic acid; Gradient: 0.0 min 5% A→2.0 min 40% A→4.5 min 90% A→5.5 min 90% A; Oven: 45° C.; Flow rate: 0.0 min 0.75 ml/min→4.5 min 0.75 ml/min→5.5 min 1.25 ml/min; UV detection: 210 nm.

HPLC Method H:
Instrument: HP 1100 with DAD detection; column: Kromasil RP-18, 60 mm×2 mm, 3.5 µm; mobile phase A: 5 ml HClO$_4$/l H$_2$O, mobile phase B: acetonitrile; Gradient: 0 min 2% B, 0.5 min 2% B, 4.5 min 90% B, 6.5 min 90% B; Flow rate: 0.75 ml/min; Temperature: 30° C.; UV detection: 210 nm.

Starting Materials:

General reaction scheme for the synthesis of methyl 1-benzothiophene-2-carboxylates:

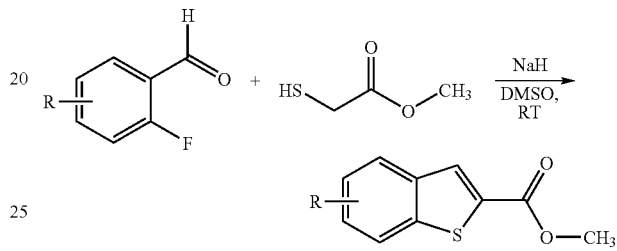

General Procedure for the Synthesis of methyl 1-benzothiophene-2-carboxylates:

Under an argon atmosphere, 1.5 equivalents of sodium hydride (60% pure) are initially charged in absolute DMSO (0.60-1.26 M suspension). At room temperature, 1.1 equivalents of methyl mercaptoacetate are slowly added dropwise to the reaction mixture, and it is left to stir at room temperature until evolution of hydrogen ceases (about 15 min). 1.0 equivalents of the appropriate benzaldehyde are dissolved in absolute DMSO (1.60-3.36 M solution) and added at room temperature to the reaction mixture. The reaction mixture is stirred until the reaction is complete (about 5-10 min) and then poured into ice-water. The resulting precipitate is filtered off with suction, dried at 40° C. under reduced pressure overnight and reacted further as crude product.

General Reaction Scheme for the Synthesis of 1-benzothiophene-2-carboxylic acids:

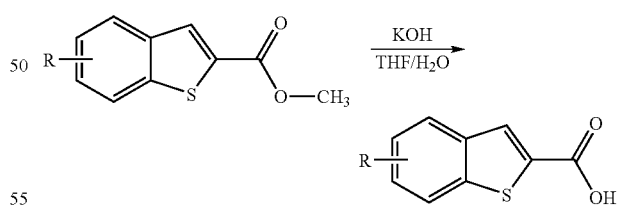

General Procedure for the Synthesis of 1-benzothiophene-2-carboxylic acids:

A mixture of equal parts of THF and 2 N potassium hydroxide solution (0.28-0.47 M solution) is added to the appropriate methyl 1-benzothiophene-2-carboxylate. The reaction mixture is left to stir at room temperature overnight. The THF is removed under reduced pressure and the aqueous reaction mixture is acidified with concentrated hydrochloric acid. The resulting precipitate is filtered off with suction and dried under reduced pressure at 40° C.

General Procedure for Amide Linkage Between 3-quinuclidinamine and 2-benzothiophene- or 2-benzofurancarboxylic acids (Variant A):

1.5 eq. of the appropriate enantiomeric 3-quinuclidinamine hydrochloride are, together with 1 eq. of the carboxylic acid and 1.5 eq. of HATU, initially charged in DMF at 0° C. After addition of 1.5 eq. of N,N-diisopropylethylamine, the mixture is stirred for 30 min. A further 4 eq. of N,N-diisopropylethylamine are added, and the mixture is stirred at RT overnight. Purification is carried out chromatographically.

General Procedure for Amide Linkage Between 3-quinuclidinamine and 2-benzothiophene- or 2-benzofurancarboxylic acids (Variant B):

1.0 eq. of the appropriate enantiomeric 3-quinuclidinamine dihydrochloride are, together with 1 eq. of the carboxylic acid and 1.2 eq. of HATU, initially charged in DMF at 0° C. After addition of 1.2 eq. of N,N-diisopropylethylamine, the mixture is stirred for 30 min. A further 2.4 eq. of N,N-diisopropylethylamine are added, and the mixture is stirred at RT overnight. Purification is carried out chromatographically.

General Procedure for the Synthesis of methyl 3-aminothienopyridine-2-carboxylates:

1.0 equivalents of the appropriate pyridine derivative are dissolved in absolute DMSO (0.93-0.96 M solution), and 2 equivalents of triethylamine are added. After addition of 1 equivalent of methyl mercaptoacetate, the reaction mixture is stirred at 60° C. overnight. The reaction mixture is poured into ice-water and stirred therein. The precipitated solid is filtered off with suction and, if required, purified by column chromatography (silica gel 60, mobile phase toluene/ethyl acetate 20:1 to 5:1).

General Procedure for the Synthesis of methyl thienopyridine-2-carboxylates:

With cooling at −5° C., 1.0 equivalents of the appropriate methyl 3-aminothienopyridine-2-carboxylate is initially charged in 75% strength sulfuric acid (0.33-0.36 M solution). A solution of 3.2 equivalents of sodium nitrite in water (0.92-1.00 M solution) is slowly added dropwise to the reaction mixture such that the temperature of the reaction mixture does not exceed 0° C. The mixture is stirred at 0° C. for 45 min. 60-65 equivalents of ice-cold 50% strength hypophosphoric acid are then added dropwise to the reaction mixture, again in such a way that the temperature does not exceed 0° C. The reaction mixture is stirred at −5° C. for one hour and then kept in the fridge overnight. The reaction mixture is diluted with sodium bicarbonate solution and ethyl acetate, and sodium bicarbonate is added a little at a time until the mixture gives a basic reaction. Work-up is described in the examples below.

General Procedure for the Synthesis of thienopyridine-2-carboxylic acids:

A mixture of equal parts of THF and 2 N potassium hydroxide solution (0.22 M solution) is added to the appropriate methyl thienopyridine-2-carboxylate. The reaction mixture is stirred at room temperature overnight. The reaction mixture is diluted with water, washed twice with ethyl acetate and acidified with concentrated hydrochloric acid. Work-up is described in the examples below.

EXAMPLE 1A

Methyl 6-fluoro-1-benzothiophene-2-carboxylate

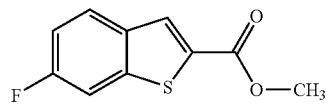

Using 2.00 g (14.07 mmol) of 2,4-difluorobenzaldehyde, 0.84 g (21.11 mmol) of sodium hydride (60% pure) and 1.64 g (15.48 mmol) of methyl mercaptoacetate, 1.99 g of the desired product are obtained. The product is obtained in a purity which permits further reaction and is reacted without further purification.

MS (EIpos): m/z=210 (M)$^+$.

EXAMPLE 2A

Methyl 5-bromo-1-benzothiophene-2-carboxylate

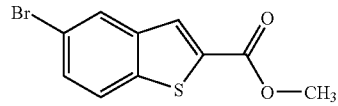

1.62 g (8.00 mmol) of 5-bromo-2-fluorobenzaldehyde, 0.48 g (12.00 mmol) of sodium hydride (60% pure) and 0.93 g (8.80 mmol) of methyl mercaptoacetate give 1.53 g (71% of theory) of the desired product.

LC-MS (Method A): R$_t$=4.80 min.

MS (EIpos): m/z=272 (M)$^+$ $^1$H NMR (200 MHz, CDCl$_3$): δ=8.07-7.92 (m, 2H), 7.78-7.66 (m, 1H), 7.59-7.48 (m, 1H), 3.95 (s, 3H).

EXAMPLE 3A

Methyl 5-methyl-1-benzothiophene-2-carboxylate

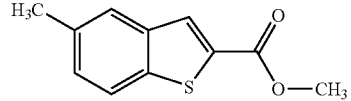

2.32 g (16.78 mmol) of 2-fluoro-5-methylbenzaldehyde, 1.01 g (25.17 mmol) of sodium hydride (60% pure) and 1.96 g (18.46 mmol) of methyl mercaptoacetate give 1.96 g (57% of theory) of the desired product.

LC-MS (Method C): R$_t$=4.68 min.

MS (EIpos): m/z=206 (M)$^+$ $^1$H NMR (200 MHz, CDCl$_3$): δ=7.99 (s, 1H), 7.79-7.64 (m, 2H), 7.34-7.23 (m, 1H), 3.94 (s, 3H).

EXAMPLE 4A

6-Fluoro-1-benzothiophene-2-carboxylic acid

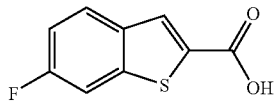

1.99 g (9.46 mmol) of methyl 6-fluoro-1-benzothiophene-2-carboxylate give 1.43 g of the desired product. The product is obtained in a purity which permits further reaction and is reacted without further purification.

MS (EIpos): m/z=196 (M)$^+$.

EXAMPLE 5A

5-Bromo-1-benzothiophene-2-carboxylic acid

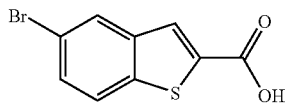

1.53 g (5.64 mmol) of methyl 5-bromo-1-benzothiophene-2-carboxylate give 1.31 g (90% of theory) of the desired product.

HPLC (Method H): $R_t$=4.50 min.
MS (ESIneg): m/z=255 (M−H)$^−$
$^1$H NMR (200 MHz, CDCl$_3$): δ=8.01 (d, 1H), 7.94 (s, 1H), 7.74 (d, 1H), 7.53 (dd, 1H).

EXAMPLE 6A

5-Methyl-1-benzothiophene-2-carboxylic acid

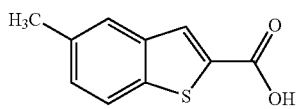

1.96 g (9.49 mmol) of methyl 5-methyl-1-benzothiophene-2-carboxylate give 1.46 g (80% of theory) of the desired product.

HPLC (Method H): $R_t$=4.38 min.
MS (DCI): m/z=210 (M+NH$_4$)$^+$
$^1$H NMR (200 MHz, CDCl$_3$): δ=8.09 (s, 1H), 7.65-7.83 (m, 2H), 7.39-7.29 (m, 1H), 2.49 (s, 3H).

EXAMPLE 7A

Methyl 3-aminothieno[2,3-b]pyridine-2-carboxylate

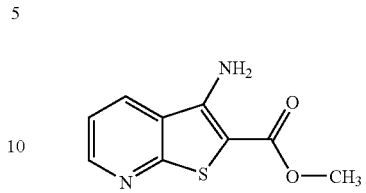

0.92 g (6.51 mmol) of 2-chloronicotinonitrile, 1.37 g (13.53 mmol) of triethylamine and 0.72 g (6.77 mmol) of methyl mercaptoacetate give 0.22 g (16% of theory) of the desired product.

HPLC (Method H): $R_t$=3.56 min.
MS (ESIpos): m/z=209 (M+H)$^+$
$^1$H NMR (300 MHz, CDCl$_3$): δ=8.76-8.62 (m, 1H), 7.99-7.87 (m, 1H), 7.37-7.28 (m, 1H), 5.91 (br. s, 2H), 3.91 (s, 3H).

EXAMPLE 8A

Methyl 3-aminothieno[3,2-b]pyridine-2-carboxylate

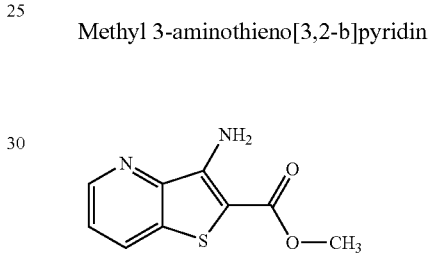

2.00 g (14.43 mmol) of 2-chloro-2-pyridinecarbonitrile, 3.03 g (30.02 mmol) of triethylamine and 1.59 g (15.01 mmol) of methyl mercaptoacetate give 2.47 g (81% of theory) of the desired product.

LC-MS (Method A): $R_t$=3.4 min.
MS (ESIpos): m/z=209 (M+H)$^+$
$^1$H NMR (300 MHz, CDCl$_3$): δ=8.67-8.58 (m, 1H), 8.10-8.01 (m, 1H), 7.42-7.33 (m, 1H), 6.22 (br. s, 2H), 3.92 (s, 3H).

EXAMPLE 9A

Methyl thieno[2,3-b]pyridine-2-carboxylate

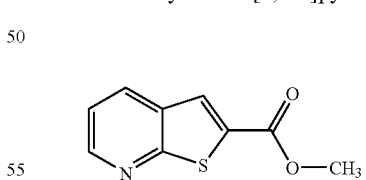

The synthesis is carried out according to the general procedure; for work-up, the resulting precipitate is filtered off with suction and washed twice with water and three times with ethyl acetate. The organic phase of the resulting filtrate is separated off, dried and concentrated. Using 0.22 g (1.07 mmol) of methyl 3-aminothieno[2,3-b]pyridine-2-carboxylate and 0.24 g (3.41 mmol) of sodium nitrite, 84 mg (41% of theory) of the desired product are obtained.

LC-MS (Method A): $R_t$=3.34 min.
MS (ESIpos): m/z=194 (M+H)$^+$ $^1$H NMR (200 MHz, CDCl$_3$): δ=8.82-8.66 (m, 1H), 8.53-8.38 (m, 1H), 8.23 (s, 1H), 7.63-7.48 (m, 1H), 3.92 (s, 3H).

EXAMPLE 10A

Methyl thieno[3,2-b]pyridine-2-carboxylate

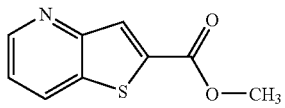

The synthesis is carried out according to the general procedure; for work-up, the resulting precipitate is filtered off with suction and washed repeatedly with water, ethyl acetate and THF. The organic phases of the resulting filtrates are separated off, the aqueous phase is washed with ethyl acetate and the combined organic phases are dried and concentrated. The resulting product is purified by preparative HPLC. Using 2.40 g (11.53 mmol) of methyl 3-aminothieno[3,2-b]pyridine-2-carboxylate and 2.54 g (36.88 mmol) of sodium nitrite, 0.12 g (5% of theory) of the desired product are obtained.

LC-MS (Method C): R$_t$=3.18 min.
MS (ESIpos): m/z=194 (M+H)$^+$
$^1$H NMR (400 MHz, CDCl$_3$): δ=8.83-8.76 (m, 1H), 8.63-8.56 (m, 1H), 8.21 (s, 1H), 7.58-7.50 (m, 1H), 3.93 (s, 3H).

EXAMPLE 11A

Thieno[2,3-b]pyridine-2-carboxylic acid

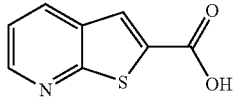

The synthesis is carried out according to the general procedure; for work-up, the aqueous phase is extracted twice with ethyl acetate, the combined organic phases are washed with saturated sodium chloride solution and the solvent is removed under reduced pressure. Using 84 mg (0.43 mmol) of methyl thieno[2,3-b]pyridine-2-carboxylate, 49 mg (63% of theory) of the desired product are obtained.

LC-MS (Method C): R$_t$=2.46 min.
MS (ESIpos): m/z=180 (M+H)$^+$
$^1$H NMR (200 MHz, CDCl$_3$): δ=13.76 (br. s, 1H), 8.80-8.63 (m, 1H), 8.50-8.34 (m, 1H), 8.11 (s, 1H), 7.61-7.47 (m, 1H).

EXAMPLE 12A

Thieno[3,2-b]pyridine-2-carboxylic acid

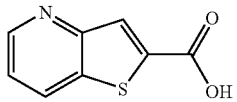

The synthesis is carried out according to the general procedure; for work-up, the precipitated solid is filtered off with suction, washed with water and acetonitrile and dried under reduced pressure. Using 115 mg (0.60 mmol) of methyl thieno[3,2-b]pyridine-2-carboxylate, 77 mg (72% of theory) of the desired product are obtained.

HPLC (Method H): R$_t$=2.08 min.
MS (ESIpos): m/z=180 (M+H)$^+$
$^1$H NMR (400 MHz, D$_2$O): δ=8.63 (d, 1H), 8.39 (d, 1H), 7.85 (s, 1H), 7.45 (dd, 1H).

EXAMPLE 13A

Methyl 7-bromo-1-benzothiophene-2-carboxylate

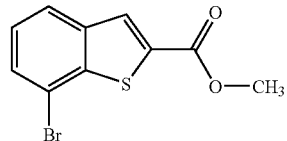

Using 27.8 g (137.1 mmol) of 3-bromo-2-fluorobenzaldehyde, 8.2 g (205.7 mmol) of sodium hydride (60% pure) and 16.0 g (150.9 mmol) of methyl mercaptoacetate, 20.57 g of a mixture of the title compound and the corresponding acid (about 1:1) are obtained.

EXAMPLE 14A

Methyl thieno[2,3-f][1,3]benzodioxole-6-carboxylate

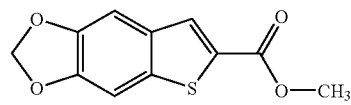

Using 3.0 g (13.1 mmol) of 6-bromopiperonal, 0.79 g (19.7 mmol) of sodium hydride (60% pure) and 1.53 g (14.4 mmol) of methyl mercaptoacetate, 732 mg (18.5% of theory) of the title compound are obtained.

$^1$H NMR (200 MHz, DMSO-d$_6$): δ=8.03 (s, 1H), 7.62 (s, 1H), 7.48 (s, 1H), 6.14 (s, 2H), 3.86 (s, 3H) ppm.
HPLC: R$_t$=4.6 min (Method H)
MS (ESIpos): m/z=237 (M+H)$^+$

EXAMPLE 15A

Methyl 6-cyano-1-benzothiophene-2-carboxylate

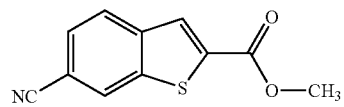

4.08 g (23.2 mmol) of 4-cyano-2-nitrobenzaldehyde, 2.46 g (23.2 mmol) of methyl mercaptoacetate and 6.46 ml (46.4 mmol) of triethylamine in 12.3 ml of DMSO are heated at 80° C. for 2.5 h. The reaction solution is poured into 400 ml of ice-water. After addition of 4 ml of acetic acid, the resulting precipitate is filtered off with suction, washed twice with water and dried at 50° C. under reduced pressure overnight. This gives 4.19 g (83.2% of theory) of the title compound.

¹H NMR (200 MHz, DMSO-d₆): δ=8.73 (d, 1H), 8.32 (s, 1H), 8.21 (d, 1H), 7.85 (dd, 1H), 3.92 (s, 3H) ppm.
HPLC: $R_t$=4.4 min (Method H)
MS (ESIpos): m/z=218 (M+H)⁺

EXAMPLE 16A

Methyl 7-fluoro-1-benzothiophene-2-carboxylate

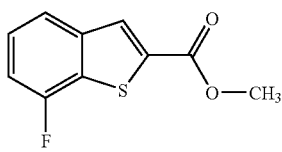

5.0 g (35.2 mmol) of 2,3-difluorobenzaldehyde, 2.11 g (52.8 mmol) of sodium hydride (60% pure) and 4.11 g (38.7 mmol) of methyl mercaptoacetate give 3.30 g (44.6% of theory) of the title compound.
¹H NMR (400 MHz, DMSO-d₆): δ=8.33 (d, 1H), 7.92 (d, 1H), 7.55 (m, 1H), 7.46 (dd, 1H), 3.93 (s, 3H) ppm.
HPLC: $R_t$=4.7 min (Method H)
MS (ESIpos): m/z=228 (M+NH₄)⁺

EXAMPLE 17A

Methyl 7-methoxy-1-benzothiophene-2-carboxylate

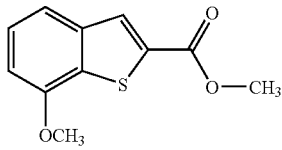

550 mg (3.97 mmol) of potassium carbonate and 350 mg (3.31 mmol) of methyl mercaptoacetate are added to a solution of 600 mg (3.31 mmol) of 3-methoxy-2-nitrobenzaldehyde in 8 ml of DMF. The reaction mixture is heated at 70° C. for 4 h. After cooling, water is added. The resulting precipitate is filtered off, washed with water and dried under reduced pressure. This gives 387 mg (45.7% of theory) of the title compound.
¹H NMR (200 MHz, DMSO-d₆): δ=8.21 (s, 1H), 7.63 (d, 1H), 7.46 (dd, 1H), 7.11 (d, 1H), 3.98 (s, 3H), 3.89 (s, 3H) ppm.
MS (ESIpos): m/z=240 (M+NH₄)⁺

EXAMPLE 18A

Methyl 6-nitro-1-benzothiophene-2-carboxylate

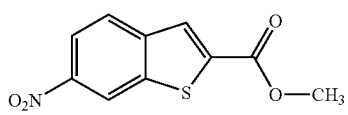

24.8 g (126.7 mmol) of 2,4-dinitrobenzaldehyde, 13.4 g (126.7 mmol) of methyl mercaptoacetate and 35.3 ml (253.3 mmol) of triethylamine in 74.5 ml of DMSO are heated at 80° C. for 1 h. The reaction solution is poured into 250 ml of ice-water. The resulting precipitate is filtered off with suction, washed with water and dried at 50° C. under reduced pressure overnight. This gives 16.1 g (53.6% of theory) of the title compound.
¹H NMR (300 MHz, CDCl₃): δ=8.80 (d, 1H), 8.26 (dd, 1H), 8.12 (s, 1H), 8.00 (d, 1H), 3.99 (s, 3H) ppm.
HPLC: $R_t$=4.7 min (Method H)
MS (ESIpos): m/z=255 (M+NH₄)⁺

EXAMPLE 19A

Methyl 4-nitro-1-benzothiophene-2-carboxylate

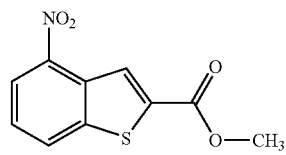

1.0 g (5.10 mmol) of 2,6-dinitrobenzaldehyde, 0.54 g (5.10 mmol) of methyl mercaptoacetate and 1.42 ml (10.20 mmol) of triethylamine in 3 ml of DMSO are heated at 80° C. for 3.5 h. The reaction solution is poured into 100 ml of ice-water. The resulting precipitate is filtered off with suction, washed with water and dried at 50° C. under reduced pressure overnight. This gives 1.10 g (88.7% of theory) of the title compound.
¹H NMR (200 MHz, DMSO-d₆): δ=8.63 (s, 1H), 8.61 (d, 1H), 8.45 (d, 1H), 7.80 (dd, 1H), 3.97 (s, 3H) ppm.
HPLC: $R_t$=4.6 min (Method H)
MS (ESIpos): m/z=238 (M+NH₄)⁺

EXAMPLE 20A

Methyl 6-bromo-1-benzothiophene-2-carboxylate

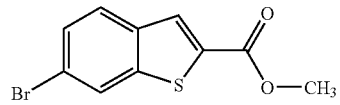

Using 6.54 g (32.2 mmol) of 4-bromo-2-fluorobenzaldehyde, 1.93 g (48.3 mmol) of sodium hydride (60% pure) and 3.76 g (35.5 mmol) of methyl mercaptoacetate, 4.06 g (46.4% of theory) of the title compound are obtained.
¹H NMR (200 MHz, DMSO-d₆): δ=8.42 (d, 1H), 8.22 (s, 1H), 7.98 (d, 1H), 7.65 (dd, 1H), 3.90 (s, 3H) ppm.
HPLC: $R_t$=5.3 min (Method H)
MS (ESIpos): m/z=270 (M⁺), 288 (M+NH₄)⁺

EXAMPLE 21A

Methyl 7-trifluoromethyl-1-benzothiophene-2-carboxylate

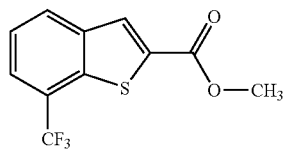

Using 5.0 g (26.0 mmol) of 2-fluoro-3-trifluoromethylbenzaldehyde, 1.56 g (39.0 mmol) of sodium hydride (60% pure) and 3.0 g (28.6 mmol) of methyl mercaptoacetate, 5.4 g (79.7% of theory) of the title compound are obtained.

$^1$H NMR (200 MHz, DMSO-$d_6$): δ=8.40 (s, 1H), 8.38 (m, 1H), 8.00 (d, 1H), 7.73 (dd, 1H), 3.92 (s, 3H) ppm.

HPLC: $R_t$=5.1 min (Method H)

MS (ESIpos): m/z=260 (M$^+$)

EXAMPLE 22A

Methyl 5-trifluoromethyl-1-benzothiophene-2-carboxylate

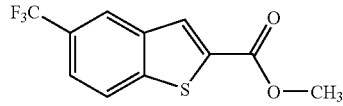

Using 4.28 g (22.3 mmol) of 2-fluoro-5-trifluoromethyl-benzaldehyde, 1.34 g (33.4 mmol) of sodium hydride (60% pure) and 2.6 g (24.5 mmol) of methyl mercaptoacetate, 4.93 g (80.0% of theory) of the title compound are obtained.

$^1$H NMR (200 MHz, DMSO-$d_6$): δ=8.48 (s, 1H), 8.37 (s, 1H), 8.33 (d, 1H), 7.82 (m, 1H), 3.93 (s, 3H) ppm.

MS (ESIpos): m/z=260 (M$^+$)

EXAMPLE 23A

Methyl 7-chloro-1-benzothiophene-2-carboxylate

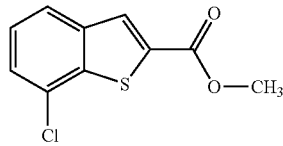

Using 1.0 g (6.31 mmol) of 2-fluoro-3-chlorobenzaldehyde, 0.38 g (9.46 mmol) of sodium hydride (60% pure) and 0.74 g (6.94 mmol) of methyl mercaptoacetate, 1.04 g (72.3% of theory) of the title compound are obtained.

$^1$H NMR (200 MHz, DMSO-$d_6$): δ=8.34 (s, 1H), 8.06 (dd, 1H), 7.70 (dd, 1H), 7.56 (dd, 1H), 3.92 (s, 3H) ppm.

HPLC: $R_t$=4.9 min (Method H)

MS (ESIpos): m/z=227 (M+H)$^+$

EXAMPLE 24A

Methyl 5-fluoro-1-benzothiophene-2-carboxylate

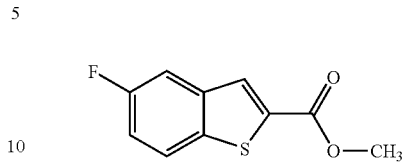

Using 5.0 g (35.2 mmol) of 2,5-difluorobenzaldehyde, 2.11 g (52.78 mmol) of sodium hydride (60% pure) and 4.11 g (38.7 mmol) of methyl mercaptoacetate, 1.1 g (14.3% of theory) of the title compound are obtained.

$^1$H NMR (200 MHz, CDCl$_3$): δ=8.02 (s, 1H), 7.82 (dd, 1H), 7.53 (dd, 1H), 7.23 (ddd, 1H), 3.96 (s, 3H) ppm.

HPLC: $R_t$=4.8 min (Method H)

MS (ESIpos): m/z=210 (M$^+$)

EXAMPLE 25A

Methyl 4-fluoro-1-benzothiophene-2-carboxylate

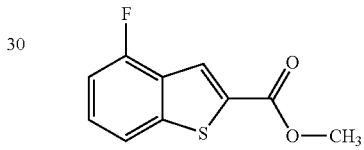

Using 5.0 g (35.2 mmol) of 2,6-difluorobenzaldehyde, 2.11 g (52.8 mmol) of sodium hydride (60% pure) and 4.11 g (38.7 mmol) of methyl mercaptoacetate, 5.61 g (72.8% of theory) of the title compound are obtained.

$^1$H NMR (200 MHz, DMSO-$d_6$): δ=8.16 (s, 1H), 7.95 (d, 1H), 7.59 (ddd, 1H), 7.32 (dd, 1H), 3.91 (s, 3H) ppm.

MS (ESIpos): m/z=210 (M$^+$)

EXAMPLE 26A

Methyl 5,7-difluoro-1-benzothiophene-2-carboxylate

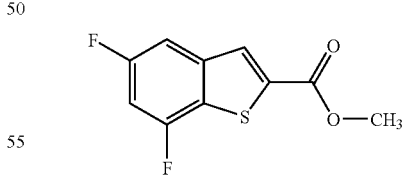

Using 3.94 g (24.6 mmol) of 2,3,5-trifluorobenzaldehyde, 1.48 g (36.9 mmol) of sodium hydride (60% pure) and 2.88 g (27.1 mmol) of methyl mercaptoacetate, 3.58 g (56% of theory) of the title compound are obtained in a purity of 89%. Recrystallization from methanol gives the product in a purity of 97%.

$^1$H NMR (200 MHz, DMSO-$d_6$): δ=8.28 (d, 1H), 7.81 (dd, 1H), 7.61 (m, 1H), 3.93 (s, 3H) ppm.

MS (ESIpos): m/z=228 (M$^+$)

EXAMPLE 27A

Methyl 6-methoxy-1-benzothiophene-2-carboxylate

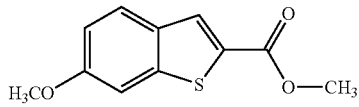

Using 2.5 g (16.2 mmol) of 2-fluoro-4-methoxybenzaldehyde, 0.97 g (24.3 mmol) of sodium hydride (60% pure) and 1.89 g (17.8 mmol) of methyl mercaptoacetate, 3.05 g (84.7% of theory) of the title compound are obtained.

$^1$H NMR (200 MHz, DMSO-$d_6$): δ=8.12 (s, 1H), 7.91 (d, 1H), 7.64 (d, 1H), 7.09 (dd, 1H), 3.88 (s, 3H), 3.87 (s, 3H) ppm.

HPLC: $R_t$=4.7 min (Method H)

MS (ESIpos): m/z=223 (M+H)$^+$, 240 (M+NH$_4$)$^+$

EXAMPLE 28A

Methyl 6-cyano-1-benzothiophene-2-carboxylate

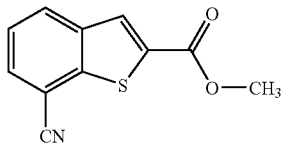

2.5 g (15.1 mmol) of 2-chloro-3-cyanobenzaldehyde are reacted according to the general procedure with 0.90 g (22.7 mmol) of sodium hydride (60% pure) and 1.76 g (16.6 mmol) of methyl mercaptoacetate. The resulting reaction product is initially purified by silica gel column chromatography (mobile phase: dichloromethane/methanol 100:1) and then dissolved in 30 ml of pyridine, and 650 µl (8.4 mmol) of methanesulfonyl chloride are added. The mixture is stirred at 80° C. for 2 h. After cooling, ethyl acetate is added and the mixture is washed twice with 1N hydrochloric acid and once with saturated sodium chloride solution, dried over sodium sulfate, concentrated and dried under high vacuum. This gives 1.63 g (49.9% of theory) of the title compound.

$^1$H NMR (400 MHz, DMSO-$d_6$): δ=8.40 (d, 1H), 8.39 (s, 1H), 8.16 (d, 1H), 7.70 (dd, 1H), 3.94 (s, 3H) ppm.

HPLC: $R_t$=4.3 min (Method H)

MS (ESIpos): m/z=218 (M+H$^+$)

EXAMPLE 29A (2-Chloro-3-nitrophenyl)methanol

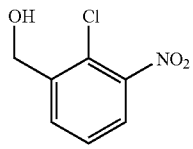

10.0 g (49.61 mmol) of 2-chloro-3-nitrobenzoic acid are initially charged in 50 ml of THF. With ice cooling, 104 ml of 1M borane/THF complex are added, and the mixture is stirred at RT overnight. At 0° C., the mixture is carefully hydrolyzed using water. After the evolution of gas has ceased, the mixture is diluted with 500 ml of water and the aqueous phase is extracted three times with in total 500 ml of ethyl acetate. The organic phase is washed with saturated sodium chloride solution and dried over magnesium sulfate. The solvent is then removed under reduced pressure using a rotary evaporator. This gives 9.20 g (98% of theory) of the title compound.

$^1$H NMR (300 MHz, DMSO-$d_6$): δ=7.89 (m, 2H), 7.62 (t, 1H), 5.70 (t, 1H), 4.67 (d, 2H).

HPLC: $R_t$=3.53 min (Method H)

MS (ESIpos): m/z=205 (M+NH$_4$)$^+$

EXAMPLE 30A

2-Chloro-3-nitrobenzaldehyde

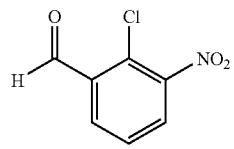

9.2 g (49.05 mmol) of (2-chloro-3-nitrophenyl)methanol and 13.2 g (151.8 mmol) of activated manganese(IV) oxide in 50 ml of chloroform are heated under reflux for 20 h. The mixture is filtered through kieselguhr, concentrated and dried under high vacuum. The resulting title compound is directly reacted further.

$^1$H NMR (200 MHz, DMSO-$d_6$): δ=10.34 (s, 1H), 8.32 (dd, 1H), 8.14 (dd, 1H), 7.79 (t, 1H) ppm.

HPLC: $R_t$=3.76 min (Method H)

MS (ESIpos): m/z=185 (M)$^+$

EXAMPLE 31A

Methyl 7-nitro-1-benzothiophene-2-carboxylate

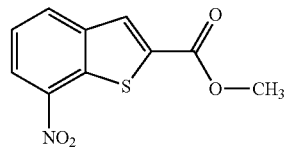

Using 3.04 g (16.4 mmol) of 2-chloro-3-nitrobenzaldehyde, 0.98 g (24.6 mmol) of sodium hydride (60% pure) and 2.09 g (19.7 mmol) of methyl mercaptoacetate, 3.68 g (85% of theory) of the title compound are obtained.

$^1$H NMR (300 MHz, DMSO-$d_6$): δ=8.60 (dd, 1H), 8.53 (dd, 1H), 8.44 (s, 1H), 7.80 (dd, 1H), 3.95 (s, 3H) ppm.

HPLC: $R_t$=4.6 min (Method H)

MS (ESIpos): m/z=255 (M+NH$_4$)$^+$

EXAMPLE 32A

3-Bromo-2-hydroxybenzaldehyde

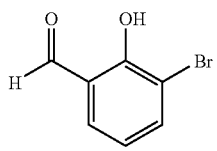

20 g (115.6 mmol) of 4-bromo-2-hydroxybenzaldehyde, together with 16.84 g (176.9 mmol) of magnesium chloride, are initially charged in 500 ml of anhydrous acetonitrile. 41.9 ml (300.6 mmol) of triethylamine are added and the mixture is heated under reflux for 3 h. The mixture is cooled to 0° C., and 300 ml of 2N hydrochloric acid are added. The aqueous phase is extracted three times with a total of 600 ml of diethyl ether. The organic phase is washed with 200 ml of saturated sodium chloride solution and then dried over magnesium sulfate. The solvent is removed under reduced pressure. Any last solvent residues are finally removed under high vacuum. 24 g (64% of theory) of the title compound are isolated and reacted further without further purification.

HPLC: $R_t$=4.25 min (Method H)

MS (ESIpos): m/z=201 (M)$^+$

EXAMPLE 33A

7-Bromo-1-benzofuran-2-carboxylic acid

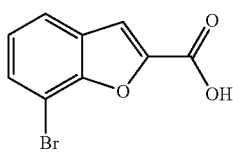

10 g (49.75 mmol) of 3-bromo-2-hydroxybenzaldehyde and 1.84 g (4.97 mmol) of tetra-N-butylammonium iodide are, together with 27.5 g (199.0 mmol) of anhydrous potassium carbonate, initially charged. 24.3 g (223.86 mmol) of methyl chloroacetate are added. The reaction mixture is heated at 130° C. for 4 h and then cooled to 0° C. using an ice bath. 100 ml of THF and 16.75 g (298.5 mmol) of potassium hydroxide in 100 ml of water are added, the mixture is then stirred at 40° C. for 4 h. The solvent is removed under reduced pressure. The residue is diluted with water and acidified with conc. hydrochloric acid. The product is purified on silica gel 60 (mobile phase: toluene/ethyl acetate/acetic acid 40:10:1). The solvent is removed under reduced pressure. Any last solvent residues are finally removed under high vacuum. Fine purification is carried out by preparative HPLC. 303 mg (2.5% of theory) of the title compound are isolated.

HPLC: $R_t$=4.16 min (Method H)

MS (ESIpos): m/z=258 (M+NH$_4$)$^+$

EXAMPLE 34A

6-Bromo-1-benzofuran-2-carboxylic acid

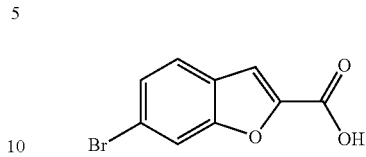

8.0 g (39.8 mmol) of 4-bromo-2-hydroxybenzaldehyde and 1.47 g (3.98 mmol) of tetra-N-butylammonium iodide are, together with 22 g (159.19 mmol) of anhydrous potassium carbonate, initially charged. 9.07 g (83.57 mmol) of methyl chloroacetate are added. The reaction mixture is heated at 130° C. for 4 h and then cooled to 0° C. using an ice bath. 100 ml of THF and 13.4 g (238.8 mmol) of potassium hydroxide in 50 ml of water are added and the mixture is then stirred at RT overnight. The solvent is removed under reduced pressure. The residue is diluted with water and acidified with conc. hydrochloric acid. The product is filtered off and dried under high vacuum. For fine purification, the product is purified on silica gel 60 (mobile phase: toluene→toluene/acetic acid 50:1→toluene/ethyl acetate/acetic acid 35:5:1). The solvent is removed under reduced pressure. 3.8 g (40% of theory) of the title compound are isolated.

$^1$H NMR (400 MHz, methanol-d$_4$): δ=7.91 (m, 1H), 7.61-7.51 (m, 3H) ppm.

HPLC: $R_t$=4.1 min (Method H)

MS (ESIpos): m/z=258 (M+NH$_4$)$^+$

EXAMPLE 35A 5,7-Difluoro-1-benzofuran-2-carboxylic acid

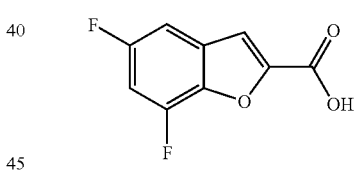

Step a):

1.0 g (7.69 mmol) of 2,4-difluorophenol is initially charged in 6 ml of TFA. Over a period of 30 min, 2.16 g (15.37 mmol) of hexamethylenetetramine are added a little at a time. The mixture is then heated under reflux for 20 h. At RT, 9 ml of water and 4.5 ml of 50% strength sulfuric acid are added. After 2 h at RT, the reaction mixture is extracted twice with in each case 30 ml of ethyl acetate. The combined organic phases are washed four times with 1N hydrochloric acid and once with water and then dried over magnesium sulfate. The crude product is reacted further without further purification.

LC-MS (Method D): $R_t$=3.5 min.

MS (ESIneg): m/z=157 (M−H)$^-$

Step b):

The crude product from the reaction above and 0.28 g (0.77 mmol) of tetra-N-butylammonium iodide are, together with 4.25 g (30.76 mmol) of anhydrous potassium carbonate, initially charged. 1.75 g (16.15 mmol) of methyl chloroacetate are added. The reaction mixture is heated at 130° C. for 4 h and then cooled to 0° C. using an ice bath. 27 ml of THF, 2.59 g (46.14 mmol) of potassium hydroxide and 27 ml of water are added. The mixture is stirred at RT overnight. The solvent is removed under reduced pressure. The residue is diluted with water and acidified with conc. hydrochloric acid. The mixture is extracted twice with ethyl acetate. The combined organic phases are dried over magnesium sulfate and the solvent is removed under reduced pressure using a rotary evaporator. The product is purified on silica gel 60 (mobile phase: toluene/ethyl acetate/acetic acid 35:5:1). The solvent is removed under reduced pressure. Any last solvent residues are finally removed under high vacuum. 235 mg (15% of theory over both steps) of the title compound are isolated.

$^1$H NMR (400 MHz, methanol-$d_4$): δ=7.57 (d, 1H), 7.25 (dd, 1H), 7.08 (dt, 1H) ppm.

HPLC: $R_t$=3.91 min (Method H)

MS (ESIpos): m/z=216 (M+NH$_4$)$^+$

EXAMPLE 36A

3-Bromo-5-fluoro-2-hydroxybenzaldehyde

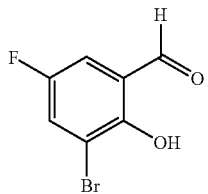

1.0 g (5.24 mmol) of 2-bromo-4-fluorophenol is initially charged in 4 ml of TFA. Over a period of 20 min, 1.47 g (10.47 mmol) of hexamethylenetetramine are added a little at a time. The mixture is then heated under reflux for 28 h. At RT, 6 ml of water and 3 ml of 50% strength sulfuric acid are added. After 2 h at RT, the reaction mixture is extracted twice with in each case 30 ml of ethyl acetate. The combined organic phases are washed four times with 1N hydrochloric acid and once with water and then dried over magnesium sulfate. The crude product is reacted further without further purification.

$^1$H NMR (200 MHz, CDCl$_3$): δ=11.32 (s, 1H, br), 7.66-7.45 (m, 1H), 7.32-7.21 (m, 1H) ppm.

LC-MS (Method D): $R_t$=4.2 min.

MS (ESIneg): m/z=217 (M–H)$^-$

EXAMPLE 37A

7-Bromo-5-fluoro-1-benzofuran-2-carboxylic acid

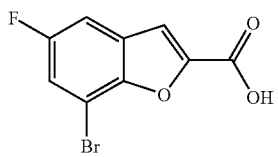

Step a):

1.0 g (5.24 mmol) of 2-bromo-4-fluorophenol is initially charged in 4.0 ml of trifluoroacetic acid. Over a period of 20 min, 1.47 g (10.47 mmol) of hexamethylenetetraamine are added a little at a time. The mixture is then heated under reflux for 28 h. At RT, 6 ml of water and 3 ml of 50% strength sulfuric acid are added. After 2 h, the mixture is extracted twice with in total 60 ml of ethyl acetate. The combined organic phases are washed four times with 1N hydrochloric acid and once with water. The mixture is dried over magnesium sulfate and the solvent is removed under reduced pressure. Any last solvent residues are finally removed under high vacuum. The crude product is reacted further without further purification.

Step b):

The crude product from the reaction above and 0.19 g (0.52 mmol) of tetra-N-butyl-ammonium iodide are, together with 2.9 g (20.96 mmol) of anhydrous potassium carbonate, initially charged. 1.19 g (11.0 mmol) of methyl chloroacetate are added. The reaction mixture is heated at 130° C. for 4 h and then cooled to 0° C. using an ice bath. 18 ml of THF, 1.76 g (31.44 mmol) of potassium hydroxide and 18 ml of water are added. The mixture is stirred at RT overnight. The solvent is removed under reduced pressure. The residue is diluted with water and acidified with conc. hydrochloric acid. The mixture is extracted twice with ethyl acetate. The combined organic phases are dried over magnesium sulfate and the solvent is removed under reduced pressure using a rotary evaporator. The product is purified on silica gel 60 (mobile phase: toluene/acetic acid 40:1). The solvent is removed under reduced pressure. Any last solvent residues are finally removed under high vacuum. 257 mg (19% of theory over both steps) of the title compound are isolated.

$^1$H NMR (400 MHz, methanol-$d_4$): δ=7.60 (m, 1H), 7.48-7.35 (m, H).

HPLC: $R_t$=4.1 min (Method H)

MS (ESIpos): m/z=276 (M+NH$_4$)$^+$

EXAMPLE 38A 2-(Hydroxymethyl)-5-nitrophenol

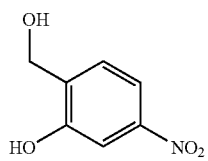

10.0 g (54.6 mmol) of 4-nitrosalicylic acid are initially charged in 100 ml of THF. With ice-cooling, 109 ml of 1 M borane/THF complex are added, and the mixture is stirred at RT overnight. The mixture is concentrated and the precipitate is filtered off with suction. The solid is dissolved in ethyl acetate and dried over magnesium sulfate. After concentration and drying under high vacuum, the title compound is directly reacted further.

MS (ESIpos): m/z=169 (M$^+$)

EXAMPLE 39A

2-Hydroxy-4-nitrobenzaldehyde

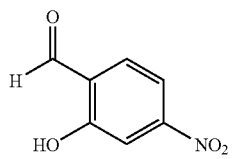

6.0 g (35.5 mmol) of 2-(hydroxymethyl)-5-nitrophenol and 3.1 g (35.5 mmol) of activated manganese (IV) oxide in 100 ml of chloroform are heated under reflux for 20 h. The mixture is filtered through kieselguhr, concentrated and dried under high vacuum. The title compound is directly reacted further.

MS (ESIpos): m/z=167 (M+)

EXAMPLE 40A

6-Nitro-1-benzofuran-2-carboxylic acid

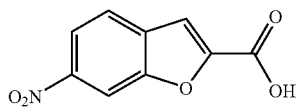

5.8 g (34.7 mmol) of 2-hydroxy-4-nitrobenzaldehyde, 1.28 g (3.5 mmol) of tetra-N-butylammonium iodide and 19.2 g (138.8 mmol) of potassium carbonate are mixed, 7.9 g (72.9 mmol) of methyl chloroacetate are added and the mixture is heated at 130° C. for 12 h. 100 ml of THF and, with ice cooling, 11.7 g (208.2 mmol) of potassium hydroxide are added. Following the addition of 100 ml of water, the mixture is stirred at RT for 20 h. Using concentrated hydrochloric acid, the pH is adjusted to 0. The mixture is extracted with ethyl acetate. The organic phase is washed with water and dried over sodium sulfate. Following the addition of silica gel, the mixture is concentrated and chromatographed on silica gel (mobile phase gradient: toluene to toluene/methanol/glacial acetic acid 35:5:1). Concentration of the product fractions and drying under reduced pressure gives 1.31 g (18.2% of theory) of the title compound.

HPLC: $R_t$=3.8 min (Method H)
MS (ESIpos): m/z=225 (M+NH$_4$)+

EXAMPLE 41A

7-Nitro-1-benzofuran-2-carboxylic acid

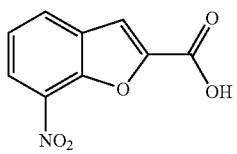

3.0 g (17.9 mmol) of 2-hydroxy-5-nitrobenzaldehyde, 0.66 g (1.80 mmol) of tetra-N-butylammonium iodide and 9.92 g (71.81 mmol) of potassium carbonate are mixed, 4.09 g (37.7 mmol) of methyl chloroacetate are added and the mixture is heated at 130° C. for 4 h. 35 ml of THF and, with ice cooling, 6.04 g (107.71 mmol) of potassium hydroxide are added. Following the addition of 50 ml of water, the mixture is stirred at RT for 20 h. Using concentrated hydrochloric acid, the pH is adjusted to 0. The mixture is extracted with ethyl acetate. The organic phase is washed with water and dried over sodium sulfate. After the addition of silica gel, the mixture is concentrated and chromatographed on silica gel (mobile phase gradient: toluene to toluene/methanol/glacial acetic acid 35:5:1). Concentration of the product fractions and drying under reduced pressure gives 2.00 g (54% of theory) of the title compound.

$^1$H NMR (300 MHz, DMSO-d$_6$): δ=14.0 (s, 1H, br), 8.36 (d, 1H), 8.25 (d, 1H), 7.88 (s, 1H), 7.59 (t, 1H) ppm.
HPLC: $R_t$=3.7 min (Method H)
LC-MS (Method G): $R_t$=2.52 min., m/z=208 (M+H)+
MS (ESIpos): m/z=208 (M+H)+

EXAMPLE 42A

6-[(tert-Butoxycarbonyl)amino]-1-benzothiophene-2-carboxylic acid

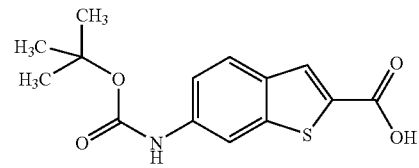

200 mg (1.04 mmol) of 6-amino-1-benzothiophene-2-carboxylic acid are added to 2.5 ml (2.59 mmol) of a 1M solution, cooled to 0° C., of sodium hexamethyldisilazane in tetrahydrofuran. The mixture is stirred at RT for 15 minutes. 271.1 mg (1.24 mmol) of di-tert-butyl pyrocarbonate (Boc$_2$O) are added. The mixture is stirred at RT for 2 h, the contents of the flask are concentrated under reduced pressure, the residue is partioned between 10% strength citric acid solution and ethyl acetate and the aqueous phase is extracted with ethyl acetate. The combined organic phases are dried over sodium sulfate and concentrated. The residue is purified by preparative HPLC. This gives 15 mg (5% of theory) of the title compound.

$^1$H NMR (200 MHz, DMSO-d$_6$): δ=13.33 (s, 1H, br), 9.70 (s, 1H), 8.20 (m, 1H), 7.96 (s, 1H), 7.85 (d, 1H), 7.42 (dd, 1H) ppm.
HPLC: $R_t$=4.4 min (Method H)
MS (ESIpos): m/z=311 (M+NH$_4$)+

EXAMPLE 43A

7-Cyano-1-benzothiophene-2-carboxylic acid

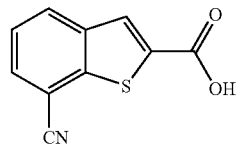

1.6 g (7.36 mmol) of methyl 7-cyano-1-benzothiophene-2-carboxylate gives 1.5 g of a mixture of starting material and product which is used without further purification.

EXAMPLE 44A

6-Cyano-1-benzothiophene-2-carboxylic acid

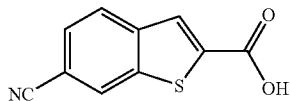

0.6 g (2.76 mmol) of methyl 6-cyano-1-benzothiophene-2-carboxylate give 0.49 g (61.6% of theory) of the desired product.
HPLC: $R_t$=3.9 min (Method H)
MS (ESIpos): m/z=222 (M+H)$^+$

EXAMPLE 45A

Thieno[2,3-f][1,3]benzodioxole-6-carboxylic acid

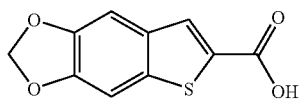

700 mg (2.3 mmol) of methyl thieno[2,3-f][1,3]benzodioxole-6-carboxylate give 513 mg (50% of theory) of a mixture of starting material and product which is used without further purification.
HPLC: $R_t$=3.9 min (Method H)

EXAMPLE 46A

6-Bromo-1-benzothiophene-2-carboxylic acid

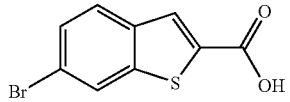

4.0 g (14.8 mmol) of methyl 6-bromo-1-benzothiophene-2-carboxylate give 3.55 g (93.5% of theory) of the desired product.
$^1$H NMR (400 MHz, DMSO-d$_6$): δ=13.48 (s, 1H, br), 8.38 (s, 1H), 8.22 (s, 1H), 7.96 (d, 1H), 7.63 (m, 1H) ppm.
HPLC: $R_t$=4.5 min (Method H)

EXAMPLE 47A

5-Nitro-1-benzothiophene-2-carboxylic acid

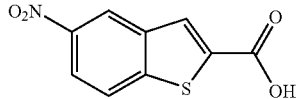

1.10 g (4.39 mmol) of methyl 5-nitro-1-benzothiophene-2-carboxylate give 0.93 g (94.8% of theory) of the desired product.
$^1$H NMR (400 MHz, DMSO-d$_6$): δ=13.88 (s, 1H, br), 8.98 (s, 1H), 8.38-8.25 (m, 3H) ppm.
HPLC: $R_t$=3.9 min (Method H)
MS (ESIpos): m/z=241 (M+NH$_4$)$^+$

EXAMPLE 48A

7-Bromo-1-benzothiophene-2-carboxylic acid

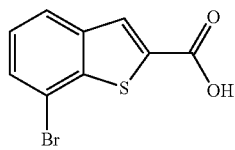

10.0 g (36.9 mmol) of methyl 7-bromo-1-benzothiophene-2-carboxylate give 8.99 g (91.0% of theory) of the desired product.
$^1$H NMR (200 MHz, DMSO-d$_6$): δ=13.76 (s, 1H, br), 8.28 (s, 1H), 8.07 (d, 1H), 7.78 (d, 1H), 7.46 (dd, 1H) ppm.
HPLC: $R_t$=4.4 min (Method H)

EXAMPLE 49A

6-Nitro-1-benzothiophene-2-carboxylic acid

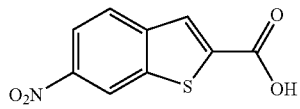

16 g (67.4 mmol) of methyl 6-nitro-1-benzothiophene-2-carboxylate give 15.0 g (99.9% of theory) of the desired product.
$^1$H NMR (200 MHz, DMSO-d$_6$): δ=8.91 (d, 1H), 8.15 (dd, 1H), 8.02 (d, 1H), 7.69 (s, 1H) ppm.
HPLC: $R_t$=4.1 min (Method H)
MS (ESIpos): m/z=241 (M+NH$_4$)$^+$

EXAMPLE 50A

7-Trifluoromethyl-1-benzothiophene-2-carboxylic acid

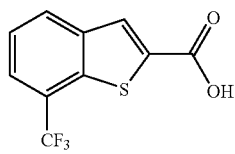

4.2 g (16.2 mmol) of methyl 7-trifluoromethyl-1-benzothiophene-2-carboxylate give 3.89 g (97.8% of theory) of the desired product.
$^1$H NMR (500 MHz, DMSO-d$_6$): δ=13.88 (s, 1H, br), 8.35 (d, 1H), 8.28 (s, 1H), 7.97 (d, 1H), 7.70 (dd, 1H) ppm.
HPLC: $R_t$=4.4 min (Method H)
MS (ESIpos): m/z=247 (M+H)$^+$

EXAMPLE 51A

5-Trifluoromethyl-1-benzothiophene-2-carboxylic acid

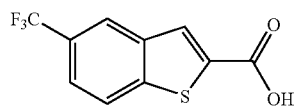

4.28 g (18.5 mmol) of methyl 5-trifluoromethyl-1-benzothiophene-2-carboxylate give 3.62 g (79.4% of theory) of the desired product.

$^1$H NMR (400 MHz, DMSO-$d_6$): δ=13.78 (s, 1H, br), 8.47 (s, 1H), 8.32 (d, 1H), 8.27 (s, 1H), 7.81 (d, 1H) ppm.

HPLC: $R_t$=4.5 min (Method H)

MS (ESIpos): m/z=246 (M$^+$)

EXAMPLE 52A

7-Chloro-1-benzothiophene-2-carboxylic acid

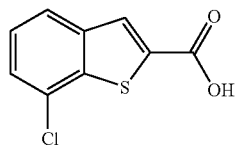

500 mg (2.21 mmol) of methyl 7-chloro-1-benzothiophene-2-carboxylate give 391.6 mg (82.7% of theory) of the desired product.

$^1$H NMR (200 MHz, DMSO-$d_6$): δ=13.78 (s, 1H, br), 8.20 (s, 1H), 8.03 (d, 1H), 7.66 (d, 1H), 7.53 (dd, 1H) ppm.

HPLC: $R_t$=4.2 min (Method H)

MS (ESIpos): m/z=212 (M$^+$)

EXAMPLE 53A

7-Fluoro-1-benzothiophene-2-carboxylic acid

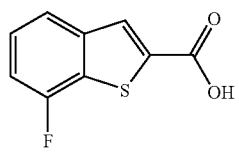

3.27 g (15.6 mmol) of methyl 7-fluoro-1-benzothiophene-2-carboxylate give 3.05 g (100% of theory) of the desired product.

$^1$H NMR (200 MHz, CDCl$_3$): δ=8.05 (d, 1H), 7.68 (d, 1H), 7.38 (m, 1H), 7.15 (m, 1H) ppm.

HPLC: $R_t$=4.1 min (Method H)

MS (ESIpos): m/z=214 (M+NH$_4$)$^+$

EXAMPLE 54A

7-Methoxy-1-benzothiophene-2-carboxylic acid

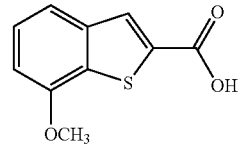

300 mg (1.35 mmol) of methyl 7-methoxy-1-benzothiophene-2-carboxylate give 257.8 mg (85.3% of theory) of the desired product.

$^1$H NMR (200 MHz, DMSO-$d_6$): δ=13.52 (s, 1H, br), 8.10 (s, 1H), 7.59 (d, 1H), 7.43 (dd, 1H), 7.08 (dd, 1H) ppm.

HPLC: $R_t$=4.1 min (Method H)

MS (ESIpos): m/z=226 (M+NH$_4$)$^+$

EXAMPLE 55A

5-Fluoro-1-benzothiophene-2-carboxylic acid

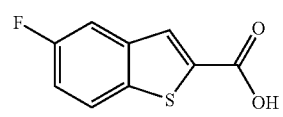

1.0 g (4.76 mmol) of methyl 5-fluoro-1-benzothiophene-2-carboxylate gives 865 mg (92.7% of theory) of the desired product.

$^1$H NMR (200 MHz, DMSO-$d_6$): δ=7.98 (dd, 1H), 7.77 (s, 1H), 7.72 (dd, 1H), 7.29 (ddd, 1H) ppm.

HPLC: $R_t$=4.1 min (Method H)

MS (ESIpos): m/z=196 (M$^+$)

EXAMPLE 56A

4-Fluoro-1-benzothiophene-2-carboxylic acid

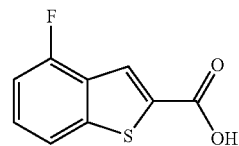

3.0 g (14.3 mmol) of methyl 4-fluoro-1-benzothiophene-2-carboxylate give 2.66 g (91.1% of theory) of the desired product.

$^1$H NMR (200 MHz, DMSO-$d_6$): δ=13.78 (s, 1H, br), 8.05 (s, 1H), 7.92 (d, 1H), 7.55 (ddd, 1H), 7.29 (dd, 1H) ppm.

HPLC: $R_t$=4.1 min (Method H)

MS (ESIpos): m/z=196 (M$^+$)

EXAMPLE 57A 5,7-Difluoro-1-benzothiophene-2-carboxylic acid

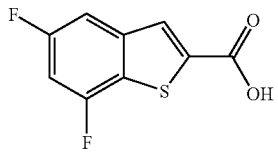

2.4 g (10.5 mmol) of methyl 5,7-difluoro-1-benzothiophene-2-carboxylate give 2.1 g (93.1% of theory) of the desired product.

$^1$H NMR (200 MHz, DMSO-$d_6$): δ=13.88 (s, 1H, br), 8.17 (d, 1H), 7.77 (dd, 1H), 7.56 (m, 1H) ppm.

HPLC: $R_t$=3.9 min (Method H)

MS (ESIpos): m/z=214 (M$^+$)

EXAMPLE 58A 5,6-Dimethoxy-1-benzothiophene-2-carboxylic acid

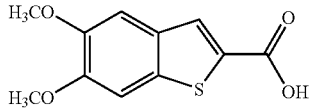

1.0 g (2.97 mmol) of methyl 5,6-dimethoxy-1-benzothiophene-2-carboxylate gives 0.77 g (99% of theory) of the desired product.

$^1$H NMR (200 MHz, DMSO-$d_6$): δ=13.17 (s, 1H, br), 7.93 (s, 1H), 7.58 (s, 1H), 7.48 (s, 1H), 3.85 (s, 3H), 3.82 (s, 3H) ppm.

HPLC: $R_t$=3.7 min (Method H)

MS (ESIpos): m/z=239 (M$^+$), 256 (M+NH$_4$)$^+$

EXAMPLE 59A

6-Methoxy-1-benzothiophene-2-carboxylic acid

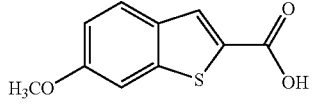

2.52 g (11.34 mmol) of methyl 6-methoxy-1-benzothiophene-2-carboxylate give 2.26 g (95.7% of theory) of the desired product.

$^1$H NMR (200 MHz, DMSO-$d_6$): δ=13.29 (s, 1H, br), 8.01 (s, 1H), 7.88 (d, 1H), 7.60 (d, 1H), 7.07 (dd, 1H), 3.86 (s, 3H) ppm.

HPLC: $R_t$=3.9 min (Method H)

MS (ESIpos): m/z=209 (M+H$^+$), 226 (M+NH$_4$)$^+$

EXAMPLE 60A

4-Nitro-1-benzothiophene-2-carboxylic acid

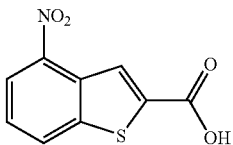

1.0 g (4.22 mmol) of methyl 4-nitro-1-benzothiophene-2-carboxylate gives 0.89 g (94.1% of theory) of the desired product.

$^1$H NMR (200 MHz, DMSO-$d_6$): δ=14.08 (m, 1H, br), 8.58 (d, 1H), 8.57 (s, 1H), 8.42 (d, 1H), 7.77 (dd, 1H) ppm.

HPLC: $R_t$=4.0 min (Method H)

MS (ESIpos): m/z=241 (M+NH$_4$)$^+$

EXAMPLE 61A

7-Nitro-1-benzothiophene-2-carboxylic acid

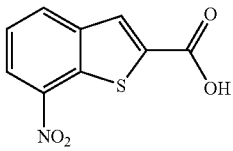

3.6 g (13.7 mmol) of methyl 7-nitro-1-benzothiophene-2-carboxylate give 3.08 g (99.5% of theory) of the desired product.

$^1$H NMR (300 MHz, DMSO-$d_6$): δ=13.79 (s, 1H, br), 8.58 (d, 1H), 8.51 (d, 1H), 8.33 (s, 1H), 7.78 (dd, 1H) ppm.

HPLC: $R_t$=4.0 min (Method H)

MS (ESIpos): m/z=241 (M+NH$_4$)$^+$

EXAMPLE 62A

N-[(3R)-1-Azabicyclo[2.2.2]oct-3-yl]-6-nitro-1-benzothiophene-2-carboxamide hydrochloride

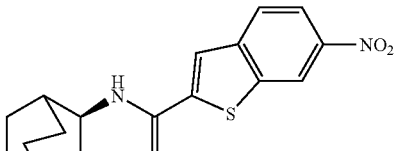

290 mg (1.30 mmol) of 6-nitro-1-benzothiophene-2-carboxylic acid, 258.7 mg (1.30 mmol) of R-3-aminoquinuclidine dihydrochloride, 592.8 mg (1.56 mmol) of HATU, 604.5 mg (4.68 mmol) of N,N-diisopropylethylamine and 2.0 ml of DMF are reacted according to the general procedure. The reaction mixture is purified by preparative HPLC. The product fractions are combined, 1N hydrochloric acid is added and the mixture is then concentrated and dried under high vacuum. This gives 297 mg (62.1% of theory) of the title compound.

$^1$H NMR (400 MHz, methanol-d$_4$): δ=8.95 (s, 1H), 8.29 (dd, 1H), 8.20 (s, 1H), 8.11 (d, 1H), 4.47 (m, 1H), 3.82 (m, 1H), 3.52-3.22 (m, 5H), 2.40 (m, 1H), 2.28 (m, 1H), 2.11 (m, 2H), 1.97 (m, 1H) ppm.

HPLC: R$_t$=3.8 min (Method H)
MS (ESIpos): m/z=332 (M+H)$^+$ (free base).

EXAMPLE 63A

N-[(3R)-1-Azabicyclo[2.2.2]oct-3-yl]-3-chloro-6-nitro-1-benzothiophene-2-carboxamide

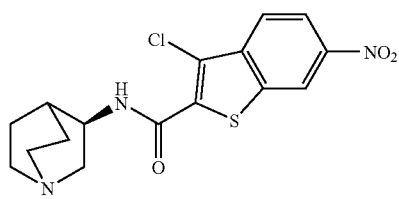

427 mg (1.66 mmol) of 3-chloro-6-nitro-1-benzothiophene-2-carboxylic acid, 300 mg (1.51 mmol) of R-3-aminoquinuclidine dihydrochloride, 687.4 mg (1.81 mmol) of HATU, 701 mg (5.43 mmol) of N,N-diisopropylethylamine and 4.0 ml of DMF are reacted according to the general procedure. 20 ml of methanol and 4 g of Dowex WX2-200 are added, and the mixture is stirred at RT for 1 h. The mixture is filtered and washed successively with water, methanol, methanol/trifluoroacetic acid 9:1 and methanol/trifluoroacetic acid 1:1. Evaporation of the filtrate gives 270 mg (49% of theory) of the title compound.

$^1$H NMR (200 MHz, DMSO-d$_6$): δ=9.24 (d, 1H), 8.77 (d, 1H), 8.38 (dd, 1H), 8.11 (d, 1H), 3.97 (m, 1H), 3.70-3.22 (m, 2H), 3.14 (m, 1H), 2.97-2.44 (m, 4H), 1.93 (m, 1H), 1.83 (m, 1H), 1.60 (m, 2H), 1.39 (m, 1H) ppm.

HPLC: R$_t$=3.9 min (Method H)
MS (ESIpos): m/z=366 (M+H)$^+$ (free base).

WORKING EXAMPLES

Example 1

N-[(3R)-1-Azabicyclo[2.2.2]oct-3-yl]-5-bromo-1-benzothiophene-2-carboxamide hydrochloride

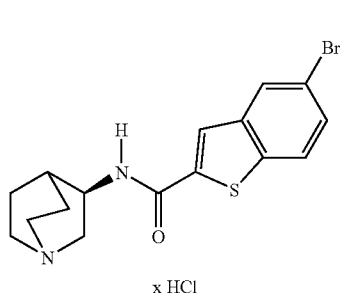

133.7 mg (0.52 mmol) of 5-bromo-1-benzothiophene-2-carboxylic acid, 155.4 mg (0.78 mmol) of (R)-3-aminoquinuclidine dihydrochloride, 296.7 mg (0.78 mmol) of HATU, 369.8 mg (2.86 mmol) of N,N-diisopropylethylamine and 1.5 ml of DMF are reacted according to the general procedure (variant A). The reaction mixture is purified by preparative HPLC. The product is dissolved in acetonitrile, and an excess of 1N hydrochloric acid is added. The solvent is then removed. 175 mg (84% of theory) of the title compound are isolated.

$^1$H NMR (200.1 MHz, DMSO-d$_6$): δ=9.44 (br. s, 1H), 8.95 (d, 1H), 8.30-8.10 (m, 2H), 8.03 (d, 1H), 7.60 (m, 1H), 4.38-4.20 (m, 1H), 3.80-3.55 (m, 1H), 3.42-3.05 (m, 5H), 2.25-2.00 (m, 2H), 1.98-1.62 (m, 3H) ppm.

LC-MS (Method A): R$_t$=2.63 min., MS (ESIpos): m/z=365 (M+H)$^+$ (free base).

Example 2

N-[(3S)-1-Azabicyclo[2.2.2]oct-3-yl]-5-bromo-1-benzothiophene-2-carboxamide hydrochloride

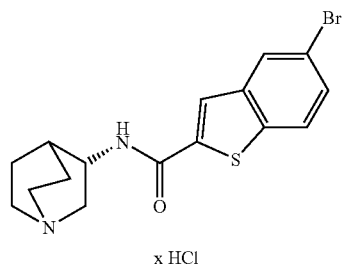

The experiment is carried out in the same manner and on the same scale as described in example 1 using S-3-aminoquinuclidine dihydrochloride. 174 mg (83% of theory) of the title compound are isolated. The analytical data correspond to those of the enantiomeric compound from example 1.

Example 3

N-[(3R)-1-Azabicyclo[2.2.2]oct-3-yl]-6-fluoro-1-benzothiophene-2-carboxamide hydrochloride

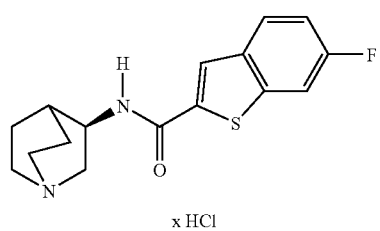

102.1 mg (0.52 mmol) of 6-fluoro-1-benzothiophene-2-carboxylic acid, 155.4 mg (0.78 mmol) of R-3-aminoquinuclidine dihydrochloride, 296.7 mg (0.78 mmol) of HATU, 369.8 mg (2.86 mmol) of N,N-diisopropylethylamine and 1.5 ml of DMF are reacted according to the general procedure (variant A). The reaction mixture is purified by preparative HPLC. The product is dissolved in acetonitrile, and an excess of 1N hydrochloric acid is added. The solvent is then removed. 22 mg (14% of theory) of the title compound are isolated.

LC-MS (Method B): $R_t$=1.22 min., MS (ESIpos): m/z=305 (M+H)$^+$ (free base).

Example 4

N-[(3R)-1-Azabicyclo[2.2.2]oct-3-yl]-5-methyl-1-benzothiophene-2-carboxamide hydrochloride

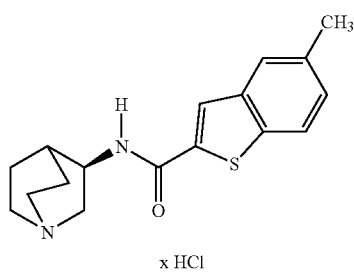

100.0 mg (0.52 mmol) of 5-methyl-1-benzothiophene-2-carboxylic acid, 155.4 mg (0.78 mmol) of R-3-aminoquinuclidine dihydrochloride, 296.7 mg (0.78 mmol) of HATU, 369.8 mg (2.86 mmol) of N,N-diisopropylethylamine and 1.5 ml of DMF are reacted according to the general procedure (variant A). The reaction mixture is purified by preparative HPLC. The product is dissolved in THF, and excess of 1N hydrochloric acid is added. The solvent is then removed. 57 mg (36% of theory) of the title compound are isolated.

MS (ESIpos): m/z=301 (M+H)$^+$ (free base)

LC-MS (Method A): $R_t$=2.50 min., MS (ESIpos): m/z=301 (M+H)$^+$ (free base).

Example 5

N-[(3S)-1-Azabicyclo[2.2.2]oct-3-yl]-5-benzothiophene-2-carboxamide hydrochloride

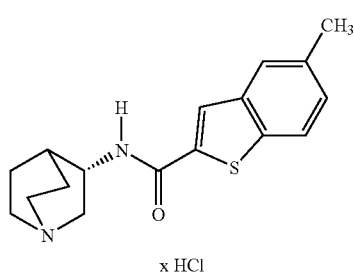

The experiment is carried out in the same manner and on the same scale as described in example 4 using S-3-aminoquinuclidine dihydrochloride. 117 mg (75% of theory) of the title compound are isolated. The analytical data correspond to those of the enantiomeric compound from example 4.

Example 6

N-[(3R)-1-Azabicyclo[2.2.2]oct-3-yl]thieno[3,2-b]pyridine-2-carboxamide

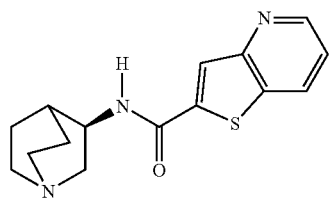

35 mg (0.20 mmol) of thieno[3,2-b]pyridine-2-carboxylic acid, 58.3 mg (0.29 mmol) of R-3-aminoquinuclidine dihydrochloride, 111.4 mg (0.29 mmol) of HATU, 138.8 mg (1.07 mmol) of N,N-diisopropylethylamine and 1.5 ml of DMF are reacted according to the general procedure (variant A). The reaction mixture is purified by preparative HPLC and then subjected to fine purification on silica gel 60 (mobile phase: dichloromethane/methanol/ammonia 90:9:1). 44 mg (78% of theory) of the title compound are isolated.

$^1$H NMR (400.1 MHz, DMSO-d$_6$): δ=8.74 (d, 1H), 8.69 (d, 1H), 8.51 (d, 1H), 8.41 (s, 1H), 7.45 (dd, 1H), 4.02-3.92 (m, 1H), 3.55-3.38 (m, 1H), 2.95-2.85 (m, 1H), 2.78-2.63 (m, 4H), 1.95-1.80 (m, 2H), 1.68-1.52 (m, 1H), 1.40-1.30 (m, 1H) ppm.

MS (ESIpos): m/z=288 (M+H)$^+$ (free base)

LC-MS (Method A): $R_t$=0.39 min., MS (ESIpos): m/z=288 (M+H)$^+$ (free base).

Example 7

N-[(3S)-1-Azabicyclo[2.2.2]oct-3-yl]thieno[3,2-b]pyridine-2-carboxamide

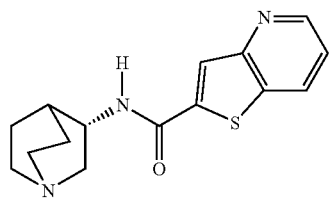

The experiment is carried out in the same manner and on the same scale as described in example 6 using S-3-aminoquinuclidine dihydrochloride. 38 mg (68% of theory) of the title compound are isolated. The analytical data correspond to those of the enantiomeric compound from example 6.

Example 8

N-[(3R)-1-Azabicyclo[2.2.2]oct-3-yl]thieno[2,3-b]pyridine-2-carboxamide hydrochloride

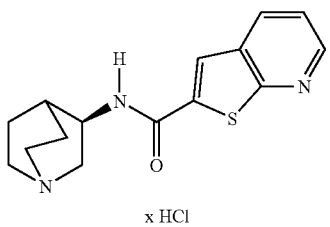

x HCl 45.0 mg (0.25 mmol) of thieno[2,3-b]pyridine-2-carboxylic acid, 75.0 mg (0.38 mmol) of R-3-aminoquinuclidine dihydrochloride, 143.2 mg (0.38 mmol) of HATU, 178.5 mg (1.38 mmol) of N,N-diisopropylethylamine and 1.5 ml of DMF are reacted according to the general procedure (variant A). The reaction mixture is purified by preparative HPLC. 37 mg (51% of theory) of the title compound are isolated.

$^1$H NMR (200.1 MHz, DMSO-$d_6$): δ=9.49 (br. s, 1H), 8.93 (d, 1H), 8.67 (dd, 1H), 8.42 (dd, 1H), 8.19 (s, 1H), 7.52 (dd, 1H), 4.38-4.20 (m, 1H), 3.80-3.55 (m, 1H), 3.42-3.05 (m, 2H), 2.25-2.00 (m, 2H), 1.98-1.62 (m, 3H) ppm.

MS (ESIpos): m/z=288 (M+H)$^+$ (free base)

LC-MS (Method A): $R_t$=0.37 min., MS (ESIpos): m/z=288 (M+H)$^+$ (free base).

Example 9 rac-N-(1-Azabicyclo[2.2.2]oct-3-yl)-5-nitro-1-benzothiophene-2-carboxamide hydrochloride

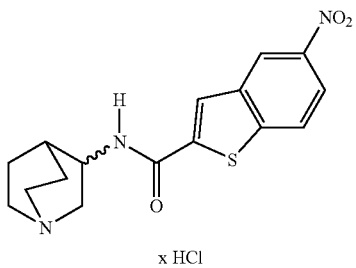

x HCl

At RT, initially 244 mg (0.76 mmol) of TBTU and 104 mg (0.78 mmol) of HOBt followed by 153 mg (0.77 mmol) of 3-aminoquinuclidine dihydrochloride are added to a solution of 180 mg (0.81 mmol) of 5-nitrothiophene-2-carboxylic acid and diisopropylethylamine (0.8 ml) in 4 ml of DMF. The mixture is stirred at RT for 4 h. For work-up, the mixture is concentrated and the residue is taken up in a mixture of chloroform and excess aqueous sodium hydroxide solution. The phases are separated and the aqueous phase is repeatedly re-extracted with chloroform. The combined organic phases are dried over sodium sulfate and concentrated, and the crude product is chromatographed on silica gel (mobile phase: chloroform/methanol/conc. ammonia 100:5:0.5→100:20:2). The resulting product is taken up in THF, excess HCl in diethyl ether is added, then the mixture is concentrated and the product is dried under high vacuum. 136 mg (47% of theory) of the hydrochloride are obtained.

$^1$H NMR (200.1 MHz, DMSO-$d_6$): δ=10.20 (br. s, 1H), 9.32 (d, 1H), 8.90 (d, 1H), 8.55 (s, 1H), 8.40-8.20 (m, 2H), 4.40-4.35 (m, 1H), 3.75-3.60 (m, 1H), 3.42-3.15 (m, 4H), 2.28-2.05 (m, 2H), 2.00-1.65 (m, 3H) ppm.

MS (ESIpos): m/z=332 (M+H)$^+$ (free base).

Example 10 rac-N-(1-Azabicyclo[2.2.2]oct-3-yl)-5-amino-1-benzothiophene-2-carboxamide dihydrochloride

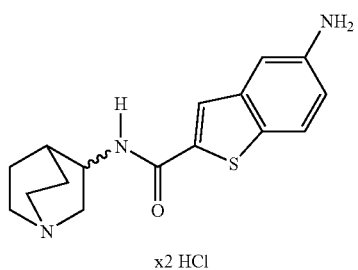

x2 HCl 129 mg (0.35 mmol) of rac-N-(1-azabicyclo[2.2.2]oct-3-yl)-5-nitro-1-benzothiophene-2-carboxamide hydrochloride are dissolved in a mixture of 5 ml of acetic acid and 3 ml of water. 114.7 mg (1.75 mmol) of zinc are added, and the mixture is stirred at RT for 5 h. The reaction mixture is filtered through kieselguhr, the solvent is removed and the residue is taken up in dichloromethane. The resulting solution is washed with 1N aqueous sodium hydroxide solution. The organic phase is dried over sodium sulfate and the solvent is then removed under reduced pressure. The resulting solid is dissolved in a little THF, and an excess of 1N HCl in diethyl ether is added. The THF is then distilled off. 103 mg (80% of theory) of the title compound are isolated.

LC-MS (Method A): $R_t$=0.36 min., MS (ESIpos): m/z=302 (M+H)$^+$ (free base).

Example 11 rac-N-(1-Azabicyclo[2.2.2]oct-3-yl)-5-acetylamino-1-benzothiophene-2-carboxamide hydrochloride

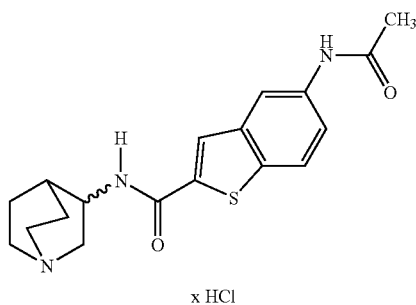

x HCl 41.0 mg (0.12 mmol) of rac-N-(1-azabicyclo[2.2.2]oct-3-yl)-5-amino-1-benzothiophene-2-carboxamide dihydrochloride and 36.8 mg (0.36 mmol) of triethylamine are dissolved in 1.5 ml of DMF. At 0° C., 14.3 mg (0.18 mmol) of acetyl chloride are added, and the mixture is stirred at RT overnight. The reaction mixture is purified by preparative HPLC. 29 mg (63% of theory) of the title compound are isolated.

$^1$H NMR (400.1 MHz, DMSO-d$_6$): δ=10.55 (br. s, 1H), 10.25 (s, 1H), 9.20 (d, 1H), 8.40 (s, 1H), 8.30 (s, 1H), 7.90 (d, 1H), 7.56 (m, 1H), 4.38-4.25 (m, 1H), 3.65-3.55 (m, 1H), 3.50-3.35 (m, 2H), 3.25-3.10 (m, 3H), 2.22-2.10 (m, 2H), 2.07 (s, 3H), 1.95-1.80 (m, 2H), 1.80-1.70 (m, 1H) ppm.

LC-MS (Method A): R$_t$=1.22 min., MS (ESIpos): m/z=344 (M+H)$^+$ (free base).

Example 12

N-(1-Azabicyclo[2.2.2]oct-3-yl)thieno[2,3-b]quinoline-2-carboxamide hydrochloride

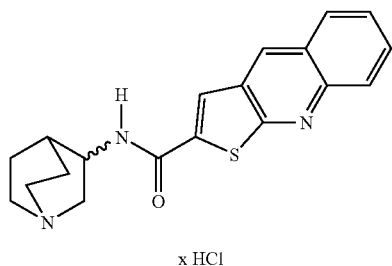

x HCl

Analogously to the procedure for the compound from example 9, 242 mg (1.05 mmol) of thieno[2,3-b]quinoline-2-carboxylic acid [lit.: B. Bhat et al., *Synthesis*, 673ff. (1984)] gives a total of 314 mg (83% of theory) of the title compound as a colorless solid.

$^1$H NMR (300.1 MHz, DMSO-d$_6$): δ=10.50 (br. s, 1H), 9.45 (d, 1H), 9.02 (s, 1H), 8.58 (s, 1H), 8.22 (d, 1H), 8.10 (d, 1H), 7.86 (m$_c$, 1H), 7.66 (m$_c$, 1H), 3.72-3.58 (m, 2H), 3.50-3.40 (m, 2H), 3.30-3.15 (m, 3H), 2.28-2.15 (m, 2H), 1.98-1.86 (m, 2H), 1.82-1.70 (m, 1H), 1.80-1.70 (m, 1H) ppm.

MS (ESIpos): m/z=338 (M+H)$^+$ (free base).

Example 13

N-(1-Azabicyclo[2.2.2]oct-3-yl)benzothiophene-2-carboxamide hydrochloride

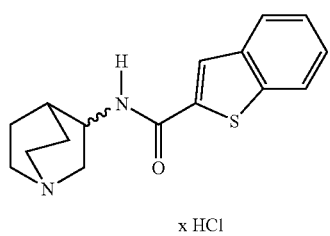

x HCl

Analogously to the procedure for the compound from example 9, 326 mg (1.83 mmol) of benzothiophene-2-carboxylic acid give a total of 332 mg (56% of theory) of the title compound as a colorless solid.

$^1$H NMR (300 MHz, CD$_3$OD): δ=8.1 (s, 1H), 7.90 (m, 2H), 7.40 (m, 2H), 4.45 (m, 1H), 3.80 (m, 1H), 3.55-3.20 (m, 5H), 2.4-2.20 (m, 2H), 2.10 (m, 2H), 1.95 (m, 1H) ppm.

MS (ESIpos): m/z=287 (M+H)$^+$ (free base).

Example 14

N-(1-Azabicyclo[2.2.2]oct-3-yl)-3-chloro-1-benzothiophene-2-carboxamide hydrochloride

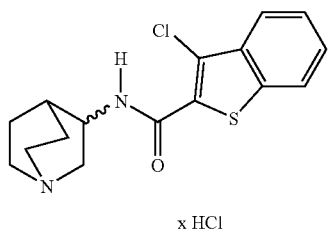

x HCl

Analogously to the procedure for the compound from example 9, 122 mg (0.57 mmol) of 3-chlorobenzothiophene-2-carboxylic acid give a total of 26 mg (13% of theory) of the title compound as a colorless solid.

$^1$H NMR (300 MHz, CD$_3$OD): δ=8.00 (m, 2H), 7.60 (m, 2H), 4.55 (m, 1H), 3.95 (m, 1H), 3.55-3.20 (m, 5H), 2.50 (m, 1H), 2.35 (m, 1H), 2.15 (m, 2H), 2.05 (m, 1H) ppm.

MS (ESIpos): m/z=321 (M+H)$^+$ (free base).

Example 15

N-(1-Azabicyclo[2.2.2]oct-3-yl)-7-bromo-1-benzothiophene-2-carboxamide hydrochloride

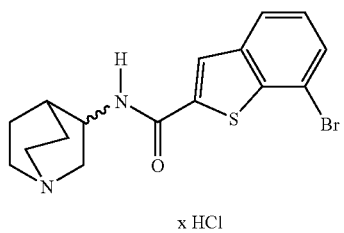

x HCl

Analogously to the procedure for the compound from example 9, 271 mg (1.05 mmol) of 3-chlorobenzothiophene-2-carboxylic acid give a total of 121 mg (29% of theory) of the title compound as a colorless solid.

$^1$H NMR (300 MHz, CD$_3$OD): δ=8.25 (s, 1H), 7.90 (d, 1H), 7.65 (d, 1H), 7.40 (dd, 1H), 4.45 (m, 1H), 3.85 (m, 1H), 3.55-3.30 (m, 5H), 2.40 (m, 1H), 2.35 (m, 1H), 2.10 (m, 2H), 2.00 (m, 1H) ppm.

MS (ESIpos): m/z=365 (M+H)$^+$ (free base).

Example 16

N-(1-Azabicyclo[2.2.2]oct-3-yl)benzofuran-2-carboxamide hydrochloride

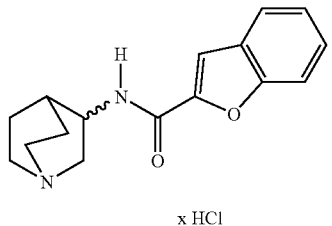

x HCl

Analogously to the procedure for the compound from example 9, 165 mg (0.91 mmol) of benzofuran-2-carboxylic acid give a total of 218 mg (78% of theory) of the title compound as a colorless solid.

$^1$H NMR (300 MHz, CDCl$_3$): δ=11.50 (s, 1H), 8.6 (d, 1H), 7.80 (s, 1H), 7.60 (d, 1H), 7.55 (d, 1H), 7.35 (dd, 1H), 7.20 (dd, 1H), 4.65 (m, 1H), 4.25 (m, 1H), 4.05 (m, 1H), 3.55 (m, 1H), 3.40-3.20 (m, 3H), 2.40 (m, 1H), 2.25-2.00 (m, 2H), 1.95-1.75 (m, 2H) ppm.

MS (ESIpos): m/z=271 (M+H)$^+$ (free base).

Example 17

N-[(3R)-1-Azabicyclo[2.2.2]oct-3-yl]benzofuran-2-carboxamide hydrochloride

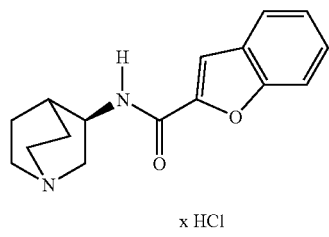

Analogously to the procedure for the compound from example 16, the corresponding reaction with 3R-aminoquinuclidine dihydrochloride gives the corresponding enantiomerically pure product. The analytical data correspond to the those of example 16.

Example 18

N-[(3R)-1-Azabicyclo[2.2.2]oct-3-yl]-8-bromobenzothiophene-2-carboxamide hydrochloride

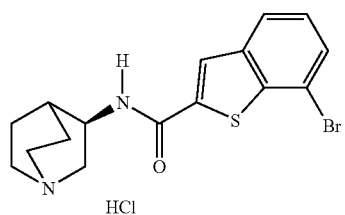

Analogously to the procedure for the compound from example 15, the corresponding reaction with 3R-aminoquinuclidine dihydrochloride gives the corresponding enantiomerically pure product. The analytical data correspond to those of example 15.

Example 19

N-[(3R)-1-Azabicyclo[2.2.2]oct-3-yl]-7-methoxy-1-benzofuran-2-carboxamide hydrochloride

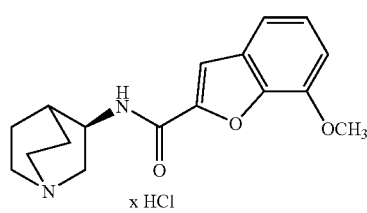

190 mg (0.98 mmol) of 7-methoxybenzofuran-2-carboxylic acid, 200 mg (0.98 mmol) of R-3-aminoquinuclidine dihydrochloride, 450 mg (1.18 mmol) of HATU, 461 mg (3.54 mmol) of N,N-diisopropylethylamine and 2.0 ml of DMF are reacted according to the general procedure (variant B). The reaction mixture is purified by preparative HPLC. An excess of 1N hydrochloric acid is then added to the product. The solvent is removed under reduced pressure. 202 mg (61% of theory) of the title compound are isolated.

$^1$H NMR (200 MHz, DMSO-d$_6$): δ=9.55 (s, 1H, br), 8.91 (d, 1H), 7.62 (s, 1H), 7.36-7.22 (m, 2H), 7.11-7.07 (m, 1H), 4.43-4.29 (m, 1H), 3.95 (s, 3H), 3.70-3.55 (m, 1H), 3.45-3.10 (m, 5H), 2.25-2.00 (m, 2H), 1.98-1.82 (m, 2H), 1.80-1.60 (m, 1H) ppm.

MS (ESIpos): m/z=301 (M+H)$^+$ (free base)

LC-MS (Method D): R$_t$=2.80 min., m/z=301 (M+H)$^+$ (free base).

Example 20

N-[(3S)-1-Azabicyclo[2.2.2]oct-3-yl]-7-methoxy-1-benzofuran-2-carboxamide hydrochloride

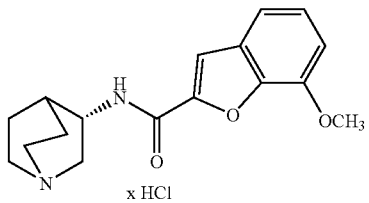

The experiment is carried out in the same manner and on the same scale as in example 19, but using S-3-aminoquinuclidine dihydrochloride. 180 mg (54% of theory) of the title compound are isolated. The analytical data correspond to those of the enantiomeric compound from example 19.

Example 21

N-[(3R)-1-Azabicyclo[2.2.2]oct-3-yl]-5,7-dichloro-1-benzofuran-2-carboxamide hydrochloride

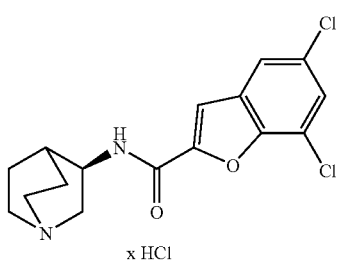

227 mg (0.98 mmol) of 5,7-dichlorobenzofuran-2-carboxylic acid, 200 mg (0.98 mmol) of R-3-aminoquinuclidine dihydrochloride, 449 mg (1.18 mmol) of HATU, 458 mg (3.54 mmol) of N,N-diisopropylethylamine and 2.0 ml of DMF are reacted according to the general procedure (variant B). The reaction mixture is purified by preparative HPLC. An excess of 1N hydrochloric acid is then added to the product. The solvent is removed under reduced pressure. 169 mg (46% of theory) of the title compound are isolated.

$^1$H NMR (200 MHz, DMSO-d$_6$): δ=10.01 (s, 1H, br), 9.11 (d, 1H), 7.94 (d, 1H), 7.82 (s, 1H), 7.65 (d, 1H), 4.43-4.29 (m, 1H), 3.70-3.55 (m, 1H), 3.45-3.10 (m, 5H), 2.25-2.00 (m, 2H), 1.98-1.82 (m, 2H), 1.80-1.60 (m, 1H) ppm.

MS (ESIpos): m/z=339 (M+H)$^+$ (free base)

LC-MS (Method D): R$_t$=3.21 min., m/z=339 (M+H)$^+$ (free base).

Example 22

N-[(3S)-1-Azabicyclo[2.2.2]oct-3-yl]-5,7-dichloro-1-benzofuran-2-carboxamide hydrochloride

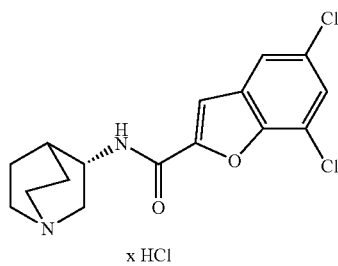

The experiment is carried out in the same manner and on the same scale as for the compound from example 21, but using S-3-aminoquinuclidine dihydrochloride. 216 mg (58% of theory) of the title compound are isolated. The analytical data correspond to those of the enantiomeric compound from example 21.

Example 23

N-[(3R)-1-Azabicyclo[2.2.2]oct-3-yl]-5-bromo-1-benzofuran-2-carboxamide hydrochloride

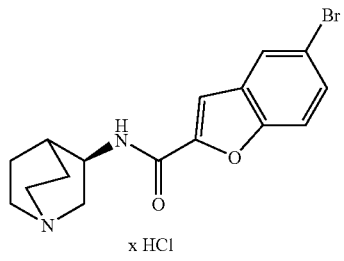

240 mg (0.98 mmol) of 5-bromobenzofuran-2-carboxylic acid, 200 mg (0.98 mmol) of R-3-aminoquinuclidine dihydrochloride, 450 mg (1.18 mmol) of HATU, 460 mg (3.54 mmol) of N,N-diisopropylethylamine and 2.0 ml of DMF are reacted according to the general procedure (variant B). The reaction mixture is purified by preparative HPLC. An excess of 1N hydrochloric acid is then added to the product. The solvent is removed under reduced pressure. 202 mg (53% of theory) of the title compound are isolated.

$^1$H NMR (200 MHz, DMSO-d$_6$): δ=9.38 (s, 1H, br), 8.88 (d, 1H), 7.60 (s, 1H), 7.38-7.20 (m, 2H), 7.09 (dd, 1H), 4.43-4.29 (m, 1H), 3.70-3.55 (m, 1H), 3.45-3.10 (m, 5H), 2.25-2.00 (m, 2H), 1.98-1.82 (m, 2H), 1.80-1.60 (m, 1H) ppm.

MS (ESIpos): m/z=349 (M+H)$^+$ (free base)

LC-MS (Method D): R$_t$=2.71 min., m/z=349 (M+H)$^+$ (free base).

Example 24

N-[(3S)-1-Azabicyclo[2.2.2]oct-3-yl]-5-bromo-1-benzofuran-2-carboxamide hydrochloride

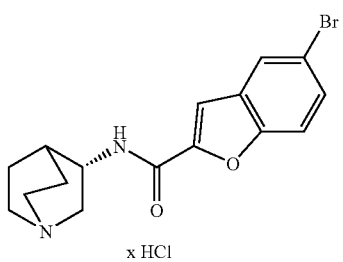

The experiment is carried out in the same manner and on the same scale as for the compound from example 23, but using S-3-aminoquinuclidine dihydrochloride. 277 mg (73% of theory) of the title compound are isolated. The analytical data correspond to those of the enantiomeric compound from example 23.

Example 25

N-[(3R)-1-Azabicyclo[2.2.2]oct-3-yl]-5-chloro-1-benzofuran-2-carboxamide hydrochloride

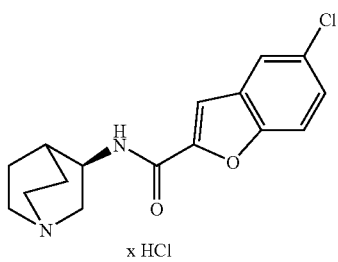

190 mg (0.98 mmol) of 5-chlorobenzofuran-2-carboxylic acid, 200 mg (0.98 mmol) of R-3-aminoquinuclidine dihydrochloride, 450 mg (1.18 mmol) of HATU, 460 mg (3.54 mmol) of N,N-diisopropylethylamine and 2.0 ml of DMF are reacted according to the general procedure (variant B). The reaction mixture is purified by preparative HPLC. An excess of 1N hydrochloric acid is then added to the product. The solvent is removed under reduced pressure. 145 mg (43% of theory) of the title compound are isolated.

$^1$H NMR (200 MHz, DMSO-d$_6$): δ=9.78 (s, 1H, br), 9.07 (d, 1H), 7.91 (d, 1H), 7.72 (d, 1H), 7.64 (s, 1H), 7.51 (dd, 1H), 4.43-4.29 (m, 1H), 3.70-3.55 (m, 1H), 3.45-3.10 (m, 5H), 2.25-2.00 (m, 2H), 1.98-1.82 (m, 2H), 1.80-1.60 (m, 1H) ppm.

MS (ESIpos): m/z=305 (M+H)$^+$

LC-MS (Method D): R$_t$=2.96 min., m/z=305 (M+H)$^+$ (free base).

Example 26

N-[(3S)-1-Azabicyclo[2.2.2]oct-3-yl]-5-chloro-1-benzofuran-2-carboxamide hydrochloride

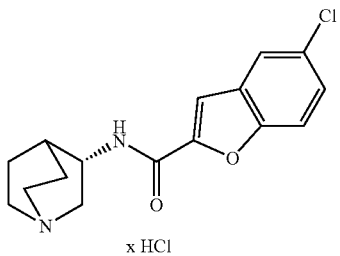

The experiment is carried out in the same manner and on the same scale as for the compound from example 25, but using S-3-aminoquinuclidine dihydrochloride. 100 mg (30% of theory) of the title compound are isolated. The analytical data correspond to those of the enantiomeric compound from example 25.

Example 27

N-[(3R)-1-Azabicyclo[2.2.2]oct-3-yl]-7-methoxy-5-nitro-1-benzofuran-2-carboxamide hydrochloride

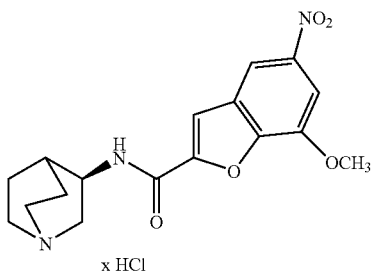

230 mg (0.98 mmol) of 7-methoxy-5-nitro-1-benzofuran-2-carboxylic acid, 200 mg (0.98 mmol) of R-3-aminoquinuclidine dihydrochloride, 450 mg (1.18 mmol) of HATU, 460 mg (3.54 mmol) of N,N-diisopropylethylamine and 2.0 ml of DMF are reacted according to the general procedure (variant B). The reaction mixture is purified by preparative HPLC. An excess of 1N hydrochloric acid is then added to the product. The solvent is removed under reduced pressure. 127 mg (34% of theory) of the title compound are isolated.

$^1$H NMR (200 MHz, DMSO-d$_6$): δ=9.56 (s, 1H, br), 9.10 (d, 1H), 8.42 (d, 1H), 7.88 (d, 1H), 7.84 (s, 1H), 4.43-4.29 (m, 1H), 4.10 (s, 3H), 3.70-3.55 (m, 1H), 3.45-3.10 (m, 5H), 2.25-2.00 (m, 2H), 1.98-1.82 (m, 2H), 1.80-1.60 (m, 1H) ppm.

MS (ESIpos): m/z=346 (M+H)$^+$ (free base)

LC-MS (Method D): R$_t$=3.16 min., m/z=346 (M+H)$^+$ (free base).

Example 28

N-[(3S)-1-Azabicyclo[2.2.2]oct-3-yl]-7-methoxy-5-nitro-1-benzofuran-2-carboxamide hydrochloride

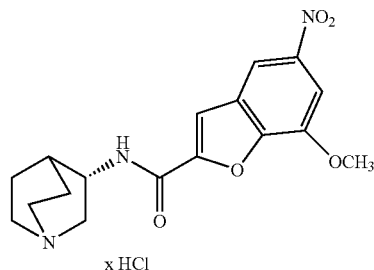

The experiment is carried out in the same manner and on the same scale as for the compound from example 27, but using S-3-aminoquinuclidine dihydrochloride. 83 mg (20% of theory) of the title compound are isolated. The analytical data correspond to those of the enantiomeric compound from example 27.

Example 29

5-Amino-N-[(3R)-1-azabicyclo[2.2.2]oct-3-yl]-7-methoxy-1-benzofuran-2-carboxamide dihydrochloride

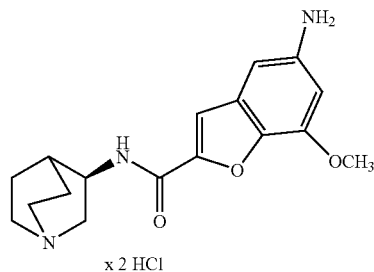

Initially, N-[(3R)-1-azabicyclo[2.2.2]oct-3-yl]-7-methoxy-5-nitro-1-benzofuran-2-carboxamide hydrochloride (120 mg, 0.31 mmol) is converted into the free base. To this end, the compound is taken up in ethyl acetate, and 30% strength aqueous sodium hydroxide solution is added. The aqueous phase is extracted repeatedly with ethyl acetate. The extract is dried over magnesium sulfate and the solvent is removed under reduced pressure. The free base is dissolved in 3 ml of methanol. 120 mg (1.84 mmol) of ammonium formate are added, and the mixture is heated under reflux for 4 h. The reaction mixture is filtered through Celite, and the filter cake is washed with ethanol and ethyl acetate. The crude product is subjected to fine purification on silica gel 60 (mobile phase: dichloromethane→dichloromethane/methanol 10:1→dichloromethane/methanol/ammonia 80:20:2). An excess of 4N HCl in dioxane is added to the free base. The solvent is then removed under reduced pressure. 25 mg (17% of theory) of the title compound are isolated.

$^1$H NMR (400 MHz, D$_2$O): δ=7.62 (s, 1H), 7.40 (d, 1H), 7.07 (d, 1H), 4.56-4.50 (m, 1H), 4.09 (s, 3H), 3.90-3.80 (m, 1H), 3.55-3.30 (m, 5H), 2.50-2.40 (m, 1H), 2.35-2.21 (m, 1H), 2.20-2.05 (m, 2H), 2.06-1.93 (m, 1H) ppm.

MS (ESIpos): m/z=316 (M+H)+ (free base)
LC-MS (Method D): $R_t$=0.43 min., m/z=316 (M+H)+ (free base).

Example 30

N-[(3R)-1-Azabicyclo[2.2.2]oct-3-yl]-5-nitro-1-benzofuran-2-carboxamide

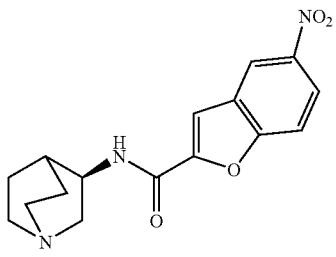

1248 mg (6.03 mmol) of 5-nitrobenzofuran-2-carboxylic acid, 1000 mg (5.02 mmol) of (R)-3-aminoquinuclidine dihydrochloride, 2291 mg (6.03 mmol) of HATU, 2250 mg (18.08 mmol) of N,N-diisopropylethylamine and 15 ml of DMF are reacted according to the general procedure (variant B). DMF is removed under reduced pressure. The reaction mixture is taken up in methanol and stirred together with acidic ion exchange resin (Dowex WX2-200) for about 40 min. The loaded ion exchanger is washed six times with in each case 100 ml of methanol. It is then eluted using methanol/triethylamine 99:1 to 90:10. The solvent is removed under reduced pressure. The product is taken up in 1N aqueous sodium hydroxide solution and extracted three times with ethyl acetate. The extract is dried on magnesium sulfate. 1100 mg (69% of theory) of the title compound are isolated.

$^1$H NMR (400 MHz, methanol-$d_4$): δ=8.67 (d, 1H), 8.36 (dd, 3H), 7.75 (d, 1H), 7.67 (s, 1H), 4.24-4.18 (m, 1H), 3.34-3.29 (m, 1H), 3.07-2.97 (m, 1H), 2.93-2.77 (m, 4H), 2.13-2.05 (m, 1H), 1.98-1.86 (m, 1H), 1.84-1.75 (m, 2H), 1.63-1.53 (m, 1H) ppm.

MS (ESIpos): m/z=316 (M+H)+ (free base)
LC-MS (Method D): $R_t$=2.28 min., m/z=316 (M+H)+ (free base).

Example 31

N-[(3S)-1-Azabicyclo[2.2.2]oct-3-yl]-5-nitro-1-benzofuran-2-carboxamide

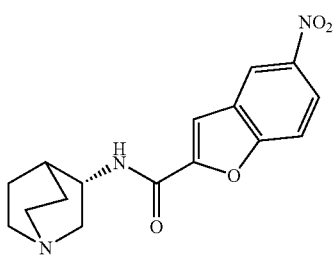

187 mg (0.90 mmol) of 5-nitrobenzofuran-2-carboxylic acid, 150 mg (0.75 mmol) of (S)-3-aminoquinuclidine dihydrochloride, 343.7 mg (0.90 mmol) of HATU, 350.5 mg (3.71 mmol) of N,N-diisopropylethylamine and 5 ml of DMF are reacted according to the general procedure (variant B). 169.1 mg (70% of theory) of the title compound are obtained. The analytical data correspond to those of the enantiomeric compound from example 30.

Example 32

N-[(3R)-1-Azabicyclo[2.2.2]oct-3-yl]-5-amino-1-benzofuran-2-carboxamide

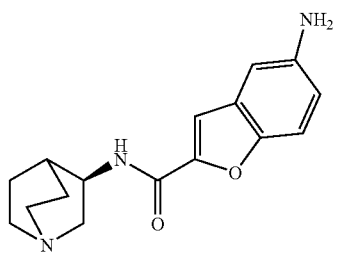

2.0 ml (4 mmol) of a 2 M tin(II) chloride solution in DMF are added to N-[(3R)-1-azabicyclo[2.2.2]oct-3-yl]-5-nitro-1-benzofuran-2-carboxamide (100 mg, 0.32 mmol). The mixture is stirred overnight. The reaction mixture is poured into water and made basic using 1N aqueous sodium hydroxide solution. The aqueous phase is extracted six times with ethyl acetate. The combined organic phases are dried over magnesium sulfate, and the solvent is removed under reduced pressure using a rotary evaporator. The crude product is taken up in methanol and shaken together with acidic ion exchange resin (Dowex WX2-200) for about 20 min. The loaded ion exchanger is washed three times with in each ase 30 ml of methanol, then with water/methanol 8:2, again with methanol, with dichloromethane and finally again with methanol. The product is eluted using methanol/triethylamine 95:5. The solvent is removed under reduced pressure using a rotary evaporator. 52 mg (58% of theory) of the title compound are isolated.

$^1$H NMR (400 MHz, methanol-$d_4$): δ=7.35 (d, 1H), 7.32 (s, 1H), 6.97 (d, 1H), 6.89 (dd, 3H), 4.24-4.18 (m, 1H), 3.34-3.29 (m, 1H), 3.07-2.97 (m, 1H), 2.93-2.77 (m, 4H), 2.13-2.05 (m, 1H), 1.98-1.86 (m, 1H), 1.84-1.75 (m, 2H), 1.63-1.53 (m, 1H) ppm.

MS (ESIpos): m/z=286 (M+H)+ (free base)
LC-MS (Method D): $R_t$=2.02 min., m/z=286 (M+H)+ (free base).

Example 33

N-[(3S)-1-Azabicyclo[2.2.2]oct-3-yl]-5-amino-1-benzofuran-2-carboxamide

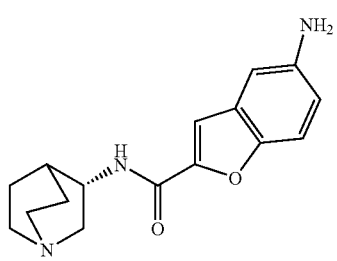

2.0 ml (4 mmol) of a 2 M tin(II) chloride solution in DMF are added to N-[(3S)-1-azabicyclo[2.2.2]oct-3-yl]-5-nitro-1-benzofuran-2-carboxamide (135 mg, 0.32 mmol), and the mixture is stirred at RT for 18 h. The crude product is taken up in methanol and shaken together with acidic ion exchange resin (Dowex WX2-200) for about 20 min. The loaded ion exchanger is washed three times with in each case 30 ml of methanol, then with water/methanol 8:2, again with methanol, with dichloromethane and finally again with methanol. The product is eluted using methanol/triethylamine 95:5. The solvent is removed under reduced pressure using a rotary evaporator, and 20 ml of 1N aqueous sodium hydroxide solution are added to the crude mixture. The aqueous phase is extracted six times with in each case 20 ml of ethyl acetate. The combined organic phases are dried over magnesium sulfate and the solvent is removed under reduced pressure using a rotary evaporator. 100.7 mg (82% of theory) of the title compound are isolated. The analytical data correspond to those of the enantiomeric compound from example 32.

Example 34

N-[(3R)-1-Azabicyclo[2.2.2]oct-3-yl]-6-nitro-1-benzofuran-2-carboxamide

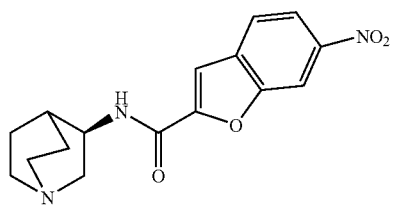

1040 mg (5.02 mmol) of 6-nitrobenzofuran-2-carboxylic acid, 1000 mg (5.02 mmol) of (R)-3-aminoquinuclidine dihydrochloride, 2290 mg (6.03 mmol) of HATU, 2250 mg (18.08 mmol) of N,N-diisopropylethylamine and 15 ml of DMF are reacted according to the general procedure (variant B). DMF is removed under reduced pressure. The product is taken up in 100 ml of 1N aqueous sodium hydroxide solution and extracted three times with in each case 50 ml of ethyl acetate. The combined organic phases are dried over magnesium sulfate and the solvent is removed under reduced pressure using a rotary evaporator. The reaction mixture is taken up in methanol and, together with acidic ion exchange resin (Dowex WX2-200), stirred for about 40 min. The loaded ion exchange is washed six times with in each case 100 ml of methanol. The product is then eluted with methanol/triethylamine 99:1 to 90:10. The solvent is removed under reduced pressure. The product is dried over magnesium sulfate. 1.75 g (99% of theory) of the title compound are isolated.

$^1$H NMR (200 MHz, CDCl$_3$): δ=8.45 (s, 1H), 8.25 (dd, 1H), 7.80 (d, 1H), 7.56 (s, 1H), 7.05 (d, 1H), 4.35-4.18 (m, 1H), 3.1-2.82 (m, 5H), 2.20-2.10 (m, 1H), 1.98-1.53 (m, 5H) ppm.

MS (ESIpos): m/z=316 (M+H)$^+$ (free base)

HPLC: R$_t$=3.6 min (Method H)

LC-MS (Method D): R$_t$=2.62 min., m/z=316 (M+H)$^+$ (free base).

Example 35

N-[(3R)-1-Azabicyclo[2.2.2]oct-3-yl]-6-amino-1-benzofuran-2-carboxamide

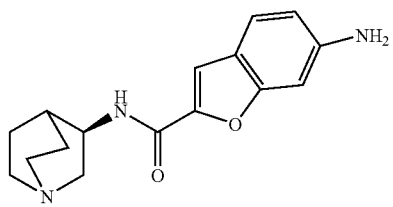

15.0 ml (30 mmol) of a 2 M tin(II) chloride solution in DMF are added to N-[(3R)-1-azabicyclo[2.2.2]oct-3-yl]-6-nitro-1-benzofuran-2-carboxamide (1550 mg, 4.92 mmol). The mixture is stirred overnight. The solvent is removed under reduced pressure using a rotary evaporator. The crude product is taken up in methanol and, together with acidic ion exchange resin (Dowex WX2-200), shaken for about 1 h. The loaded ion exchanger is washed with methanol, then with water, DMF, again with methanol, with dichloromethane and finally again with methanol. The product is eluted with methanol/triethylamine 95:5. The solvent is removed under reduced pressure using a rotary evaporator. The crude product is purified on silica gel 60 (mobile phase: dichloromethane/triethylamine 100:1→dichloro-methane/methanol/triethylamine 100:1:1→dichloromethane/methanol/triethylamine 90:10:1). 643 mg (46% of theory) of the title compound are isolated.

MS (ESIpos): m/z=286 (M+H)$^+$ (free base)

HPLC: R$_t$=2.6 min (Method H)

LC-MS (Method G): R$_t$=1.62 min., m/z=286 (M+H)$^+$ (free base).

Example 36

N-[(3R)-1-Azabicyclo[2.2.2]oct-3-yl]-7-nitro-1-benzofuran-2-carboxamide

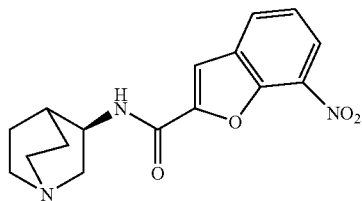

1040 mg (5.02 mmol) of 6-nitrobenzofuran-2-carboxylic acid, 1000 mg (5.02 mmol) of (R)-3-aminoquinuclidine dihydrochloride, 2290 mg (6.03 mmol) of HATU, 2250 mg (18.08 mmol) of N,N-diisopropylethylamine and 9 ml of DMF are reacted according to the general procedure (variant B). DMF is removed under reduced pressure. The product is taken up in 100 ml of 1N aqueous sodium hydroxide solution and extracted three times with in each case 50 ml of ethyl acetate. The combined organic phases are washed eight times with 1N aqueous sodium hydroxide solution and once with saturated sodium chloride solution and then dried over magnesium sulfate, and the solvent is removed under reduced pressure using a rotary evaporator. 1.34 g (79% of theory) of the title compound are obtained.

¹H NMR (400 MHz, methanol-d₄): δ=8.35 (d, 1H), 8.18 (d, 1H), 7.71 (s, 1H), 7.55 (dd, 1H), 4.25-4.18 (m, 1H), 140-3.31 (m, 1H), 3.10-2.97 (m, 1H), 2.93-2.77 (m, 4H), 2.13-2.05 (m, 1H), 2.03-1.92 (m, 1H), 1.84-1.75 (m, 2H), 1.63-1.53 (m, 1H) ppm.

MS (ESIpos): m/z=316 (M+H)⁺ (free base)
HPLC: R$_t$=3.55 min (Method H)
LC-MS (Method E): R$_t$=3.15 min., m/z=316 (M+H)⁺ (free base)

Example 37

N-[(3R)-1-Azabicyclo[2.2.2]oct-3-yl]-7-amino-1-benzofuran-2-carboxamide

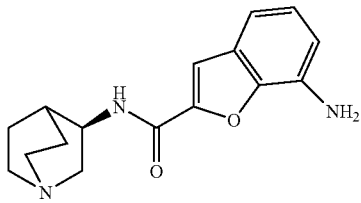

6.0 ml (12 mmol) of a 2 M tin(II) chloride solution in DMF are added to N-[(3R)-1-azabicyclo[2.2.2]oct-3-yl]-7-nitro-1-benzofuran-2-carboxamide (1340 mg, 4.25 mmol). The mixture is stirred overnight. The solvent is removed under reduced pressure using a rotary evaporator. The crude product is taken up in methanol and, together with acidic ion exchange resin (Dowex WX2-200), shaken for about 1 h. The loaded ion exchanger is washed with methanol, then with water, again with methanol, with DMF, again with methanol, with THF, again with methanol, with dichloromethane and finally once more with methanol. The product is eluted with methanol/triethylamine 95:5. The solvent is removed under reduced pressure using a rotary evaporator. 1200 mg (98% of theory) of the title compound are obtained.

¹H NMR (300 MHz, DMSO-d₆): δ=8.18 (m, 1H), 7.40 (s, 1H), 6.98 (d, 1H), 6.87 (d, 1H), 6.65 (d, 1H), 5.45 (br. s, 1H), 4.06-3.94 (m, 1H), 3.29-3.15 (m, 1H), 3.04-2.88 (m, 1H), 2.85-2.65 (m, 4H), 1.98-1.77 (m, 2H), 1.72-1.54 (m, 2H), 1.48-1.32 (m, 1H) ppm.

MS (ESIpos): m/z=286 (M+H)⁺ (free base)
HPLC: R$_t$=2.95 min (Method H)
LC-MS (Method E): R$_t$=3.03 min., m/z=286 (M+H)⁺ (free base).

Example 38

N-[(3R)-1-Azabicyclo[2.2.2]oct-3-yl]-5,7-difluoro-1-benzofuran-2-carboxamide

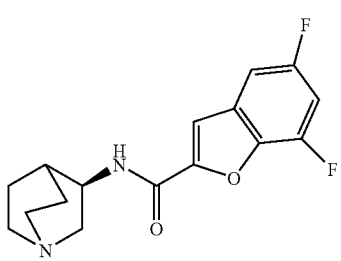

55 mg (0.28 mmol) of 5,7-difluoro-1-benzofuran-2-carboxylic acid, 50 mg (0.25 mmol) of (R)-3-aminoquinuclidine dihydrochloride, 114.6 mg (0.3 mmol) of HATU, 117 mg (0.9 mmol) of N,N-diisopropylethylamine and 2.0 ml of DMF are reacted according to the general procedure (variant B). DMF is removed under reduced pressure and the crude product is dissolved in 1N aqueous sodium hydroxide solution. The aqueous phase is extracted with ethyl acetate. The combined organic phases are dried over magnesium sulfate and the solvent is removed under reduced pressure using a rotary evaporator. The crude product is taken up in methanol and, together with acidic ion exchange resin (Dowex WX2-200), shaken for about 20 min. The loaded ion exchanger is washed three times with in each case 30 ml of methanol, then with water, again with methanol, with dichloromethane and finally again with methanol. The product is eluted with methanol/triethylamine 95:5. The solvent is removed under reduced pressure using a rotary evaporator. 40 mg (52% of theory) of the title compound are isolated.

¹H NMR (400 MHz, methanol-d₄): δ=7.58-7.55 (d, 1H), 7.34-7.29 (m, 1H), 7.20-7.13 (m, 1H), 4.24-4.18 (m, 1H), 3.34-3.29 (m, 1H), 3.07-2.97 (m, 1H), 2.93-2.77 (m, 4H), 2.13-2.05 (m, 1H), 1.98-1.86 (m, 1H), 1.84-1.75 (m, 2H), 1.63-1.53 (m, 1H) ppm.

MS (ESIpos): m/z=307 (M+H)⁺ (free base)
LC-MS (Method D): R$_t$=2.70 min., m/z=307 (M+H)⁺ (free base).

Example 39

N-[(3S)-1-Azabicyclo[2.2.2]oct-3-yl]-5,7-difluoro-1-benzofuran-2-carboxamide

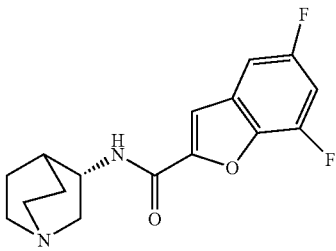

The experiment is carried out in the same manner and on the same scale as for the compound from example 38, but using S-3-aminoquinuclidine dihydrochloride. 63 mg (82% of theory) of the title compound are isolated. The analytical data correspond to those of the enantiomeric compound from example 38.

Example 40

N-[(3R)-1-Azabicyclo[2.2.2]oct-3-yl]-5-fluoro-7-bromo-1-benzofuran-2-carboxamide

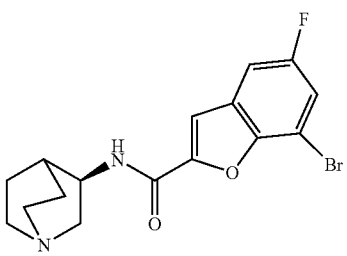

143 mg (0.55 mmol) of 5-fluoro-7-bromo-1-benzofuran-2-carboxylic acid, 100 mg (0.50 mmol) of (R)-3-aminoquinuclidine dihydrochloride, 229.14 mg (0.6 mmol) of HATU, 234 mg (1.81 mmol) of N,N-diisopropylethylamine and 2.0 ml of DMF are reacted according to the general procedure (variant B). DMF is removed under reduced pressure and the crude product is dissolved in 1N aqueous sodium hydroxide solution. The aqueous phase is extracted with ethyl acetate and washed with saturated sodium chloride solution. The combined organic phases are dried over magnesium sulfate and the solvent is removed under reduced pressure using a rotary evaporator. The crude product is taken up in methanol and, together with acidic ion exchange resin (Dowex WX2-200), shaken for about 20 min. The loaded ion exchanger is washed three times with in each case 30 ml of methanol, then with water, again with methanol, with dichloromethane and finally again with methanol. The product is eluted with methanol/triethylamine 95:5. The solvent is removed under reduced pressure using a rotary evaporator. 181 mg (98% of theory) of the title compound are isolated.

$^1$H NMR (400 MHz, methanol-$d_4$): S=7.59 (d, 1H), 7.53-7.46 (m, 2H), 4.24-4.18 (m, 1H), 3.34-3.29 (m, 1H), 3.07-2.97 (m, 1H), 2.93-2.77 (m, 4H), 2.13-2.05 (m, 1H), 1.98-1.86 (m, 1H), 1.84-1.75 (m, 2H), 1.63-1.53 (m, 1H) ppm.

MS (ESIpos): m/z=367 (M+H)$^+$ (free base)

LC-MS (Method D): $R_t$=2.92 min., m/z=367 (M+H)$^+$ (free base).

Example 41

N-[(3S)-1-Azabicyclo[2.2.2]oct-3-yl]-5-fluoro-7-bromo-1-benzofuran-2-carboxamide

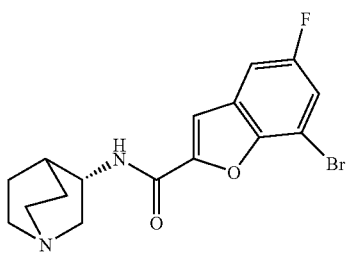

The experiment is carried out in the same manner and using half the amount of starting material and reagents as for the compound from example 40, using S-3-aminoquinuclidine dihydrochloride. 115 mg (47% of theory) of the title compound are isolated. The analytical data correspond to those of the enantiomeric compound from example 40.

Example 42

N-[(3R)-1-Azabicyclo[2.2.2]oct-3-yl]-5-fluoro-1-benzofuran-2-carboxamide hydrochloride

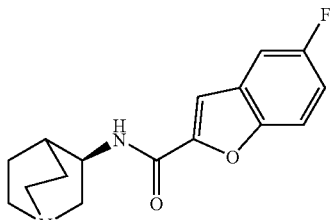

x HCl 180 mg (1.00 mmol) of 5-fluoro-1-benzofuran-2-carboxylic acid, 200 mg (1.0 mmol) of R-3-aminoquinuclidine dihydrochloride, 460 mg (1.2 mmol) of HATU, 470 mg (3.62 mmol) of N,N-diisopropylethylamine and 2.0 ml of DMF are reacted according to the general procedure (variant B). The reaction mixture is purified by preparative HPLC. 1N aqueous sodium hydroxide solution is added to the product purified in this manner, and the mixture is extracted with ethyl acetate. The combined organic phases are dried over sodium sulfate and the solvent is removed under reduced pressure. The product is dissolved in methanol and, using an excess of 4N HCl in dioxane, converted into the hydrochloride. 256 mg (79% of theory) of the title compound are isolated.

$^1$H NMR (200 MHz, DMSO-$d_6$): δ=10.23 (s, 1H, br), 9.12 (d, 1H), 7.76-7.59 (m, 3H), 7.40-7.29 (m, 1H), 4.42-4.27 (m, 1H), 3.70-3.55 (m, 1H), 3.45-3.10 (m, 5H), 2.25-2.00 (m, 2H), 1.98-1.82 (m, 2H), 1.80-1.60 (m, 1H) ppm.

MS (ESIpos): m/z=289 (M+H)$^+$ (free base)

LC-MS (Method D): $R_t$=1.4 min., m/z=289 (M+H)$^+$ (free base).

Example 43

N-[(3S)-1-Azabicyclo[2.2.2]oct-3-yl]-5-fluoro-1-benzofuran-2-carboxamide hydrochloride

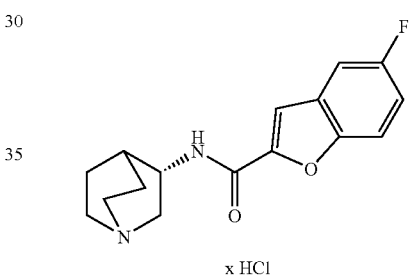

x HCl

The experiment is carried out in the same manner and on the same scale as for the compound from example 42, but using S-3-aminoquinuclidine dihydrochloride. 224 mg (69% of theory) of the title compound are isolated. The analytical data correspond to those of the enantiomeric compound from example 42.

Example 44

N-[(3R)-1-Azabicyclo[2.2.2]oct-3-yl]-7-fluoro-1-benzofuran-2-carboxamide hydrochloride

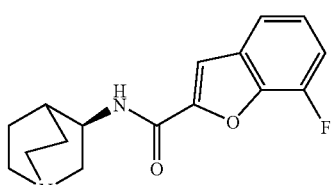

x HCl 130 mg (0.73 mmol) of 7-fluorobenzofuran-2-carboxylic acid, 150 mg (0.73 mmol) of R-3-aminoquinuclidine dihydrochloride, 330 mg (0.87 mmol) of HATU, 340 mg (2.62 mmol) of N,N-diisopropylethylamine and 2.0 ml of DMF are reacted according to the general procedure (variant B). The reaction mixture is purified by preparative HPLC. An excess of 4 N HCl in dioxane is then added to the product. The solvent is removed under reduced pressure. 116 mg (49% of theory) of the title compound are isolated.

$^1$H NMR (400 MHz, methanol-$d_4$): δ=7.67-7.53 (m, 1H), 7.40-7.22 (m, 2H), 4.54-4.46 (m, 1H), 3.92-3.79 (m, 1H), 3.53-3.29 (m, 1H), 3.53-3.29 (m, 4H), 2.46-2.39 (m, 1H), 2.31-2.20 (m, 1H), 2.17-2.07 (m, 2H), 2.06-1.92 (m, 1H) ppm.

MS (ESIpos): m/z=289 (M+H)$^+$ (free base)

LC-MS (Method D): R$_t$=2.50 min., m/z=289 (M+H)$^+$ (free base).

Example 45

N-[(3S)-1-Azabicyclo[2.2.2]oct-3-yl]-7-fluoro-1-benzofuran-2-carboxamide hydrochloride

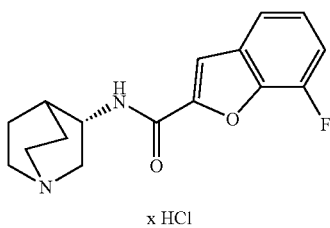

x HCl

The experiment is carried out in the same manner and on the same scale as for the compound from example 44, but using S-3-aminoquinuclidine dihydrochloride. 115 mg (47% of theory) of the title compound are isolated. The analytical data correspond to those of the enantiomeric compound from example 44.

Example 46

N-[(3R)-1-Azabicyclo[2.2.2]oct-3-yl]-7-bromo-1-benzofuran-2-carboxamide

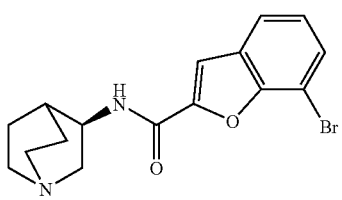

300 mg (1.25 mmol) of 7-bromobenzofuran-2-carboxylic acid, 248 mg (1.25 mmol) of R-3-aminoquinuclidine dihydrochloride, 568 mg (1.494 mmol) of HATU, 579 mg (4.48 mmol) of N,N-diisopropylethylamine and 5 ml of DMF are reacted according to the general procedure (variant B). The product is taken up in methanol and, together with acidic ion exchange resin (Dowex WX2-200), shaken for about 30 min. The loaded ion exchanger is washed with DMF, water, methanol, dichloromethane, water, DMF and once again with methanol. The product is eluted with methanol/triethylamine 90:10. The solvent is removed under reduced pressure using a rotary evaporator. The pre-purified product is purified by preparative HPLC. 320 mg (74% of theory) of the title compound are isolated.

$^1$H NMR (400 MHz, methanol-$d_4$): 8.41 (s, 1H), 7.70 (d, 1H), 7.68-7.60 (m, 2H), 7.25 (t, 1H), 4.54-4.46 (m, 1H), 3.78-3.68 (m, 1H), 3.52-3.38 (m, 1H), 3.38-3.22 (m, 4H), 2.46-2.38 (m, 1H), 2.30-2.18 (m, 1H), 2.18-2.04 (m, 2H), 1.98-1.86 (m, 1H) ppm.

HPLC: R$_t$=3.80 min (Method H)

MS (ESIpos): m/z=349 (M+H)$^+$ (free base)

LC-MS (Method G): R$_t$=2.67 min., m/z=349 (M+H)$^+$ (free base).

Example 47

N-[(3R)-1-Azabicyclo[2.2.2]oct-3-yl]-6-bromo-1-benzofuran-2-carboxamide hydrochloride

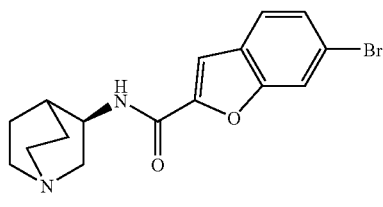

x HCl 3.8 g (15.77 mmol) of 6-bromobenzofuran-2-carboxylic acid, 3.14 g (15.77 mmol) of R-3-aminoquinuclidine dihydrochloride, 7.19 g (18.92 mmol) of HATU, 7.34 g (56.76 mmol) of N,N-diisopropylethylamine and 50 ml of DMF are reacted according to the general procedure (variant B). The crude product is taken up in methanol and, together with acidic ion exchange resin (Dowex WX2-200), shaken for about 20 min. The loaded ion exchanger is washed successively with methanol, dichloromethane and again with methanol. The product is eluted with methanol/triethylamine 90:10. The solvent is removed under reduced pressure using a rotary evaporator. Finally, any last solvent residues are removed under high vacuum. 5.14 g (85% of theory) of the title compound are isolated. For analysis, a small amount of product is converted into the hydrochloride using 4N HCl in dioxane.

$^1$H NMR (200 MHz, DMSO-$d_6$): δ=10.55 (s, 1H, br), 9.22 (d, 1H), 8.05 (s, 1H), 7.75-7.55 (m, 3H), 4.43-4.29 (m, 1H), 3.70-3.55 (m, 1H), 3.45-3.10 (m, 5H), 2.25-2.00 (m, 2H), 1.98-1.82 (m, 2H), 1.80-1.60 (m, 1H) ppm.

HPLC: R$_t$=3.9 min (Method H)

MS (ESIpos): m/z=349 (M+H)$^+$ (free base)

LC-MS (Method G): R$_t$=1.49 min., m/z=349 (M+H)$^+$ (free base).

Example 48

N-[(3R)-1-Azabicyclo[2.2.2]oct-3-yl]naphtho[1,2-b]furan-2-carboxamide hydrochloride

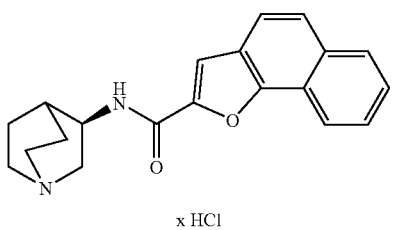

x HCl 210 mg (0.98 mmol) of naphtho[1,2-b]furan-2-carboxylic acid, 200 mg (0.98 mmol) of R-3-aminoquinuclidine dihydrochloride, 450 mg (1.18 mmol) of HATU, 460 mg (3.54 mmol) of N,N-diisopropylethylamine and 2.0 ml of DMF are reacted according to the general procedure (variant B). The reaction mixture is purified by preparative HPLC. An excess of 1N aqueous hydrochloric acid is then added to the product. The solvent is removed under reduced pressure. 74 mg (21% of theory) of the title compound are isolated.

$^1$H NMR (200 MHz, DMSO-$d_6$): δ=9.60 (s, 1H, br), 9.04 (d, 1H), 8.38 (d, 1H), 8.31 (s, 1H), 8.13-8.00 (m, 2H), 7.84 (d, 1H), 7.74-7.56 (m, 2H), 4.43-4.29 (m, 1H), 3.70-3.55 (m, 1H), 3.45-3.10 (m, 5H), 2.25-2.00 (m, 2H), 1.98-1.82 (m, 2H), 1.80-1.60 (m, 1H) ppm.

MS (ESIpos): m/z=321 (M+H)$^+$ (free base)

LC-MS (Method D): $R_t$=3.10 min., m/z=321 (M+H)$^+$ (free base).

Example 49

N-[(3S)-1-Azabicyclo[2.2.2]oct-3-yl]naphtho[1,2-b]furan-2-carboxamide hydrochloride

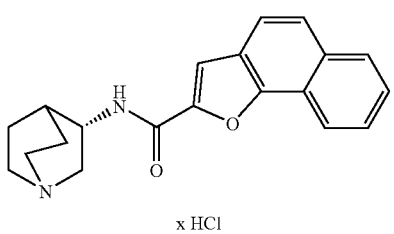

x HCl

The experiment is carried out in the same manner and on the same scale as for the compound from example 48, but using S-3-aminoquinuclidine dihydrochloride. 300 mg (85% of theory) of the title compound are isolated. The analytical data correspond to those of the enantiomeric compound from example 48.

Example 50

N-[(3R)-1-Azabicyclo[2.2.2]oct-3-yl]-6-(2-cyclopropyl-2-oxoethyl)-1-benzofuran-2-carboxamide

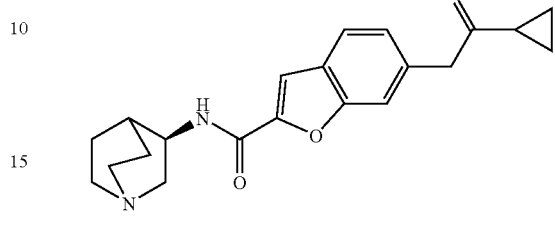

150 mg (0.43 mmol) of N-[(3R)-1-azabicyclo[2.2.2]oct-3-yl]-6-bromo-1-benzofuran-2-carboxamide, 27 mg (0.04 mmol) of rac-BINAP, 45 mg (0.47 mmol) of sodium tert-butoxide and 20 mg (0.02 mmol) of tris(benzylideneacetone) dipalladium are dried under high vacuum for 1 h. Under an atmosphere of argon, 2 ml of dioxane are added. 72 mg (0.86 mmol) of methyl cyclopropyl ketone are added dropwise, and the mixture is heated at 85° C. overnight. The crude product is purified by preparative HPLC. The solvent is removed under reduced pressure. Finally, any last solvent residues are removed under high vacuum. 75 mg (50% of theory) of the title compound are isolated.

$^1$H NMR (400 MHz, methanol-$d_4$): δ=7.62-7.49 (m, 3H), 7.35-7.30 (m, 1H), 4.54-4.45 (m, 1H), 4.04 (s, 2H), 3.87-3.77 (m, 1H), 3.53-3.24 (m, 5H), 2.42-2.31 (m, 1H), 2.30-2.19 (m, 1H), 2.20-2.04 (m, 3H), 1.98-1.88 (m, 1H), 1.01-0.87 (m, 4H) ppm.

HPLC: $R_t$=3.7 min (Method H)

MS (ESIpos): m/z=353 (M+H)$^+$.

Example 51

N-[(3R)-1-Azabicyclo[2.2.2]oct-3-yl]-1-benzothiophene-2-carboxamide hydrochloride

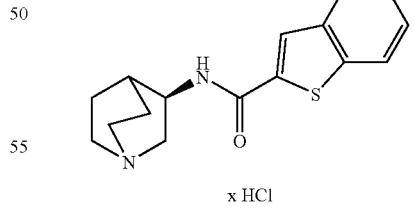

x HCl 322.2 mg (1.81 mmol) of benzothiophene-2-carboxylic acid, 300.0 mg (1.51 mmol) of R-3-aminoquinuclidine dihydrochloride, 687.4 mg (1.81 mmol) of HATU, 701.1 mg (5.43 mmol) of N,N-diisopropylethylamine and 3.0 ml of DMF are reacted according to the general procedure (variant B). The reaction mixture is purified by preparative HPLC. The product is dissolved in a 1:1 mixture of methanol and 1N aqueous hydrochloric acid and then concentrated. 67 mg (13.8% of theory) of the title compound are obtained. The analytical data correspond to those of the racemate (example 13).

Example 52

N-[(3R)-1-Azabicyclo[2.2.2]oct-3-yl]-6-bromo-1-benzothiophene-2-carboxamide hydrochloride

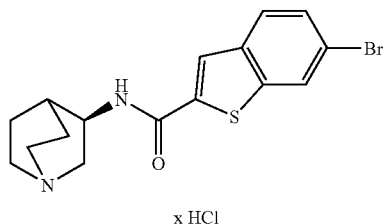

x HCl 900.0 mg (3.50 mmol) of 4-bromo-1-benzothiophene-2-carboxylic acid, 697.0 mg (3.50 mmol) of R-3-aminoquinuclidine dihydrochloride, 1597.1 mg (4.20 mmol) of HATU, 1628.7 mg (12.60 mmol) of N,N-diisopropylethylamine and 8.0 ml of DMF are reacted according to the general procedure (variant B). The reaction mixture is purified by preparative HPLC. The product is dissolved in a 1:1 mixture of 4M HCl in dioxane and 1N aqueous hydrochloric acid and then concentrated. Recrystallization from methanol/ethanol (1:10) gives 594 mg (42.1% of theory) of the title compound.

$^1$H NMR (300 MHz, DMSO-$d_6$): S=9.81 (s, 1H, br), 8.76 (m, 1H), 8.33 (s, 1H), 8.22 (s, 1H), 7.91 (d, 1H), 7.59 (dd, 1H), 4.15 (m, 1H), 3.51-2.93 (m, 6H), 2.12-1.92 (m, 2H), 1.79 (m, 2H), 1.58 (m, 1H) ppm.

HPLC: $R_t$=4.1 min (Method H)

MS (ESIpos): m/z=366 (M, $^{81}$Br)$^+$, 364 (M, $^{79}$Br)$^+$ (free base).

Example 53

N-[(3R)-1-Azabicyclo[2.2.2]oct-3-yl]thieno[2,3-f][1,3]benzodioxole-6-carboxamide hydrochloride

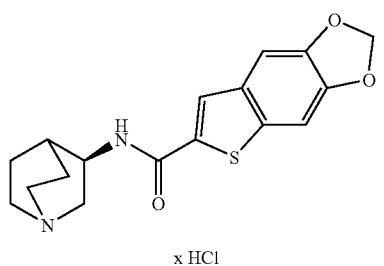

x HCl 122.8 mg (about 0.55 mmol) of a 1:1 mixture of methyl thieno[2,3-f][1,3]benzo-dioxole-6-carboxylate and thieno[2,3-f][1,3]benzodioxole-6-carboxylic acid, 100 mg (0.50 mmol) of R-3-aminoquinuclidine dihydrochloride, 229.1 mg (0.60 mmol) of HATU, 233.7 mg (1.81 mmol) of N,N-diisopropylethylamine and 2.0 ml of DMF are reacted according to the general procedure (variant B). The reaction mixture is purified by preparative HPLC. The product is dissolved in a mixture of methanol and 4M HCl in dioxane and then concentrated and dried under high vacuum. 29 mg (15.8% of theory) of the title compound are obtained.

$^1$H NMR (300 MHz, DMSO-$d_6$): δ=10.18 (s, 1H, br), 8.87 (d, 1H), 8.13 (s, 1H), 7.56 (s, 1H), 7.42 (s, 1H), 6.12 (s, 2H), 4.29 (m, 1H), 3.90-3.55 (m, 2H), 3.43-3.12 (m, 5H), 2.20 (m, 1H), 2.12 (m, 1H), 1.91 (m, 2H), 1.75 (m, 1H) ppm.

HPLC: $R_t$=3.7 min (Method H)

MS (ESIpos): m/z=331 (M+H)$^+$ (free base).

Example 54

N-[(3S)-1-Azabicyclo[2.2.2]oct-3-yl]thieno[2,3-f][1,3]benzodioxole-6-carboxamide hydrochloride

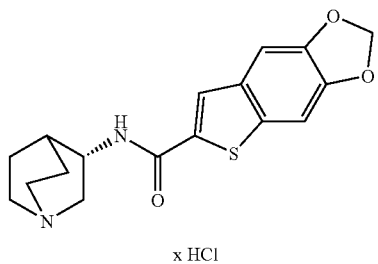

x HCl 122.8 mg (about 0.55 mmol) of a 1:1 mixture of methyl thieno[2,3-f][1,3]benzo-dioxole-6-carboxylate and thieno[2,3-f][1,3]benzodioxole-6-carboxylic acid, 100 mg (0.50 mmol) of S-3-aminoquinuclidine dihydrochloride, 229.1 mg (0.60 mmol) of HATU, 233.7 mg (1.81 mmol) of N,N-diisopropylethylamine and 2.0 ml of DMF are reacted according to the general procedure (variant B). The reaction mixture is purified by preparative HPLC. The product is dissolved in a mixture of methanol and 4M HCl in dioxane and then concentrated and dried under high vacuum. 46 mg (25% of theory) of the title compound are obtained. The analytical data correspond to those of the enantiomeric compound from example 53.

Example 55

N-[(3R)-1-Azabicyclo[2.2.2]oct-3-yl]-5-nitro-1-benzothiophene-2-carboxamide hydrochloride

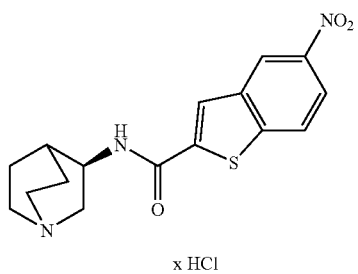

x HCl 420 mg (1.88 mmol) of 5-nitro-1-benzothiophene-2-carboxylic acid, 374.7 mg (1.88 mmol) of R-3-aminoquinuclidine dihydrochloride, 858.6 mg (2.26 mmol) of HATU, 875.5 mg (6.78 mmol) of N,N-diisopropylethylamine and 2.0 ml of DMF are reacted according to the general procedure (variant B). The resulting precipitate is suspended in 1N HCl in diethyl ether, filtered off, washed twice with dichloromethane and dried under high vacuum. 523 mg (75.6% of theory) of the title compound are obtained.

¹H NMR (200 MHz, DMSO-d₆): δ=10.45 (s, 1H, br), 9.43 (d, 1H), 8.37 (m, 1H), 8.60 (s, 1H), 8.30 (m, 2H), 4.35 (m, 1H), 3.65 (m, 1H), 3.40 (m, 2H), 3.23 (m, 3H), 2.24 (m, 1H), 2.17 (m, 1H), 1.93 (m, 2H), 1.76 (m, 1H) ppm.
MS (ESIpos): m/z=332 (M+H)⁺ (free base).

Example 56

N-[(3R)-1-Azabicyclo[2.2.2]oct-3-yl]-3-chloro-6-fluoro-1-benzothiophene-2-carboxamide hydrochloride

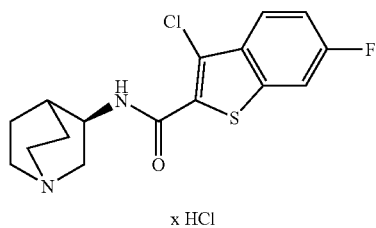

x HCl 191.1 mg (0.83 mmol) of 3-chloro-6-fluoro-1-benzothiophene-2-carboxylic acid, 150.0 mg (0.75 mmol) of R-3-aminoquinuclidine dihydrochloride, 343.7 mg (0.90 mmol) of HATU, 350.5 mg (2.71 mmol) of N,N-diisopropylethylamine and 3.0 ml of DMF are reacted according to the general procedure (variant B). The reaction mixture is purified by preparative HPLC. The product is dissolved in 4M HCl in dioxane, then reconcentrated and dried under high vacuum. 223.3 mg (77.4% of theory) of the title compound are obtained.
¹H NMR (200 MHz, DMSO-d₆): δ=9.67 (m, 1H), 8.82 (d, 1H), 8.11 (dd, 1H), 7.95 (dd, 1H), 7.50 (ddd, 1H), 4.33 (m, 1H), 3.80-3.08 (m, 6H), 2.27 (m, 1H), 2.13 (m, 1H), 2.00-1.68 (m, 3H) ppm.
HPLC: $R_t$=3.9 min (Method H)
MS (ESIpos): m/z=339 (M+H)⁺ (free base).

Example 57

N-[(3S)-1-Azabicyclo[2.2.2]oct-3-yl]-3-chloro-6-fluoro-1-benzothiophene-2-carboxamide hydrochloride

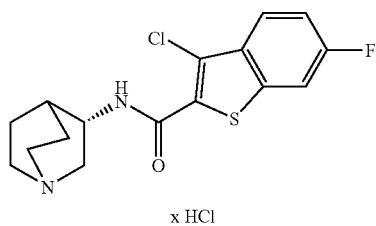

x HCl 158 mg (0.69 mmol) of 3-chloro-6-fluoro-1-benzothiophene-2-carboxylic acid, 124 mg (0.62 mmol) of S-3-aminoquinuclidine dihydrochloride, 284.2 mg (0.75 mmol) of HATU, 289.8 mg (2.24 mmol) of N,N-diisopropylethylamine and 3.0 ml of DMF are reacted according to the general procedure (variant B). The reaction mixture is purified by preparative HPLC. The product is dissolved in a mixture of 4M HCl in dioxane and methanol and then reconcentrated. 190.5 mg (81.5% of theory) of the title compound are obtained. The analytical data correspond to those of the enantiomeric compound from example 56.

Example 58

N-[(3R)-1-Azabicyclo[2.2.2]oct-3-yl]-3-fluoro-1-benzothiophene-2-carboxamide hydrochloride

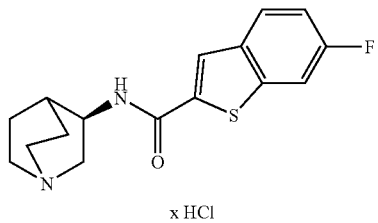

x HCl 162.6 mg (0.83 mmol) of 3-fluoro-1-benzothiophene-2-carboxylic acid, 150.0 mg (0.75 mmol) of R-3-aminoquinuclidine dihydrochloride, 343.7 mg (0.90 mmol) of HATU, 350.5 mg (2.71 mmol) of N,N-diisopropylethylamine and 2.0 ml of DMF are reacted according to the general procedure (variant B). The reaction mixture is purified by preparative HPLC. The product is dissolved in 4M HCl in dioxane, then reconcentrated and dried under high vacuum. 126.9 mg (48% of theory) of the title compound are obtained.
¹H NMR (200 MHz, DMSO-d₆): δ=9.84 (s, 1H, br), 9.11 (d, 1H), 8.39 (d, 1H), 7.85 (d, 1H), 7.51 (m, 1H), 7.38 (m, 1H), 4.32 (m, 1H), 3.78-3.14 (m, 6H), 2.28-2.03 (m, 2H), 1.99-1.66 (m, 3H) ppm.
HPLC: $R_t$=3.9 min (Method H)
MS (ESIpos): m/z=305 (M+H)⁺ (free base).

Example 59

N-[(3S)-1-Azabicyclo[2.2.2]oct-3-yl]-7-fluoro-1-benzothiophene-2-carboxamide hydrochloride

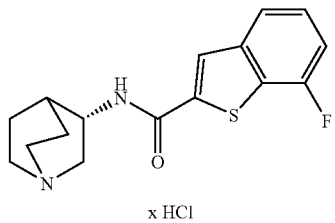

x HCl 162.6 mg (0.83 mmol) of 3-fluoro-1-benzothiophene-2-carboxylic acid, 150.0 mg (0.75 mmol) of S-3-aminoquinuclidine dihydrochloride, 343.7 mg (0.90 mmol) of HATU, 350.5 mg (2.71 mmol) of N,N-diisopropylethylamine and 2.0 ml of DMF are reacted according to the general procedure (variant B). The reaction mixture is purified by preparative HPLC. The product is dissolved in a mixture of methanol and 4M HCl in dioxane, then reconcentrated and dried under high vacuum. 162.8 mg (63% of theory) of the title compound are obtained. The analytical data correspond to those of the enantiomeric compound from example 58.

Example 60

N-[(3R)-1-Azabicyclo[2.2.2]oct-3-yl]-3-chloro-1-benzothiophene-2-carboxamide hydrochloride

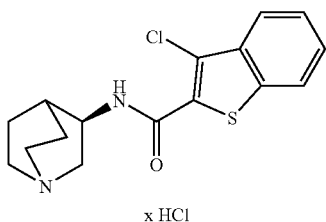

x HCl 356.7 mg (1.68 mmol) of 3-chloro-1-benzothiophene-2-carboxylic acid, 334 mg (1.68 mmol) of R-3-aminoquinuclidine dihydrochloride, 765.3 mg (2.01 mmol) of HATU, 780.5 mg (6.04 mmol) of N,N-diisopropylethylamine and 2.0 ml of DMF are reacted according to the general procedure (variant B). The reaction mixture is purified by preparative HPLC. The product is dissolved in 4M HCl in dioxane and then reconcentrated. 265 mg (44.2% of theory) of the title compound are obtained. The analytical data correspond to those of the racemate (example 14).

Example 61

N-[(3S)-1-Azabicyclo[2.2.2]oct-3-yl]-3-chloro-1-benzothiophene-2-carboxamide hydrochloride

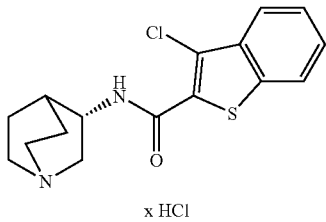

x HCl 254.2 mg (1.20 mmol) of 3-chloro-1-benzothiophene-2-carboxylic acid, 238 mg (1.20 mmol) of S-3-aminoquinuclidine dihydrochloride, 545.4 mg (1.43 mmol) of HATU, 556.1 mg (4.30 mmol) of N,N-diisopropylethylamine and 2.0 ml of DMF are reacted according to the general procedure (variant B). The reaction mixture is purified by preparative HPLC. The product is dissolved in 4M HCl in dioxane and then reconcentrated. 213 mg (49.9% of theory) of the title compound are obtained. The analytical data correspond to those of the racemate (example 14).

Example 62

N-[(3R)-1-Azabicyclo[2.2.2]oct-3-yl]-5-amino-1-benzothiophene-2-carboxamide dihydrochloride

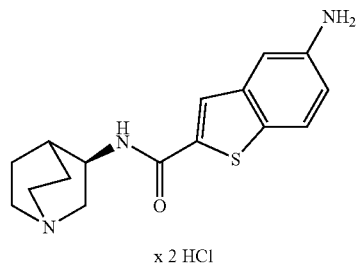

x 2 HCl 385.0 mg (1.05 mmol) of N-[(3R)-1-azabicyclo[2.2.2]oct-3-yl]-5-nitro-1-benzothiophene-2-carboxamide hydrochloride are suspended in 10 ml of a 1:1 mixture of acetic acid and water. 300.0 mg (4.59 mmol) of zinc are added, and the mixture is then stirred at RT for 1 h. The reaction mixture is filtered through kieselguhr, and the filter cake is washed with methanol. The filtrate is concentrated under reduced pressure and the residue is purified by preparative HPLC. The product fraction is dissolved in 4M HCl in dioxane, concentrated under reduced pressure and recrystallized from acetonitrile. 233 mg (59.5% of theory) of the title compound are obtained.

$^1$H NMR (400 MHz, D$_2$O): δ=7.99 (d, 1H), 7.96 (s, 1H), 7.88 (d, 1H), 7.38 (dd, 1H), 4.36 (m, 1H), 3.76 (ddd, 1H), 3.43-3.19 (m, 5H), 2.32 (m, 1H), 2.16 (m, 1H), 2.01 (m, 2H), 1.90 (m, 1H) ppm.

HPLC: R$_t$=2.9 min (Method H)

MS (ESIpos): m/z=302 (M+H)$^+$ (free base).

Example 63

N-[(3S)-1-Azabicyclo[2.2.2]oct-3-yl]-5-amino-1-benzothiophene-2-carboxamide dihydrochloride

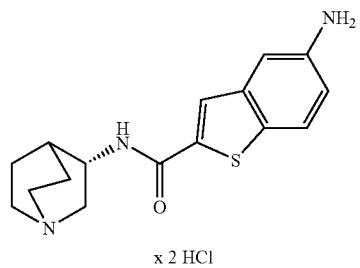

x 2 HCl 422 mg (1.15 mmol) of N-[(3S)-1-azabicyclo[2.2.2]oct-3-yl]-5-nitro-1-benzothiophene-2-carboxamide hydrochloride are suspended in 10 ml of a 1:1 mixture of acetic acid and water. 300.0 mg (4.59 mmol) of zinc are added, the mixture is then stirred at RT for 1 h. The reaction mixture is filtered through kieselguhr, and the filter cake is washed with methanol. The filtrate is concentrated under reduced pressure and the residue is purified by preparative HPLC. The product fraction is dissolved in 4M of HCl in dioxane, concentrated under reduced pressure and recrystallized from acetonitrile.

203 mg (47.3% of theory) of the title compound are obtained. The analytical data correspond to those of the enantiomeric compound from example 62.

Example 64

N-[(3R)-1-Azabicyclo[2.2.2]oct-3-yl]-7-trifluoromethyl-1-benzothiophene-2-carboxamide hydrochloride

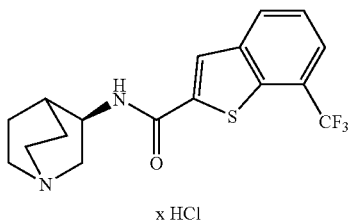

x HCl 204.0 mg (0.83 mmol) of 7-trifluoromethyl-1-benzothiophene-2-carboxylic acid, 150.0 mg (0.75 mmol) of S-3-aminoquinuclidine dihydrochloride, 343.7 mg (0.90 mmol) of HATU, 350.5 mg (2.71 mmol) of N,N-diisopropylethylamine and 3.0 ml of DMF are reacted according to the general procedure. The reaction mixture is purified by preparative HPLC. The product is dissolved in 4M HCl in dioxane, then reconcentrated under dried under high vacuum. 218.8 mg (74.3% of theory) of the title compound are obtained.

$^1$H NMR (400 MHz, DMSO-$d_6$): δ=10.50 (s, 1H, br), 9.41 (d, 1H), 8.60 (s, 1H), 8.28 (d, 1H), 7.92 (d, 1H), 7.68 (dd, 1H), 4.36 (m, 1H), 3.64 (m, 1H), 3.43 (m, 2H), 3.20 (m, 3H), 2.24 (m, 1H), 2.17 (m, 1H), 1.92 (m, 2H), 1.74 (m, 1H) ppm.

HPLC: $R_t$=4.1 min (Method H)

MS (ESIpos): m/z=355 (M+H)$^+$ (free base).

Example 65

N-[(3S)-1-Azabicyclo[2.2.2]oct-3-yl]-7-trifluoromethyl-1-benzothiophene-2-carboxamide hydrochloride

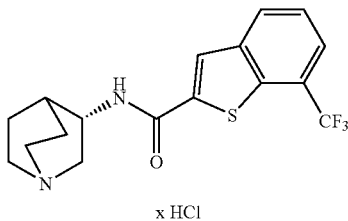

x HCl 204.0 mg (0.83 mmol) of 7-trifluoromethyl-1-benzothiophene-2-carboxylic acid, 150.0 mg (0.75 mmol) of S-3-aminoquinuclidine dihydrochloride, 343.7 mg (0.90 mmol) of HATU, 350.5 mg (2.71 mmol) of N,N-diisopropylethylamine and 3.0 ml of DMF are reacted according to the general procedure (variant B). The reaction mixture is purified by preparative HPLC. The product is dissolved in 4M HCl in dioxane, then reconcentrated and dried under high vacuum. 158.6 mg (53.9% of theory) of the title compound are obtained. The analytical data correspond to those of the enantiomeric compound from example 64.

Example 66

N-[(3R)-1-Azabicyclo[2.2.2]oct-3-yl]-5-trifluoromethyl-1-benzothiophene-2-carboxamide hydrochloride

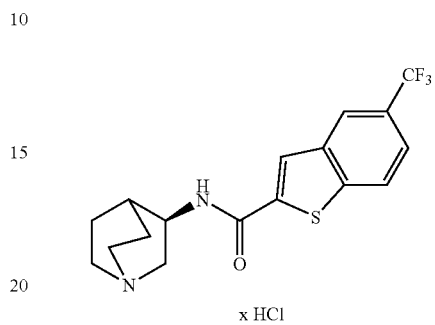

x HCl 204.0 mg (0.83 mmol) of 5-trifluoromethyl-1-benzothiophene-2-carboxylic acid, 150.0 mg (0.75 mmol) of R-3-aminoquinuclidine dihydrochloride, 343.7 mg (0.90 mmol) of HATU, 350.5 mg (2.71 mmol) of N,N-diisopropylethylamine and 2.0 ml of DMF are reacted according to the general procedure (variant B). The reaction mixture is purified by preparative HPLC. The product is dissolved in 4M HCl in dioxane, then reconcentrated and dried under high vacuum. 89 mg (29% of theory) of the title compound are obtained.

$^1$H NMR (400 MHz, D$_2$O+DMSO-$d_6$): δ=8.36 (s, 1H), 8.19 (m, 2H), 7.80 (d, 1H), 4.46 (m, 1H), 3.85 (m, 1H), 3.76-3.52 (m, 1H), 3.50-3.25 (m, 4H), 2.40 (m, 1H), 2.22 (m, 1H), 2.10 (m, 2H), 1.96 (m, 1H) ppm.

HPLC: $R_t$=4.1 min (Method H)

MS (ESIpos): m/z=355 (M+H)$^+$ (free base).

Example 67

5-Amino-N-[(3R)-1-azabicyclo[2.2.2]oct-3-yl]-3-methyl-1-benzothiophene-2-carboxamide dihydrochloride

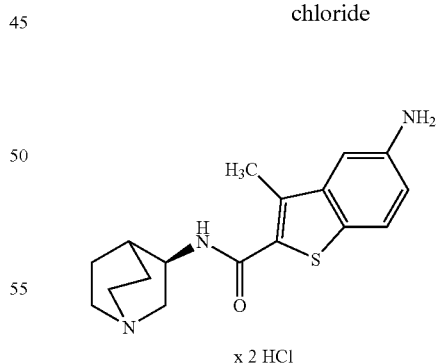

x 2 HCl 317 mg (0.83 mmol) of N-[(3R)-1-azabicyclo[2.2.2]oct-3-yl]-3-methyl-5-nitro-1-benzothiophene-2-carboxamide hydrochloride are suspended in 2 ml of acetic acid. 300.0 mg (4.59 mmol) of zinc are added, and the mixture is then stirred at RT for 1 h. The reaction mixture is filtered through kieselguhr, and the filter cake is washed with methanol. The filtrate is concentrated under reduced pressure and the residue is purified by preparative HPLC. The product fraction is dissolved in 4M HCl in dioxane, concentrated under reduced pressure and recrystallized from acetonitrile. 154 mg (47.8% of theory) of the title compound are obtained.

$^1$H NMR (400 MHz, D$_2$O): δ=8.10 (d, 1H), 7.91 (d, 1H), 7.53 (dd, 1H), 4.52 (m, 1H), 3.92 (m, 1H), 3.52-3.31 (m, 5H), 2.62 (s, 3H), 2.48 (m, 1H), 2.25 (m, 1H), 2.17 (m, 2H), 2.05 (m, 1H) ppm.

MS (ESIpos): m/z=316 (M+H)$^+$ (free base).

Example 68

N-[(3R)-1-Azabicyclo[2.2.2]oct-3-yl]-7-amino-1-benzothiophene-2-carboxamide dihydrochloride

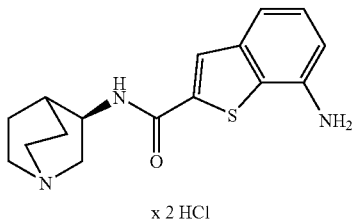

x 2 HCl 87 mg (0.22 mmol) of N-[(3R)-1-azabicyclo[2.2.2]oct-3-yl]-3-bromo-1-benzothiophene-2-carboxamide hydrochloride, 47.1 mg (0.26 mmol) of benzophenoneimine, 12.1 mg (0.02 mmol) of rac-BINAP, 45.8 mg (0.48 mmol) of sodium tert-butoxide and 6.0 mg (0.01 mmol) of Pd$_2$(dba)$_3$ are, under argon, added to a flask which has been dried by heating. 1.5 ml of toluene are added, and the reaction mixture is heated at 80° C. After 30 min, 0.5 ml of THF is added, followed by a further 6.0 mg (0.01 mmol) of Pd$_2$(dba)$_3$ after 6 h. After a further 6 h, the mixture is filtered (0.45 μm filter) and then purified by preparative HPLC. The resulting benzophenoneimine adduct is dissolved in a 1:1 mixture of THF and methanol with addition of 20% by volume of 1N hydrochloric acid. After 1 h at RT, the reaction mixture is concentrated. The solid formed is triturated with acetonitrile and filtered off. Drying under high vacuum gives 17 mg (21% of theory) of the title compound.

$^1$H NMR (400.1 MHz, D$_2$O): δ=8.11 (s, 1H), 7.89 (d, 1H), 7.53 (dd, 1H), 7.37 (d, 1H), 4.48 (m, 1H), 3.87 (m, 1H), 3.52-3.30 (m, 5H), 2.44 (m, 1H), 2.27 (m, 1H), 2.12 (m, 2H), 2.00 (m, 1H) ppm.

HPLC: R$_t$=2.9 min (Method H)

MS (ESIpos): m/z=302 (M+H)$^+$ (free base).

Example 69

N-[(3R)-1-Azabicyclo[2.2.2]oct-3-yl]-7-chloro-1-benzothiophene-2-carboxamide hydrochloride

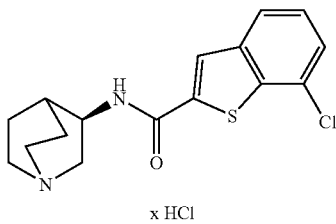

x HCl 176.2 mg (0.83 mmol) of 7-chloro-1-benzothiophene-2-carboxylic acid, 150 mg (0.75 mmol) of R-3-aminoquinuclidine dihydrochloride, 343.7 mg (0.90 mmol) of HATU, 350.5 mg (2.71 mmol) of N,N-diisopropylethylamine and 3.0 ml of DMF are reacted according to the general procedure (variant B). The reaction mixture is purified by preparative HPLC. The product is dissolved in a mixture of 4M HCl in dioxane and methanol and then concentrated. 175.2 mg (65.1% of theory) of the title compound are obtained.

$^1$H NMR (200 MHz, DMSO-d$_6$): δ=10.03 (s, 1H, br), 9.17 (d, 1H), 8.43 (s, 1H), 7.98 (m, 1H), 7.63 (m, 1H), 7.52 (dd, 1H), 4.33 (m, 1H), 3.77-3.10 (m, 6H), 2.28-2.02 (m, 2H), 1.92 (m, 2H), 1.75 (m, 1H) ppm.

HPLC: R$_t$=4.0 min (Method H)

MS (ESIpos): m/z=321 (M+H)$^+$ (free base).

Example 70

N-[(3S)-1-Azabicyclo[2.2.2]oct-3-yl]-7-chloro-1-benzothiophene-2-carboxamide hydrochloride

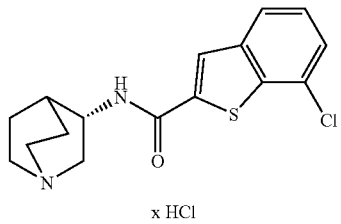

x HCl 176.2 mg (0.83 mmol) of 7-chloro-1-benzothiophene-2-carboxylic acid, 150 mg (0.75 mmol) of S-3-aminoquinuclidine dihydrochloride, 343.7 mg (0.90 mmol) of HATU, 350.5 mg (2.71 mmol) of N,N-diisopropylethylamine and 3.0 ml of DMF are reacted according to the general procedure (variant B). The reaction mixture is purified by preparative HPLC. The product is dissolved in a mixture of 4M HCl in dioxane and methanol and then concentrated. 231.9 mg (85.7% of theory) of the title compound are obtained. The analytical data correspond to those of the enantiomeric compound from example 69.

Example 71

N-[(3R)-1-Azabicyclo[2.2.2]oct-3-yl]-5-(2-furoylamino)-1-benzothiophene-2-carboxamide hydrochloride

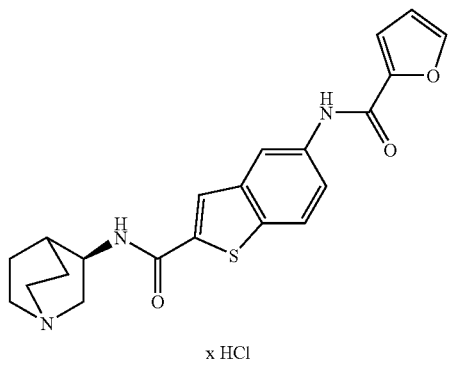

x HCl 30 mg (0.08 mmol) of N-[(3R)-1-azabicyclo[2.2.2]oct-3-yl]-5-amino-1-benzothiophene-2-carboxamide dihydrochloride are dissolved in 1 ml of DMF, and 33.5 μl (0.24 mmol) of triethylamine are added. At 0° C., 15.7 mg (0.12 mmol) of furan-2-carbonyl chloride are added. After 3 h of stirring at RT, the reaction mixture is separated by preparative HPLC. The product fraction is concentrated under reduced pressure and codistilled with 4M HCl in dioxane. 12 mg (34.7% of theory) of the title compound are obtained.

$^1$H NMR (400 MHz, D$_2$O): δ=7.70 (d, 1H), 7.67 (m, 1H), 7.63 (m, 1H), 7.55 (s, 1H), 7.28 (m, 1H), 7.14 (m, 1H), 6.60 (m, 1H), 4.24 (m, 1H), 3.70 (m, 1H), 151-3.21 (m, 5H), 2.28 (m, 1H), 2.20 (m, 1H), 2.10 (m, 2H), 2.00 (m, 1H) ppm.

HPLC: R$_t$=3.6 min (Method H)

LC-MS (Method F): m/z=396 (M+H)$^+$ (free base), R$_t$=2.62 min.

Example 72

N-[(3R)-1-Azabicyclo[2.2.2]oct-3-yl]-5-(benzoylamino)-1-benzothiophene-2-carboxamide hydrochloride

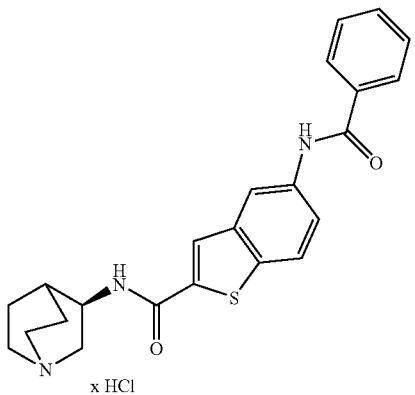

30 mg (0.08 mmol) of N-[(3R)-1-azabicyclo[2.2.2]oct-3-yl]-5-amino-1-benzothiophene-2-carboxamide dihydrochloride are dissolved in 1 ml of DMF, and 33.5 μl (0.24 mmol) of triethylamine are added. At 0° C., 16.9 mg (0.12 mmol) of benzoyl chloride are added. After 3 h of stirring at RT, the reaction mixture is separated by preparative HPLC. The product fraction is concentrated under reduced pressure and codistilled with 4M HCl in dioxane. 9 mg (25.4% of theory) of the title compound are obtained.

LC-MS (Method F): m/z=406 (M+H)$^+$ (free base), R$_t$=2.82 min.

Example 73

6-Amino-N-[(3R)-1-azabicyclo[2.2.2]oct-3-yl]-1-benzothiophene-2-carboxamide dihydrochloride

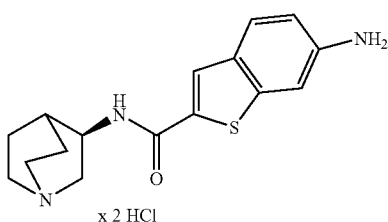

Method A):

15 mg (0.05 mmol) of 6-[(tert-butoxycarbonyl)amino]-1-benzothiophene-2-carboxylic acid, 10.2 mg (0.05 mmol) of R-3-aminoquinuclidine dihydrochloride, 21.4 mg (0.06 mmol) of HATU, 21.8 mg (0.17 mmol) of N,N-diisopropylethylamine and 1 ml of DMF are reacted according to the general procedure (variant B). The reaction mixture is purified by preparative HPLC. 5 ml of 4M HCl in dioxane are added to the product, and the mixture is stirred at RT for 30 min. The mixture is concentrated and the product is dried under high vacuum. 17 mg (98% of theory) of the title compound are obtained.

Method B):

247 mg (0.67 mmol) of N-[(3R)-1-azabicyclo[2.2.2]oct-3-yl]-6-nitro-1-benzothiophene-2-carboxamide hydrochloride are suspended in 1.6 ml of 1N hydrochloric acid and 4.3 ml methanol and, under argon, 25.6 mg of palladium on carbon (5%) are added. Under an atmosphere of hydrogen (atmospheric pressure), the mixture is stirred for 2 h. The contents of the flask are filtered through kieselguhr and the filtrate is evaporated to dryness under reduced pressure. 241 mg (95.6% of theory) of the title compound are obtained.

Method C):

Under argon, 730 mg (1.76 mmol) of N-[(3R)-1-azabicyclo[2.2.2]oct-3-yl]-6-bromo-1-benzothiophene-2-carboxamide hydrochloride, 638.9 mg (3.53 mmol) of benzophenoneimine, 109.8 mg (0.18 mmol) of rac-BINAP, 508.2 mg (5.29 mmol) of sodium tert-butoxide and 161.4 mg (0.18 mmol) of Pd$_2$(dba)$_3$ are added to a flask which had been dried by heating. 10 ml of a 1:1 mixture of THF and toluene are added, and the reaction mixture is heated at 85° C. overnight. The contents of the flask are concentrated to about 7 ml and purified by preparative HPLC. The benzophenoneimine adduct formed is dissolved in 5 ml of methanol and 3 ml of 1N aqueous hydrochloric acid and stirred at RT for 1 h. The solution is concentrated and the product is then recrystallized from methanol/diethyl ether and purified further by preparative HPLC. 1N aqueous hydrochloric acid is added to the product fractions. Concentration and drying under high vacuum gives 67 mg (10.1% of theory) of the title compound.

$^1$H NMR (400 MHz, D$_2$O): δ=7.95 (m, 2H), 7.88 (m, 1H), 7.32 (m, 1H), 4.37 (m, 1H), 3.80-3.69 (m, 2H), 3.40-3.18 (m, 4H), 2.32 (m, 1H), 2.16 (m, 1H), 2.00 (m, 2H), 1.89 (m, 1H) ppm.

HPLC: R$_t$=2.7 min (Method H)

MS (ESIpos): m/z=302 (M+H)$^+$ (free base).

Example 74

N-[(3R)-1-Azabicyclo[2.2.2]oct-3-yl]-5-fluoro-1-benzothiophene-2-carboxamide hydrochloride

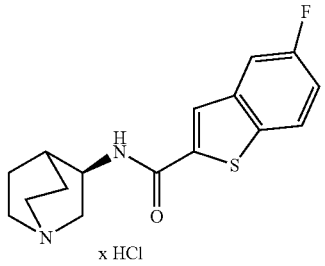

162.6 mg (0.83 mmol) of 5-fluoro-1-benzothiophene-2-carboxylic acid, 150.0 mg (0.75 mmol) of R-3-aminoquinuclidine dihydrochloride, 343.7 mg (0.90 mmol) of HATU, 350.5 mg (2.71 mmol) of N,N-diisopropylethylamine and 3.0 ml of DMF are reacted according to the general procedure (variant B). The reaction mixture is purified by preparative HPLC. The product is dissolved in a mixture of methanol and 4M HCl in dioxane, then reconcentrated and dried under high vacuum. 144.0 mg (56.1% of theory) of the title compound are obtained.

$^1$H NMR (300 MHz, DMSO-d$_6$): δ=10.01 (s, 1H, br), 9.03 (d, 1H), 8.27 (s, 1H), 8.08 (dd, 1H), 7.81 (dd, 1H), 7.38 (ddd, 1H), 4.32 (m, 1H), 3.67 (m, 1H), 3.43-3.15 (m, 5H), 2.24 (m, 1H), 2.13 (m, 1H), 1.93 (m, 2H), 1.77 (m, 1H) ppm.

HPLC: R$_t$=3.8 min (Method H)
MS (ESIpos): m/z=305 (M+H)$^+$ (free base).

Example 75

N-[(3S)-1-Azabicyclo[2.2.2]oct-3-yl]-5-fluoro-1-benzothiophene-2-carboxamide hydrochloride

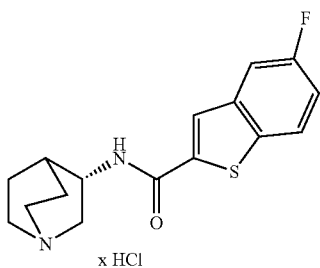

162.6 mg (0.83 mmol) of 5-fluoro-1-benzothiophene-2-carboxylic acid, 150 mg (0.75 mmol) of S-3-aminoquinuclidine dihydrochloride, 343.7 mg (0.90 mmol) of HATU, 350.5 mg (2.71 mmol) of N,N-diisopropylethylamine and 3.0 ml of DMF are reacted according to the general procedure (variant B). The reaction mixture is purified by preparative HPLC. The product is dissolved in a mixture of 4M HCl in dioxane and methanol and then reconcentrated. 127.6 mg (49.7% of theory) of the title compound are obtained. The analytical data correspond to those of the enantiomeric compound from example 74.

Example 76

N-[(3R)-1-Azabicyclo[2.2.2]oct-3-yl]-7-methoxy-1-benzothiophene-2-carboxamide hydrochloride

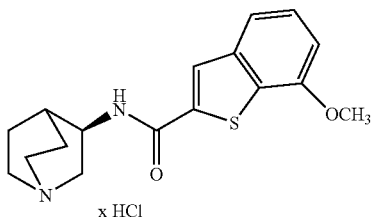

115 mg (0.55 mmol) of 7-methoxy-1-benzothiophene-2-carboxylic acid, 100 mg (0.50 mmol) of R-3-aminoquinuclidine dihydrochloride, 229.1 mg (0.60 mmol) of HATU, 233.7 mg (1.81 mmol) of N,N-diisopropylethylamine and 2.0 ml of DMF are reacted according to the general procedure (variant B). The reaction mixture is purified by preparative HPLC. The product is dissolved in a mixture of methanol and 4M HCl in dioxane, then reconcentrated and dried under high vacuum. 176.9 mg (95.6% of theory) of the title compound are obtained.

$^1$H NMR (200 MHz, DMSO-d$_6$): δ=9.45 (m, 1H), 8.86 (d, 1H), 8.20 (s, 1H), 7.77 (d, 1H), 7.43 (dd, 1H), 7.06 (d, 1H), 4.31 (m, 1H), 3.98 (s, 3H), 3.80-3.10 (m, 6H), 2.21 (m, 1H), 2.13 (m, 1H), 1.93 (m, 2H), 1.78 (m, 1H) ppm.

HPLC: R$_t$=3.8 min (Method H)
MS (ESIpos): m/z=317 (M+H)$^+$ (free base).

Example 77

N-[(3S)-1-Azabicyclo[2.2.2]oct-3-yl]-7-methoxy-1-benzothiophene-2-carboxamide hydrochloride

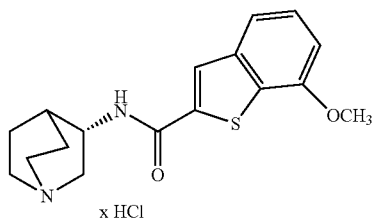

103.5 mg (0.50 mmol) of 7-methoxy-1-benzothiophene-2-carboxylic acid, 90 mg (0.45 mmol) of S-3-aminoquinuclidine dihydrochloride, 206.2 mg (0.54 mmol) of HATU, 210.3 mg (1.62 mmol) of N,N-diisopropylethylamine and 2.0 ml of DMF are reacted according to the general procedure (variant B). The reaction mixture is purified by preparative HPLC. The product is dissolved in a mixture of methanol and 4M HCl in dioxane, then reconcentrated and dried under high vacuum. 105.6 mg (66.2% of theory) of the title compound are obtained. The analytical data correspond to those of the enantiomeric compound from example 76.

Example 78

N-[(3R)-1-Azabicyclo[2.2.2]oct-3-yl]-4-fluoro-1-benzothiophene-2-carboxamide hydrochloride

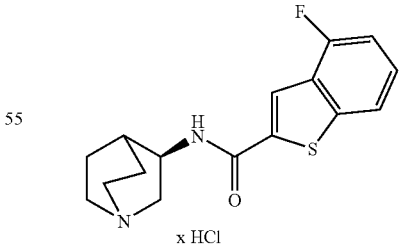

197.1 mg (1.00 mmol) of 4-fluoro-1-benzothiophene-2-carboxylic acid, 125.0 mg (0.63 mmol) of R-3-aminoquinuclidine dihydrochloride, 286.4 mg (0.75 mmol) of HATU, 292.1 mg (2.26 mmol) of N,N-diisopropylethylamine and 3.0 ml of DMF are reacted according to the general procedure (variant B). The reaction mixture is purified by preparative HPLC. The product is dissolved in a mixture of methanol and 4M HCl in dioxane, then reconcentrated and dried under high vacuum. 160.1 mg (73.3% of theory) of the title compound are obtained.

HPLC: $R_t$=3.8 min (Method H)

MS (ESIpos): m/z=305 (M+H)$^+$ (free base).

Example 79

N-[(3S)-1-Azabicyclo[2.2.2]oct-3-yl]-4-fluoro-1-benzothiophene-2-carboxamide hydrochloride

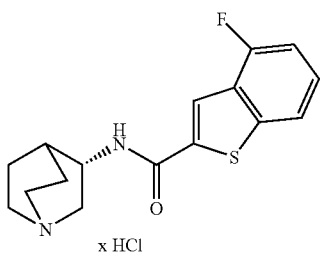

197.1 mg (1.00 mmol) of 4-fluoro-1-benzothiophene-2-carboxylic acid, 125.0 mg (0.63 mmol) of S-3-aminoquinuclidine dihydrochloride, 286.4 mg (0.75 mmol) of HATU, 292.1 mg (2.26 mmol) of N,N-diisopropylethylamine and 3.0 ml of DMF are reacted according to the general procedure (variant B). The reaction mixture is purified by preparative HPLC. The product is dissolved in a mixture of methanol and 4M HCl in dioxane, then reconcentrated and dried under high vacuum. 85.7 mg (40.1% of theory) of the title compound are obtained. The analytical data correspond to those of the enantiomeric compound from example 78.

Example 80

N-[(3R)-1-Azabicyclo[2.2.2]oct-3-yl]-5,7-difluoro-1-benzothiophene-2-carboxamide hydrochloride

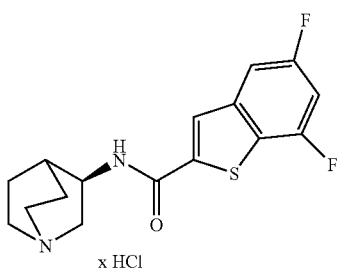

177.5 mg (0.83 mmol) of 5,7-difluoro-1-benzothiophene-2-carboxylic acid, 150.0 mg (0.75 mmol) of R-3-aminoquinuclidine dihydrochloride, 343.7 mg (0.90 mmol) of HATU, 350.5 mg (2.71 mmol) of N,N-diisopropylethylamine and 3.0 ml of DMF are reacted according to the general procedure (variant B). The reaction mixture is purified by preparative HPLC. The product is dissolved in a mixture of methanol and 4M HCl in dioxane, then reconcentrated and dried under high vacuum. 110.4 mg (40.8% of theory) of the title compound are obtained.

$^1$H NMR (200 MHz, DMSO-d$_6$): δ=10.14 (s, 1H, br), 9.26 (d, 1H), 8.40 (d, 1H), 7.78 (dd, 1H), 7.52 (ddd, 1H), 4.31 (m, 1H), 3.65 (m, 1H), 3.50-3.07 (m, 5H), 2.22 (m, 1H), 2.14 (m, 1H), 1.90 (m, 2H), 1.75 (m, 1H) ppm.

HPLC: $R_t$=3.9 min (Method H)

MS (ESIpos): m/z=323 (M+H)$^+$ (free base).

Example 81

N-[(3S)-1-Azabicyclo[2.2.2]oct-3-yl]-5,7-difluoro-1-benzothiophene-2-carboxamide hydrochloride

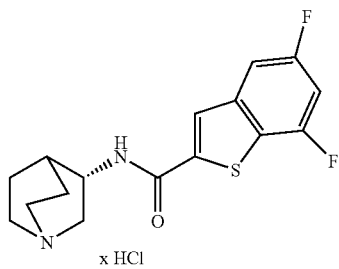

177.5 mg (0.83 mmol) of 5,7-difluoro-1-benzothiophene-2-carboxylic acid, 150.0 mg (0.75 mmol) of S-3-aminoquinuclidine dihydrochloride, 343.7 mg (0.90 mmol) of HATU, 350.5 mg (2.71 mmol) of N,N-diisopropylethylamine and 3.0 ml of DMF are reacted according to the general procedure (variant B). The reaction mixture is purified by preparative HPLC. The product is dissolved in a mixture of methanol and 4M HCl in dioxane, then reconcentrated and dried under high vacuum. 109.3 mg (40.4% of theory) of the title compound are obtained. The analytical data correspond to those of the enantiomeric compound from example 80.

Example 82

N-[(3R)-1-Azabicyclo[2.2.2]oct-3-yl]-6-methoxy-1-benzothiophene-2-carboxamide hydrochloride

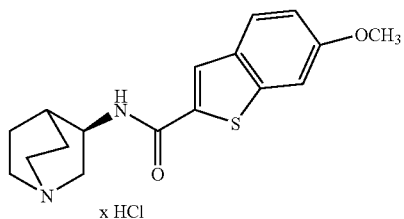

100 mg (0.48 mmol) of 6-methoxy-1-benzothiophene-2-carboxylic acid, 86.9 mg (0.44 mmol) of R-3-aminoquinuclidine dihydrochloride, 199.2 mg (0.52 mmol) of HATU, 203.13 mg (1.57 mmol) of N,N-diisopropylethylamine and 1.5 ml of DMF are reacted according to the general procedure (variant B). The reaction mixture is purified by preparative HPLC. The product is dissolved in a mixture of methanol and 4M HCl in dioxane, then reconcentrated and dried under high vacuum. 118.2 mg (76.7% of theory) of the title compound are obtained.

$^1$H NMR (200 MHz, DMSO-d$_6$): δ=9.77 (s, 1H, br), 8.83 (d, 1H), 8.17 (s, 1H), 7.85 (d, 1H), 7.60 (d, 1H), 7.07 (dd, 1H), 4.30 (m, 1H), 3.84 (s, 3H), 3.79-3.45 (m, 2H), 3.39-3.10 (m, 4H), 2.20 (m, 1H), 2.10 (m, 1H), 1.90 (m, 2H), 1.75 (m, 1H) ppm.

HPLC: $R_t$=3.8 min (Method H)

MS (ESIpos): m/z=317 (M+H)$^+$ (free base).

Example 83

N-[(3S)-1-Azabicyclo[2.2.2]oct-3-yl]-6-methoxy-1-benzothiophene-2-carboxamide hydrochloride

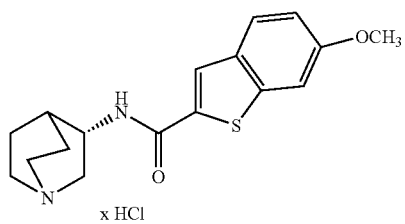

x HCl 100 mg (0.48 mmol) of 6-methoxy-1-benzothiophene-2-carboxylic acid, 86.9 mg (0.44 mmol) of S-3-aminoquinuclidine dihydrochloride, 199.2 mg (0.52 mmol) of HATU, 203.13 mg (1.57 mmol) of N,N-diisopropylethylamine and 1.5 ml of DMF are reacted according to the general procedure (variant B). The reaction mixture is purified by preparative HPLC. The product is dissolved in a mixture of methanol and 4M HCl in dioxane, then reconcentrated and dried under high vacuum. 112.5 mg (73% of theory) of the title compound are obtained. The analytical data correspond to those of the enantiomeric compound from example 82.

Example 84

N-[(3R)-1-Azabicyclo[2.2.2]oct-3-yl]-6-cyano-1-benzothiophene-2-carboxamide hydrochloride

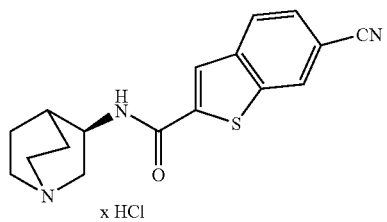

x HCl 320.8 mg (1.1 mmol) of 6-cyano-1-benzothiophene-2-carboxylic acid, 200 mg (1.0 mmol) of R-3-aminoquinuclidine dihydrochloride, 458.3 mg (1.21 mmol) of HATU, 467.3 mg (3.62 mmol) of N,N-diisopropylethylamine and 4.0 ml of DMF are reacted according to the general procedure (variant B). The reaction mixture is purified by preparative HPLC. The product is dissolved in a mixture of methanol and 4M HCl in dioxane, then reconcentrated and dried under high vacuum. 222.1 mg (63.6% of theory) of the title compound are obtained.

$^1$H NMR (300 MHz, DMSO-$d_6$): δ=9.80 (m, 1H), 9.12 (d, 1H), 8.68 (s, 1H), 8.37 (s, 1H), 8.16 (d, 1H), 7.83 (dd, 1H), 4.33 (m, 1H), 3.76-3.05 (m, 6H), 2.23 (m, 1H), 2.13 (m, 1H), 1.92 (m, 2H), 1.76 (m, 1H) ppm.

HPLC: $R_t$=3.6 min (Method H)

MS (ESIpos): m/z=312 (M+H)$^+$ (free base).

Example 85

N-[(3S)-1-Azabicyclo[2.2.2]oct-3-yl]-6-cyano-1-benzothiophene-2-carboxamide hydrochloride

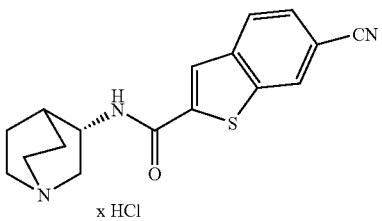

x HCl 112.2 mg (0.39 mmol) of 6-cyano-1-benzothiophene-2-carboxylic acid, 70 mg (0.35 mmol) of S-3-aminoquinuclidine dihydrochloride, 160.4 mg (0.42 mmol) of HATU, 163.5 mg (1.26 mmol) of N,N-diisopropylethylamine and 1.5 ml of DMF are reacted according to the general procedure (variant B). The reaction mixture is purified by preparative HPLC. The product is dissolved in a mixture of methanol and 4M HCl in dioxane, then reconcentrated and dried under high vacuum. 250.1 mg (41% of theory) of the title compound are obtained. The analytical data correspond to those of the enantiomeric compound from example 84.

Example 86

N-[(3R)-1-Azabicyclo[2.2.2]oct-3-yl]-4-nitro-1-benzothiophene-2-carboxamide hydrochloride

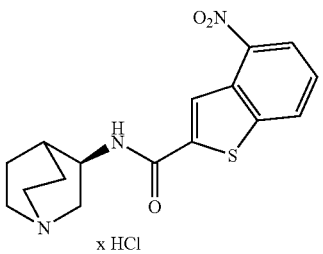

x HCl 246.6 mg (1.10 mmol) of 4-nitro-1-benzothiophene-2-carboxylic acid, 200 mg (1.00 mmol) of R-3-aminoquinuclidine dihydrochloride, 458.3 mg (1.21 mmol) of HATU, 467.4 mg (3.62 mmol) of N,N-diisopropylethylamine and 4.0 ml of DMF are reacted according to the general procedure (variant B). The reaction mixture is purified by preparative HPLC. The product is dissolved in a mixture of methanol and 4M HCl in dioxane, then reconcentrated and dried under high vacuum. 134.3 mg (35.6% of theory) of the title compound are obtained.

$^1$H NMR (200 MHz, DMSO-$d_6$): δ=9.70 (s, 1H, br), 9.23 (d, 1H), 8.49 (s, 1H), 8.57 (d, 1H), 8.43 (dd, 1H), 7.73 (dd, 1H), 4.32 (m, 1H), 3.82-3.10 (m, 6H), 2.27 (m, 1H), 2.13 (m, 1H), 1.93 (m, 2H), 1.77 (m, 1H) ppm.

HPLC: $R_t$=3.8 min (Method H)

MS (ESIpos): m/z=332 (M+H)$^+$ (free base).

Example 87

N-[(3S)-1-Azabicyclo[2.2.2]oct-3-yl]-4-nitro-1-benzothiophene-2-carboxamide hydrochloride

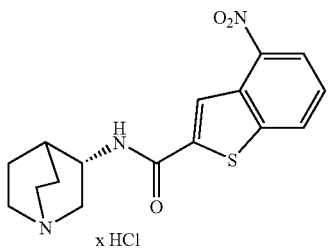

246.6 mg (1.10 mmol) of 4-nitro-1-benzothiophene-2-carboxylic acid, 200 mg (1.00 mmol) of S-3-aminoquinuclidine dihydrochloride, 458.3 mg (1.21 mmol) of HATU, 467.4 mg (3.62 mmol) of N,N-diisopropylethylamine and 4.0 ml of DMF are reacted according to the general procedure (variant B). The reaction mixture is purified by preparative HPLC. The product is dissolved in a mixture of methanol and 4M HCl in dioxane, then reconcentrated and dried under high vacuum. 128.5 mg (34.8% of theory) of the title compound are obtained after recrystallization from methanol. The analytical data correspond to those of the enantiomeric compound from example 86.

Example 88

6-(Acetylamino)-N-[(3R)-1-azabicyclo[2.2.2]oct-3-yl]-1-benzothiophene-2-carboxamide hydrochloride

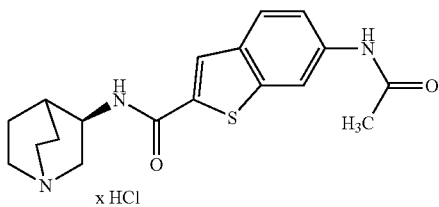

50 mg (0.12 mmol) of 6-amino-N-[(3R)-1-azabicyclo[2.2.2]oct-3-yl]-1-benzothiophene-2-carboxamide dihydrochloride are initially charged in 0.3 ml of DMF, and 18.7 mg (0.18 mmol) of triethylamine and 11.6 mg (0.15 mmol) of acetyl chloride are added. After 16 h of stirring at RT, a further 18.7 mg (0.18 mmol) of triethylamine and 11.6 mg (0.15 mmol) of acetyl chloride are added. After a further 12 h of stirring at RT, the supernatant solution of the reaction mixture is purified by preparative HPLC. The product fractions are concentrated and the residue is dissolved in a mixture of methanol and 4M HCl in dioxane, then reconcentrated and dried under high vacuum. 8 mg (17.1% of theory) of the title compound are obtained.

$^1$H NMR (400 MHz, methanol-$d_4$): δ=8.34 (m, 1H), 8.06 (s, 1H), 7.83 (d, 1H), 7.47 (dd, 1H), 4.45 (m, 1H), 3.83 (m, 1H), 3.49 (m, 1H), 3.42-3.26 (m, 4H), 2.38 (m, 1H), 2.28 (m, 1H), 2.17 (s, 3H), 2.10 (m, 2H), 1.95 (m, 1H) ppm.

HPLC: $R_t$=3.3 min (Method H)

MS (ESIpos): m/z=344 (M+H)$^+$ (free base).

Example 89

N-[(3R)-1-Azabicyclo[2.2.2]oct-3-yl]-4-amino-1-benzothiophene-2-carboxamide dihydrochloride

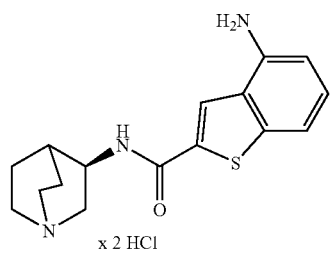

2 ml of methanol and 460 μl of 1N hydrochloric acid are added to 70 mg (0.19 mmol) of 4-nitro-1-benzothiophene-2-carboxylic acid. 7 mg of palladium-on-carbon (10%) are added, and the reaction mixture is then hydrogenated at RT and atmospheric pressure for 2 h. The reaction mixture is filtered through kieselguhr and purified by preparative HPLC. The product fractions are concentrated, a mixture of methanol and 4M HCl in dioxane is added and the mixture is then again concentrated and dried under high vacuum. 75.5 mg (98.7% of theory) of the title compound are obtained.

$R_t$=2.9 min (Method H)

MS (ESIpos): m/z=302 (M+H)$^+$ (free base).

Example 90

N-[(3R)-1-Azabicyclo[2.2.2]oct-3-yl]-3-chloro-6-amino-1-benzothiophene-2-carboxamide dihydrochloride

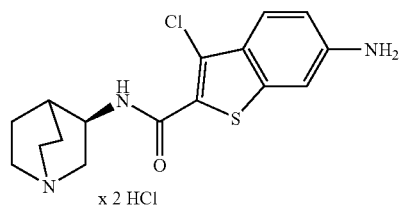

83 mg (0.23 mmol) of N-[(3R)-1-azabicyclo[2.2.2]oct-3-yl]-3-chloro-6-nitro-1-benzothiophene-2-carboxamide hydrochloride are dissolved in 1.5 ml of 2M tin(II) chloride solution in DMF and stirred at RT for 14 h. The reaction mixture is purified by preparative HPLC. The product fractions are concentrated, dissolved in a mixture of methanol and 4M HCl in dioxane, then again concentrated and dried under high vacuum. 53 mg (57.2% of theory) of the title compound are obtained.

$^1$H NMR (300 MHz, methanol-$d_4$): δ=7.69 (d, 1H), 7.20 (d, 1H), 7.02 (dd, 1H), 4.46 (m, 1H), 3.83 (m, 1H), 3.52-3.25 (m, 5H), 2.42 (m, 1H), 2.27 (m, 1H), 2.11 (m, 2H), 2.02 (m, 1H) ppm.

HPLC: $R_t$=3.0 min (Method H)

MS (ESIpos): m/z=336 (M+H)$^+$ (free base).

Example 91

N-[(3R)-1-Azabicyclo[2.2.2]oct-3-yl]-6-(isopropylamino)-1-benzothiophene-2-carboxamide dihydrochloride

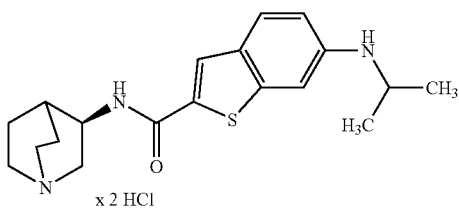

A solution of 150 mg (0.40 mmol) of 6-amino-N-[(3R)-1-azabicyclo[2.2.2]oct-3-yl]-1-benzothiophene-2-carboxamide dihydrochloride and 48 µl (0.65 mmol) of acetone in 1.5 ml of 1,2-dichloroethane is adjusted to pH 4 using acetic acid. 254.8 mg (1.20 mmol) of sodium triacetoxyborohydride are added, and the mixture is stirred at RT for 6 h. The contents of the flask are concentrated under reduced pressure and purified by preparative HPLC. The product fractions are concentrated and the residue is dissolved in a 5:1 mixture of acetonitrile and 1N hydrochloric acid, then again concentrated and dried under high vacuum. 49 mg (29.4% of theory) of the title compound are obtained.

$^1$H NMR (300 MHz, methanol-$d_4$): δ=8.32 (s, 1H), 8.15 (m, 2H), 7.53 (dd, 1H), 4.49 (m, 1H), 3.88 (m, 1H), 3.83 (m, 1H), 3.56 (m, 1H), 3.50-3.23 (m, 4H), 2.39 (m, 1H), 2.31 (m, 1H), 2.11 (m, 2H), 1.95 (m, 1H), 1.39 (d, 6H) ppm.

HPLC: $R_t$=3.1 min (Method H)
MS (ESIpos): m/z=344 (M+H)$^+$ (free base).

Example 92

6-[(Z)-Amino(hydroxyimino)methyl]-N-[(3R)-1-azabicyclo[2.2.2]oct-3-yl]-1-benzothiophene-2-carboxamide dihydrochloride

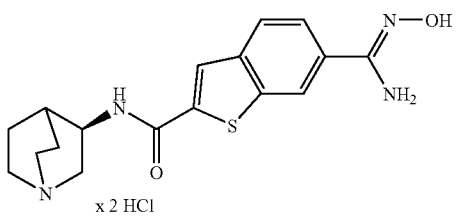

800 mg (2.0 mmol) of N-[(3R)-1-azabicyclo[2.2.2]oct-3-yl]-6-cyano-1-benzothiophene-2-carboxamide hydrochloride, 278.1 mg (4.0 mmol) of hydroxylamine hydrochloride and 829.5 mg (6.0 mmol) of potassium carbonate in 8 ml of an 8:1 mixture of water and ethanol are heated at 80° C. for 3 h. The mixture is purified by column chromatography on silica gel (mobile phase: dichloromethane/methanol/25% ammonia 100:20:4). The product fractions are combined and concentrated, methanol and 4M HCl in dioxane are added and the mixture is then again concentrated and dried under high vacuum. 447.3 mg (53.6% of theory) of the title compound are obtained.

$^1$H NMR (200 MHz, DMSO-$d_6$): δ=11.15 (m, 1H), 10.22 (m, 1H), 9.36 (d, 1H), 8.52 (s, 1H), 8.46 (m, 1H), 8.14 (d, 1H), 7.73 (dd, 1H), 4.33 (m, 1H), 3.93-3.10 (m, 6H), 2.32-2.05 (m, 2H), 1.93 (m, 2H), 1.75 (m, 1H) ppm.

HPLC: $R_t$=2.9 min (Method H)
MS (ESIpos): m/z=345 (M+H)$^+$ (free base).

Example 93

N-[(3R)-1-Azabicyclo[2.2.2]oct-3-yl]-7-cyano-1-benzothiophene-2-carboxamide hydrochloride

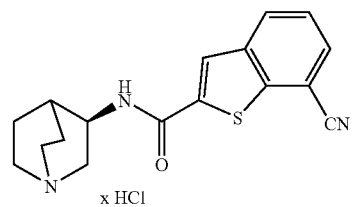

1.5 g (7.38 mmol) of 7-cyano-1-benzothiophene-2-carboxylic acid and 1.47 g (7.38 mmol) of R-3-aminoquinuclidine dihydrochloride are initially charged in 25 ml of DMF. At 0° C., 1.70 g (8.86 mmol) of EDC, 1.20 g (8.86 mmol) of HOBt and 3.70 ml (26.6 mmol) of triethylamine are added to the solution. The mixture is stirred at RT for 18 h. The reaction is terminated by addition of a 10% strength aqueous sodium bicarbonate solution, and ethyl acetate is added. The resulting precipitate is filtered off with suction. The mother liquor is extracted twice with ethyl acetate. The organic phases are combined and concentrated. The crude product is purified by silica gel column chromatography (mobile phase: dichloromethane/methanol/25% ammonia 100:20:4). The product fractions are concentrated, dissolved in a mixture of methanol and 1N hydrochloric acid, then again concentrated and dried under high vacuum. 655.1 mg (24.5% of theory) of the title compound are obtained.

HPLC: $R_t$=3.7 min (Method H)
MS (ESIpos): m/z=312 (M+H)$^+$ (free base).

Example 94

N-[(3R)-1-Azabicyclo[2.2.2]oct-3-yl]-7-nitro-1-benzothiophene-2-carboxamide hydrochloride

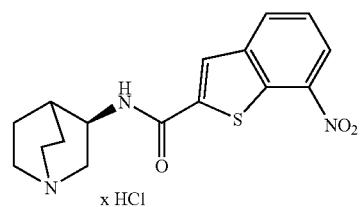

2.0 g (8.96 mmol) of 7-nitro-1-benzothiophene-2-carboxylic acid and 1.78 g (8.96 mmol) of R-3-aminoquinuclidine dihydrochloride are initially charged in 25 ml of DMF.

At 0° C., 2.06 g (10.75 mmol) of EDC, 1.45 g (10.75 mmol) of HOBt and 4.50 ml (32.26 mmol) of triethylamine are added to the solution. The mixture is stirred at RT for 18 h. The reaction is terminated by addition of a 10% strength aqueous sodium bicarbonate solution, and ethyl acetate is added. The resulting precipitate is filtered off with suction. The mother liquor is extracted twice with ethyl acetate. The organic phases are combined and concentrated. Both the precipitate and the concentrated mother liquor are purified by silica gel column chromatography (mobile phase: dichloromethane/methanol/25% ammonia 100:10:2). The product fractions are concentrated, dissolved in a mixture of methanol and 1N hydrochloric acid, then again concentrated and dried under high vacuum. The resulting solid is triturated with acetonitrile, filtered off with suction and dried at 50° C. under reduced pressure. 1.10 g (32.8% of theory) of the title compound are obtained.

$^1$H NMR (500 MHz, DMSO-$d_6$): δ=9.90 (s, 1H, br), 9.25 (d, 1H), 8.56 (d, 1H), 8.50 (s, 1H), 8.49 (d, 1H), 7.78 (dd, 1H), 4.37 (m, 1H), 3.69 (m, 1H), 3.62-3.19 (m, 5H), 2.23 (m, 1H), 2.14 (m, 1H), 1.93 (m, 2H), 1.78 (m, 1H) ppm.

HPLC: $R_t$=3.8 min (Method H)

MS (ESIpos): m/z=332 (M+H)$^+$ (free base).

Example 95

N-[(3R)-1-Azabicyclo[2.2.2]oct-3-yl]-6-[(methylsulfonyl)amino]-1-benzothiophene-2-carboxamide hydrochloride

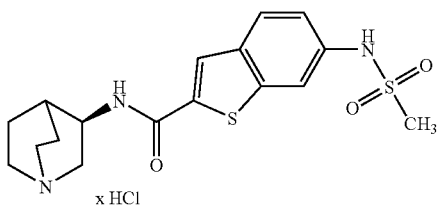

40 mg (0.11 mmol) of N-[(3R)-1-azabicyclo[2.2.2]oct-3-yl]-6-amino-1-benzothiophene-2-carboxamide hydrochloride are dissolved in 2 ml of DMF, 6.5 mg (0.05 mmol) of N,N-dimethyl-4-aminopyridine, 59.6 μl (0.43 mmol) of triethylamine and 16.61 (0.21 mmol) of methanesulfonyl chloride are added and the mixture is stirred at room temperature for 16 h. The reaction mixture is purified by preparative HPLC. The product is dissolved in a mixture of 1N aqueous hydrochloric acid and acetonitrile, then reconcentrated and dried under high vacuum. 15 mg (33.8% of theory) of the title compound are obtained.

$^1$H NMR (400 MHz, methanol-$d_4$): δ=8.07 (s, 1H), 7.87 (d, 1H), 7.81 (d, 1H), 7.32 (dd, 1H), 4.44 (m, 1H), 3.83 (m, 1H), 3.48 (m, 1H), 3.42-3.24 (m, 4H), 3.00 (s, 3H), 2.37 (m, 1H), 2.27 (m, 1H), 2.10 (m, 2H), 1.95 (m, 1H) ppm.

HPLC: $R_t$=3.3 min (Method H)

MS (ESIpos): m/z=380 (M+H)$^+$ (free base).

Example 96

N-[(3R)-1-Azabicyclo[2.2.2]oct-3-yl]-6-[bis(phenylsulfonyl)amino]-1-benzothiophene-2-carboxamide hydrochloride

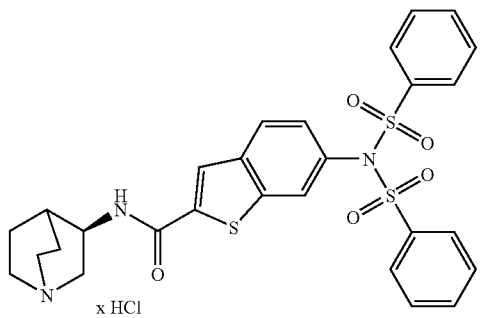

40 mg (0.11 mmol) of N-[(3R)-1-azabicyclo[2.2.2]oct-3-yl]-6-amino-1-benzothiophene-2-carboxamide hydrochloride are dissolved in 2 ml of DMF, 6.5 mg (0.05 mmol) of N,N-dimethyl-4-aminopyridine, 59.6 μl (0.43 mmol) of triethylamine and 27.2 μl (0.21 mmol) of benzenesulfonyl chloride are added and the mixture is stirred at room temperature for 16 h. The reaction mixture is purified by preparative HPLC. The product is dissolved in a mixture of 1N aqueous hydrochloric acid and acetonitrile, then again concentrated and dried under high vacuum. 33 mg (50% of theory) of the title compound are obtained.

$^1$H NMR (400 MHz, methanol-$d_4$): S=8.13 (s, 1H), 7.94-7.82 (m, 5H), 7.78 (m, 2H), 7.68-7.55 (m, 5H), 7.01 (dd, 1H), 4.45 (m, 1H), 3.84 (m, 1H), 3.47 (m, 1H), 3.42-3.22 (m, 4H), 2.39 (m, 1H), 2.28 (m, 1H), 2.10 (m, 2H), 1.95 (m, 1H) ppm.

HPLC: $R_t$=4.4 min (Method H)

MS (ESIpos): m/z=582 (M+H)$^+$ (free base).

Example 97

N-[(3R)-1-Azabicyclo[2.2.2]oct-3-yl]-6-(benzoylamino)-1-benzothiophene-2-carboxamide hydrochloride

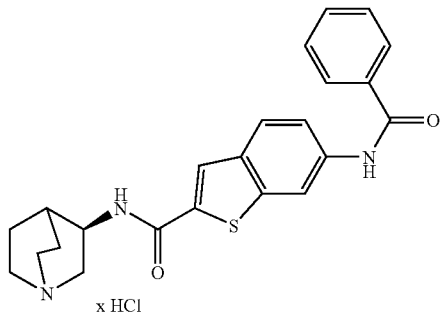

40 mg (0.11 mmol) of N-[(3R)-1-azabicyclo[2.2.2]oct-3-yl]-6-amino-1-benzothiophene-2-carboxamide dihydrochloride are dissolved in 2 ml of DMF, and 59.6 μl (0.43 mmol) of triethylamine are added. 30 mg (0.21 mmol) of benzoyl chloride are added. The reaction mixture is stirred at RT for 18 h and then separated by preparative HPLC. The product fraction is concentrated under reduced pressure, a mixture of acetonitrile and 1N hydrochloric acid is added, and the mixture is then again concentrated and dried under high vacuum. 32 mg (67.8% of theory) of the title compound are obtained.

$^1$H NMR (400 MHz, methanol-$d_4$): δ=8.46 (s, 1H), 8.11 (s, 1H), 8.01-7.93 (m, 2H), 7.89 (d, 1H), 7.49 (dd, 1H), 7.58 (d, 1H), 7.56-7.48 (m, 2H), 4.46 (m, 1H), 3.83 (m, 1H), 3.50 (m, 1H), 3.44-3.24 (m, 4H), 2.38 (m, 1H), 2.28 (m, 1H), 2.10 (m, 2H), 1.95 (m, 1H) ppm.

HPLC: $R_t$=4.6 min (Method H)

MS (ESIpos): m/z=406 (M+H)$^+$ (free base).

Example 98

7-[(Z)-Amino(hydroxyimino)methyl]-N-[(3R)-1-azabicyclo[2.2.2]oct-3-yl]-1-benzothiophene-2-carboxamide dihydrochloride

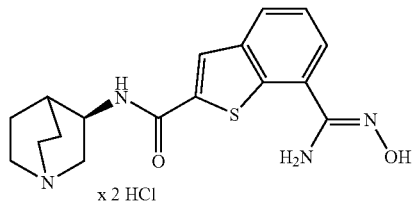

120 mg (0.43 mmol) of N-[(3R)-1-azabicyclo[2.2.2]oct-3-yl]-7-cyano-1-benzothiophene-2-carboxamide hydrochloride, 45.0 mg (0.65 mmol) of hydroxylamine hydrochloride and 119.2 mg (0.86 mmol) of potassium carbonate in 1.5 ml of an 8:1 mixture of water and ethanol are heated at 80° C. for 18 h. The mixture is purified by preparative HPLC. The product fractions are combined and concentrated, acetonitrile and 1N aqueous hydrochloric acid (3:1) are added and the mixture is then again concentrated and dried under high vacuum. 58 mg (30.3% of theory) of the title compound are obtained.

$^1$H NMR (300 MHz, methanol-$d_4$): δ=8.34 (s, 1H), 8.23 (d, 1H), 7.73 (d, 1H), 7.65 (dd, 1H), 4.48 (m, 1H), 3.82 (m, 1H), 3.56 (m, 1H), 3.48-3.16 (m, 4H), 2.39 (m, 1H), 2.30 (m, 1H), 2.10 (m, 2H), 1.96 (m, 1H) ppm.

HPLC: $R_t$=2.8 min (Method H)

MS (ESIpos): m/z=345 (M+H)$^+$ (free base).

What is claimed is:

1. A method for treating a cognitive impairment in a patient suffering from Alzheimer's disease or schizophrenia, the method comprising administering to a patient a therapeutically effective amount a compound of formula (I):

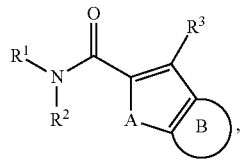

wherein
$R^1$ represents 1-azabicyclo[2.2.2]oct-3-yl,
$R^2$ represents hydrogen or $C_1$-$C_6$-alkyl,
$R^3$ represents hydrogen, halogen or $C_1$-$C_6$-alkyl,
A represents oxygen or sulfur,
and
the ring B represents benzo, pyrimido, pyrimidazo or pyridazino which is substituted by a radical selected from the group consisting of halogen, $C_1$-$C_6$-alkanoyl, carbamoyl, cyano, trifluoromethyl, trifluoromethoxy, nitro, amino, $C_1$-$C_6$-acylamino, $C_1$-$C_6$-alkyl, $C_1$-$C_6$-alkyoxy, $C_1$-$C_6$-alkylthio, $C_1$-$C_6$-alkylamino, heteroarylcarbonylamino, arylcarbonylamino, $C_1$-$C_6$-alkylsulfonyl-amino, di($C_1$-$C_4$-alkylsulfonyl)amino, arylsulfonylamino, di(arylsulfonyl)amino, $C_3$-$C_6$-cycloalkylcarbonylmethyl, 1,3-dioxa-propane-1,3-diyl, amino(hydroxyimino)methyl and benzo,
or a salt, a hydrate or a hydrate of a salt thereof.

2. The method of claim 1 wherein the treatment improves one or more of perception, concentration, learning and memory in the subject.

3. The method of claim 1,
wherein
$R^1$ represents 1-azabicyclo[2.2.2]oct-3-yl,
$R^2$ represents hydrogen or $C_1$-$C_6$-alkyl,
$R^3$ represents hydrogen, halogen or $C_1$-$C_6$-alkyl,
A represents oxygen or sulfur,
and
the ring B represents benzo, pyrimido, pyridazo or pyridazino which is substituted by a radical selected from the group consisting of halogen, formyl, carbamoyl, cyano, trifluoromethyl, trifluoromethoxy, nitro, amino, formamido, acetamido, ($C_1$-$C_6$-alkyl, ($C_1$-$C_6$)-alkoxy, ($C_1$-$C_6$)-alkylthio and benzo,
or a salt, a hydrate or a hydrate of a salt thereof.

4. The method of claim 3 wherein the compound has formula (Ia):

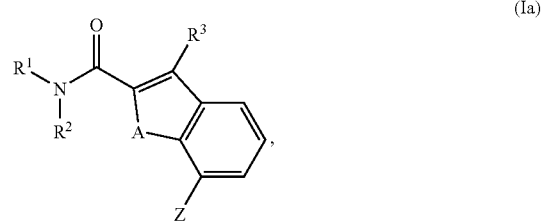

wherein
$R^1$ represents 1-azabicyclo[2.2.2]oct-3-yl,
$R^2$ represents hydrogen or $C_1$-$C_6$-alkyl,
$R^3$ represents hydrogen, halogen or $C_1$-$C_6$-alkyl,
A represents oxygen or sulfur,
and
Z represents halogen, formyl, carbamoyl, cyano, trifluoromethyl, trifluoromethoxy, nitro, amino, formamido, acetamido, C1-C6-alkyl, C1-C6-alkyoxy, C1-C6-alkylthio, C1-C6-alkylamino, heteroaryl-carbonylamino, arylcarbonylamino, C1-C4-alkylsulfonylamino, di(arylsulfonyl)amino, C3-C6-cycloalkylcarbonylmethyl or amino(hydroxyimino)methyl,
or a salt, a hydrate or a hydrate of a salt thereof.

5. The method of claim 1, wherein Z is selected from the group consisting of: halogen, cyano, trifluoromethyl, trifluoromethoxy, methyl, ethyl, methoxy, and ethoxy.

6. The method of claim 2, wherein Z is selected from the group consisting of: halogen, cyano, trifluoromethyl, trifluoromethoxy, methyl, ethyl, methoxy, and ethoxy.

7. The method of claim 3, wherein Z is selected from the group consisting of: halogen, cyano, trifluoromethyl, trifluoromethoxy, methyl, ethyl, methoxy, and ethoxy.

8. The method of claim 4, wherein Z is selected from the group consisting of: halogen, cyano, trifluoromethyl, trifluoromethoxy, methyl, ethyl, methoxy, and ethoxy.

9. The method of claim 1, wherein the compound is N-[(3R)-1-Azabicyclo[2.2.2]oct-3-yl]-7-fluoro-1-benzofuran-2-carboxamide.

10. The method of claim 1, wherein the compound is N-[(3R)-1-Azabicyclo[2.2.2]oct-3-yl]-5-fluoro-1-benzothiophene-2-carboxamide.

11. The method of claim 1, wherein the compound is N-[(3R)-1-Azabicyclo[2.2.2]oct-3-yl]-5,7-difluoro-1-benzothiophene-2-carboxamide.

12. The method of claim 1, wherein the compound is N-[(3R)-1-Azabicyclo[2.2.2]oct-3-yl]-5-fluoro-1-benzofuran-2-carboxamide.

13. The method of claim 1, wherein the compound is N-[(3R)-1-Azabicyclo[2.2.2]oct-3-yl]-5-chloro-1-benzofuran-2-carboxamide.

14. The method of claim 1, wherein the compound is N-[(3R)-1-Azabicyclo[2.2.2]oct-3-yl]-5,7-difluoro-1-benzofuran-2-carboxamide.

15. The method of claim 1, wherein the compound is N-[(3R)-1-Azabicyclo[2.2.2]oct-3-yl]-7-fluoro-1-benzothiophene-2-carboxamide.

16. The method of claim 1, wherein the compound is N-[(3R)-1-Azabicyclo[2.2.2]oct-3-yl]-7-chloro-1-benzothiophene-2-carboxamide.

17. The method of claim 1, wherein the compound is N-[(3R)-1-Azabicyclo[2.2.2]oct-3-yl]-7-cyano-1-benzothiophene-2-carboxamide.

18. The method of claim 1, wherein the compound is N-[(3R)-1-Azabicyclo[2.2.2]oct-3-yl]-7-trifluoromethyl-1-benzothiophene-2-carboxamide.

* * * * *